US007556957B2

(12) United States Patent
Rottier et al.

(10) Patent No.: US 7,556,957 B2
(45) Date of Patent: Jul. 7, 2009

(54) CORONAVIRUS-LIKE PARTICLES COMPRISING FUNCTIONALLY DELETED GENOMES

(75)

WT= rMHV-WT

Fig. 3

FIG. 7A Vector

Intergenic promoter sequence

GGATATCTAATCTAAACTTTAG

Primer 1286

Sequence in front of renilla
and firefly luciferase

Primer 1287  ACGTCCTATAGATTAGATTTGAAATCGATC

EcoRV

Virus-Cell Entry Inhibition of MHV-EFLM by the HR2 Peptide

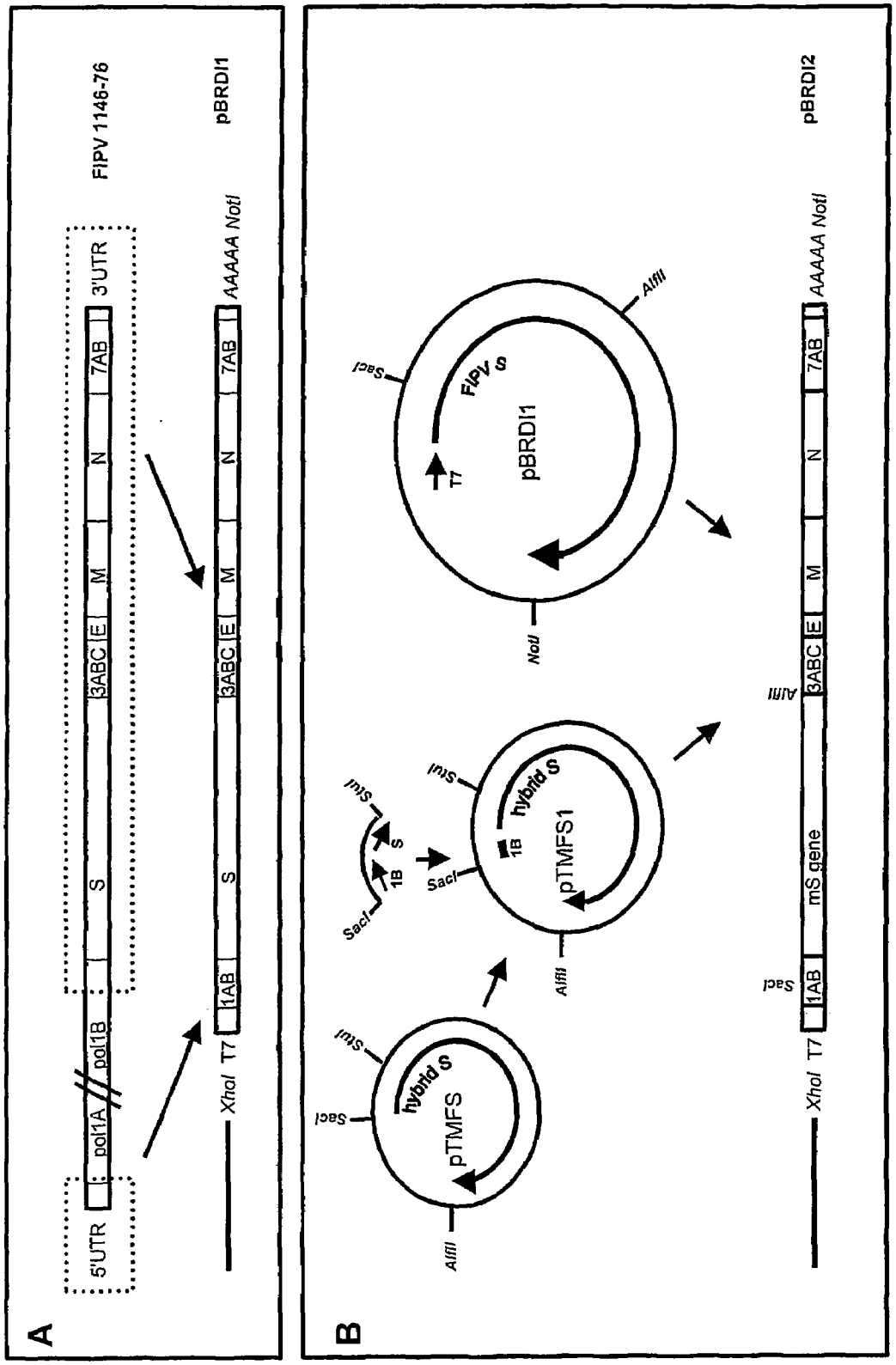
Fig.13: Construction of RNA donor vector pBRDI1 and pBRDI2

A   CTCGAG  TCGAAATTAATACGACTCACTATA   G*GG   TTTTTAAAGTAAAGTGAGTGTA ...
    *Xho I*        T7 promoter              5' FIPV

B   
    5' 702 bp ◄——— *SacI* ———► 3' 9262 bp
    ..GTTATTGAAGGT GAGCTC | TGGACTGTGTTTTGTACA ..
       V  I  E  G  E  L  W | T  V  F  C  T
              Pol1A         Pol1B

C   TAGTGATAC   AAAAAAAAAAAAAA   GCGGCCGC
    3'UTR       polyA tail      *NotI*

Stop FIPV 1B gene
         ......P  C  C  S  C  L  F  Y  F  C  P  L  V
D   GTTAATGTGCC *ATG* CTGTTCGTGTTATTCTATTTTTGCCCTCTTGTT   *TAG* GGT
                M  L  F  V  F  I  L  F  L  P  S......
                Start MHV S gene

Fig. 14: Sequence details of pDRDI contructs

Fig. 19A and B

Fig. 20

TABLE 1

1) S ← E D * GAGGATTGACTATCACAGCCCCTGCAGGAAAGACAGAA[AATCTAAAC]AATTTA → 4a

2) S ← E D * GAGGATTGACTATCACAGCCCCATCT[AATCCAAAC]ATTATG —M→ M

3) M ← R T * AGAACCTAAGATGGAAAGACAGAA[AATCTAAAC]AATTTA → 4a

4) E ← D I * GATATCT[AATCTAAAC]TTTAAGGATG —M→ N 5) 1b ← V K * GTCAAATAAAGCTTGCATGAGGCAT[AATCTAAAC]ATG —M→ S 6) 1b ← V K * GTCAAATAAGCGGAAAGACAGAA[AATCTAAAC]AATTTA → 4a

7) M ← R T * AGAACCTAAGATAGCTTGCATGAGGCAT[AATCTAAAC]ATG —M→ S

8) S ← E D * GAGGATTGACTATCACAGCCCCCGCGCA R A → M remnant 9) 1b ← V K * GTCAAATAAAGCTATCT[AATCCAAAC]ATTATG —M→ M

Fig. 21

Table 2: Primers used for SOE-PCR, location of primers relative to the DNA sequence of pBRDI1

| Primer | Gene | Location | Sense | Sequence |
|---|---|---|---|---|
| 1 | S | 5168-5185 | + | 5'GCCATTCTCATTGATAAC3' |
| 2 | M | 7567-7587 | - | 5'GCTTCTGTTGAGTAATCACC3' |
| 3 | S, E | 5478-5497 6594-6604 | + | 5'GTCATTACAGGTCTTGTATG/ACGTTCCCTAGGGC3' |
| 4 | S | 5478-5497 | - | 5'CATACAAGACCTGTAATGAC3' |
| 5 | M | 7567-7586 | + | 5'GGTGATTACTCAACAGAAGC3' |
| 6 | polyA | 9995-10012 | - | 5'GCGGCCGCTTTTTTTTTTTT3' |
| 7 | N,7B | 8767-8782 9703-9722 | + | 5'GAGGTTACGAATTAAACTGAGTTATAAGGCAAC3' |
| 8 | N | 8767-8782 | - | 5'TTTAATTCGTAACCTC3' |
| 9 | E | 6638-6659 | - | 5'CAGGAGCCAGAAGAAGACGCTAA3' |
| 10 | N | 8174-8193 | + | 5'CTCAATCTAGAGGAAGACACC3' |
| 11 | 3'UTR | | - | 5'GACCAGTTTTAGACATCG3' |

Addendum 1: DNA sequence pBRDI1

```
CTCGAGTCGAAATTAATACGACTCACTATAGGGTTTTTAAAGTAAAGTGAGTGTAGCGTGGCTATAACTCTTCTTTTACT
TTAACTAGCCTTGTGCTAGATTTGTCTTCGGACACCAACTCGAACTAAACGAAATATTTGTCTCTCTATGAAACCATAGA
AGACAAGCGTTGATTATTTCACCAGTTTGGCAATCACTCCTAGGAACGGGGTTGAGAGAACGGCGCACCAGGGTTCCGTC
CCTGTTTGGTAAGTCGTCTAGTATTAGCTGCGGCGGTTCCGCCCGTCGTAGTTGGGTAGACGGGTTCCGTCCTGTGATC
TCCCTCGCCGGCCGCCAGGAGAATGAGTTCCAAACAATTTAAGATCCTCGTTAATGAGGACTACCAAGTCAACGTTCCTA
GCCTTCCTTTCCGTGACGCACTGCAGGAAATTAAGTACTGCTACCGTAACGGTTTTGATGGCTATGTCTTCGTGCCTGAA
TACCGTCGTGACCTAGTTGATTGCAATCGTAAGGATCACTACGTCATTGGTGTTTTGGGTAACGGAATAAGTGATCTTAA
ACCTGTTCTCCTTACCGAACCTTCCGTCATGTTGCAGGGTTTCATTGTTAGAGCCAACTGCAATGGCGTTCTTGAGGACT
TTGACCTTAAATTCGCCCGTACTGGAAACGGCGCCATATATGTGGACCAATACATGTGTGGTGCTGATGGAAAGCCAGTT
ATTGAAGGTGAGCTCTGGACTGTGTTTTGTACAAGTGTTAATACGTCATCATCAGAAGGTTTTCTGATTGGTATTAACTA
CTTAGGACCATACTGTGACAAAGCAATAGTAGATGGAAATATAATGCATGCCAATTATATATTTTGGAGAAACTCTACAA
TTATGGCTCTATCACATAACTCAGTCCTAGACACTCCAAAATTTAAGTGCCGTTGTAACAATGCACTTATTGTTAATTTA
AAAGAAAAAGAATTGAATGAAATGGTCGTTGGATTACTAAGGAAGGGTAAGTTACTCATTAGAAATAATGGCAAGCTACT
AAACTTTGGTAATCATTTAGTTAATGTGCCATGATTGTGCTCGTAACTTGCCTCTTGTTGTTATGTTCATACCACACAGT
TTTGAGTACAACAAATAATGAATGCATACAAGTTAACGTAACACAATTGGCTGGCAATGAAAACCTTATCAGAGATTTTC
TGTTTAGTAACTTTAAAGAAGAAGGAAGTGTAGTTGTTGGTGGTTATTACCCTACAGAGGTGTGGTACAACTGCTCTAGA
ACAGCTCGAACTACTGCCTTTCAGTATTTTAATAATATACATGCCTTTTATTTTGTTATGGAAGCCATGGAAAATAGCAC
TGGTAATGCACGTGGTAAACCATTATTATTTCATGTGCATGGTGAGCCTGTTAGTGTTATTATATCGGCTTATAGGGATG
ATGTGCAACAAAGGCCCCTTTTAAAACATGGGTTAGTGTGCATAACTAAAAATCGCCATATTAACTATGAACAATTCACC
TCCAACCAGTGGAATTCCACATGTACGGGTGCTGACAGAAAAATTCCTTTCTCTGTCATACCCACGGACAATGGAACAAA
AATCTATGGTCTTGAGTGGAATGATGACTTTGTTACAGCTTATATTAGTGGTCGTTCTTATCACTTGAACATCAATACTA
ATTGGTTTAACAATGTCACACTTTTGTATTCACGCTCAAGCACTGCTACCTGGGAATACAGTGCTGCATATGCTTACCAA
GGTGTTTCTAACTTCACTTATTACAAGTTAAATAACACCAATGGTCTAAAAACCTATGAATTATGTGAAGATTATGAACA
TTGCACTGGCTATGCTACCAATGTATTTGCTCCGACATCAGGTGGTTACATACCTGATGGATTTAGTTTTAACAATTGGT
TCTTGCTTACAAATAGTTCCACTTTTGTTAGTGGCAGGTTTGTAACAAATCAACCATTATTGATTAATTGCTTGTGGCCA
GTGCCCAGTTTTGGTGTAGCAGCACAAGAATTTTGTTTTGAAGGTGCACAGTTTAGCCAATGTAATGGTGTGTCTTTAAA
TAACACAGTGGATGTTATTAGATTCAACCTTAATTTCACTGCAGATGTACAATCTGGTATGGGTGCTACAGTATTTTCAC
TGAATACAACAGGTGGTGTCATTCTTGAAATTTCATGTTATAGTGACACAGTGAGTGAGTCTAGTTCTTACAGTTATGGT
GAAATCCCGTTCGGCATAACTGACGGACCACGATACTGTTATGTACTTTACAATGGCACAGCTCTTAAATATTTAGGAAC
ATTACCACCCAGTGTAAAGGAAATTGCTATTAGTAAGTGGGGCCATTTTTATATTAATGGTTACAATTTCTTTAGCACAT
TTCCTATTGGTTGTATATCTTTTAATTTAACCACTGGTGTTAGTGGAGCTTTTTGGACAATTGCTTACACATCGTATACT
GAAGCATTAGTACAAGTTGAAAACACAGCTATTAAAAATGTGACGTATTGTAACAGTCACATTAATAACATTAAATGTTC
TCAACTTACTGCTAATTTGAATAATGGATTTTATCCTGTTGCTTCAAGTGAAGTAGGTTTCGTTAATAAGAGTGTTGTGT
TATTACCTAGCTTTTTCACATACACCGCTGTCAATATAACCATTGATCTTGGTATGAAGCTTAGTGGTTATGGTCAACCC
ATAGCCTCGACACTAAGTAACATCACACTACCAATGCAGGATAACAATACTGATGTGTACTGTATTCGTTCTAACCAATT
CTCAGTTTATGTTCATTCCACTTGCAAAAGTTCTTTATGGGACAATATTTTTAATCAAGACTGCACGGATGTTTTAGAGG
CTACAGCTGTTATAAAAACTGGTACTTGTCCTTTCTCATTTGATAAATTGAACAATTACTTGACTTTTAACAAGTTCTGT
TTGTCGTTGAGTCCTGTTGGTGCTAATTGCAAGTTTGATGTTGCTGCACGTACAAGAACCAATGAGCAGGTTGTTAGAAG
TCTATATGTAATATATGAAGAAGGAGACAACATAGTGGGTGTACCGTCTGATAATAGCGGTCTGCACGATTTGTCTGTGC
TACACCTAGACTCCTGTACAGATTACAATATATATGGTAGAACTGGTGTTGGTATTATTAGACGAACTAACAGTACGCTA
CTTAGTGGCTTATATTACACATCACTATCAGGTGATTTGTTAGGCTTTAAAAATGTTAGTGATGGTGTCATTTATTCTGT
GACGCCATGTGATGTAAGCGCACAAGCGGCTGTTATTGGTGCCGTCAGTTGGAGCTATGACTTCCATTAACAGTGAAC
TGTTAGGTCTAACACATTGGACAACGACACCTAATTTTTATTACTACTCTATATATAATTACACAAGTGAGAGGACTCGT
GGCACTGCAATTGACAGTAACGATGTTGATTGTGAACCTGTCATAACCTATTCTAATATAGGTGTTTGTAAAAATGGTGC
TTTGGTTTTTATTAACGTCACACATTCTGACGGAGACGTGCAACCAATTAGCACTGGTAATGTCACGATACCTACAAATT
TTACTATATCTGTGCAAGTTGAATACATGCAGGTTTACACTACACCAGTATCAATAGATTGTGCAAGATACGTTTGTAAT
GGTAACCCTAGATGTAACAAATTGTTAACACAATATGTGTCTGCATGTCAAACTATTGAACAAGCACTTGCAATGGGTGC
CAGACTTGAAAACATGGAGGTTGATTCCATGTTGTTTGTCTCGGAAAATGCCCTTAAATTGGCATCTGTTGAGGCGTTCA
ATAGTACAGAAAATTTAGATCCTATTTACAAAGAATGGCCTAGCATAGGTGGTTCTTGGCTAGGAGGTCTAAAAGATATA
CTACCGTCCCATAATAGCAAACGTAAGTATGGTTCTGCTATAGAAGATTTGCTTTTTGATAAAGTTGTAACATCTGGTTT
AGGTACAGTTGATGAAGATTATAAACGTTGTACTGGTGGTTACGACATAGCAGACTTGGTGTGTGCTCAATATTACAATG
GCATCATGGTTCTACCAGGTGTAGCTAATGCTGACAAGATGACTATGTACACAGCATCACTTGCAGGTGGTATAACATTA
GGTGCACTTGGTGGTGGCGCCGTGGCTATACCTTTTGCAGTAGCAGTACAGGCTAGACTTAATTATGTTGCTCTACAAAC
TGATGTATTGAATAAAAACCAACAGATCCTGGCTAATGCTTTCAATCAAGCTATTGGTAACATTACACAGGCTTTTGGTA
AGGTTAATGATGCTATACATCAAACATCACAAGGTCTTGCCACTGTTGCTAAAGCGTTGGCAAAAGTGCAAGATGTTGTC
AACACACAAGGGCAAGCTTTAAGTCACCTTACAGTACAATTGCAAAATAATTTTCAAGCCATTAGTAGTTCTATTAGTGA
TATTTATAACAGGCTTGACGAACTGAGTGCTGATGCACAAGTTGATAGGCTGATTACAGGTAGACTTACAGCACTTAATG
CATTTGTGTCTCAGACTCTAACCAGACAAGCAGAGGTTAGGGCTAGTAGACAACTTGCCAAAGACAAGGTTAATGAATGT
```

Fig. 23, contd.

```
GTTAGGTCTCAGTCTCAGAGATTCGGATTCTGTGGTAATGGTACACATTTGTTTTCACTAGCAAATGCAGCACCAAATGG
CATGATTTTCTTTCATACAGTACTATTACCAACAGCTTATGAAACTGTAACAGCTTGGTCAGGTATTTGTGCTTCAGATG
GCGATCGCACTTTCGGACTTGTCGTTAAAGATGTGCAGTTGACGTTGTTTCGTAATCTAGATGACAAGTTCTATTTGACC
CCCAGAACTATGTATCAGCCTAGAGTTGCAACTAGTTCTGATTTTGTTCAAATTGAAGGGTGTGATGTGTTGTTTGTCAA
CGCGACTGTAATTGATTTGCCTAGTATTATACCTGACTATATTGACATTAATCAAACTGTTCAAGACATATTAGAAAATT
ACAGACCAAACTGGACTGTACCTGAATTTACACTTGATATTTTCAACGCAACCTATTTAAATCTGACTGGTGAAATTGAT
GACTTAGAGTTTAGGTCAGAAAAGCTACATAACACTACAGTAGAACTTGCCATTCTCATTGATAACATTAATAATACATT
AGTCAATCTTGAATGGCTCAATAGAATTGAAACTTATGTAAAATGGCCTTGGTATGTGTGGCTACTGATAGGTTTAGTAG
TAGTATTTTGCATACCATTACTGCTATTTTGCTGTTTTAGCACAGGTTGTTGTGGATGCATAGGTTGTTTAGGAAGTTGT
TGTCACTCTATATGTAGTAGAAGACAATTTGAAAATTATGAACCAATTGAAAAAGTGCATGTCCACTAAATTTAAAGTTA
AGGATGTTGAATAAATTCCTTAAGAACTAAACTTATTAGTCATTACAGGTCTTGTATGGACATTGTCAAATCTATTGACA
TATTCGTAGACGCTGTACTTGACGAACTTGACCGTGCATACTTTGCTGTAACTCTTAAAGTAGAATTTAAGACTGGTAAA
CTACTTGTGTGTATAGGTTTTGGTGACACACTTCTTGAGGCTAAGGACAAAGCGTATGCTAAGCTTGGTCTCTCCTTTAT
TGAAGAAGTCAATAGTCATACAGTTGTTTAGTATTACTGTTTACAAGTTTAAAGCCAAATTTTGGTATAAACTACCTTTT
GAAACTAGACTTTGTATCATTAAACACACAAGACCCAAAGCATTAAGTGTTACAAAACAAGTAAAGAGAGATTATAGAAA
AATTGCCATTCTAAATTCCATGCGAAAATGATTGGTGGACTTTTTCTTAACACTCTTAGTTTTGTAATTGTTAGTAACCA
TGTTATTGTTAATAACACAGCAAATGTGCATACTACACAACATGAAAATGTTATAGTACAACAGCATTAGGTTGTTAGTG
CTAGAACACAAAATTATTACCCAGAGTTCAGCATCGCTGTACTCTTTGTATCATTTTTGGCTTTGTACCGTAGTACAAAC
TTTAAGACGTGTGTCGGCATCTTAATGTTTAAGATTGTATCAATGACACTTGTAGGGCCTATGCTTATAGCATATGGTTA
CTACATTGATGGCATTGTTACAATAACTGTCTTAGCTTTAAGATTTTTCTACTTAGCATACTTTTGGTATGTTAATAGTA
GGTCCGAATTTATTTTATACAATACAACGACACTCATGTTTGTACATGGCAGAGCTGCACCGTTTATGAGAAGTTCTCAC
AGCTCTATTTATGTCACATTGTATGGTGGCATAAATTATATGTTTGTGAATGACCTCACGTTGCATTTTGTAGACCCTAT
GCTTGTAAGAATAGCAATACGTGGCTTAGCTCATGTCGATCTAACTGTTTTTAGAGCAGTTGAACTTCTCAATGGTGATT
TTATATATGTATTTTCACAGGAGCCCGTAGCCGGTGTTTACAATGCAGCCTCTTCTCAGGCGGTTCTAAACGAAATTGAC
TTAAAAGAAGAAGAAGAAGACCATAACTATGACGTTCCCTAGGGCATTTACTATCATAGATGACCATGGCATGGTTGTTA
GCGTCTTCTTCTGGCTCCTGTTGATAATTATATTGATATTGTTTTCAATAGCATTGCTAAATGTTATTAAATTGTGCATG
GTATGTTGCAATTTGGGTAAGACTATTATAGTACTACCTGCACGCCATGCATATGATGCCTATAAGACCTTTATGCAAAC
CAAGGCATATAATCCCGACGAAGCATTTTTGGTTTGAACTAAACAAAATGAAGTACATTTTGCTAATACTCGCGTGCATA
ATTGCATGCGTTTATGGTGAACGCTACTGTGCCATGCAAGACAGTGGCTTGCAGTGTATTAATGGCACAAATTCAAGATG
TCAAACCTGCTTTGAACGTGGTGATCTTATTTGGCATCTTGCTAACTGGAACTTCAGCTGGTCTGTAATATTGATTGTTT
TTATAACAGTGTTACAATATGGCAGACCACAATTTAGCTGGCTCGTTTATGGCATTAAAATGCTGATCATGTGGCTATTA
TGGCCTATTGTTCTAGCGCTTACGATTTTTAATGCATACTCTGAGTACCAAGTTTCCAGATATGTAATGTTCGGCTTTAG
TGTTGCAGGTGCAGTTGTAACGTTTGCACTTTGGATGATGTATTTTGTGAGATCTGTTCAGCTATATAGAAGAACCAAAT
CATGGTGGTCTTTTAATCCTGAGACTAATGCAATTCTTTGTGTTAATGCATTGGGTAGAAGTTATGTGCTTCCCTTAGAT
GGTACTCCTACAGGTGTTACCCTTACTCTACTTTCAGGAAATCTATATGCTGAAGGTTTCAAAATGGCTGGTGGTTTAAC
CATCGAGCATTTGCCTAAATACGTCATGATTGCTACACCTAGTAGAACCATCGTTTATACATTAGTTGGAAAACAATTAA
AAGCAACTACTGCCACAGGATGGGCTTACTACGTAAAATCTAAAGCTGGTGATTACTCAACAGAAGCACGTACTGACAAT
TTGAGTGAACATGAAAAATTATTACATATGGTGTAACTAAACTTTCAAATGGCCACACAGGGACAACGCGTCAACTGGGG
AGATGAACCTTCCAAAAGACGTGGTCGTTCTAACTCTCGTGGTCGGAAGAATAATGATATACCTTTGTCATTCTACAACC
CCATTACCCTCGAACAAGGATCTAAATTTTGGAATTTATGTCCGAGAGACCTTGTTCCCAAAGGAATAGGTAATAAGGAT
CAACAAATTGGTTATTGGAATAGACAGATTCGTTATCGTATTGTAAAAGGCCAGCGTAAGGAACTCGCTGAGAGGTGTT
CTTTTACTTCTTAGGTACAGGACCTCATGCTGATGCTAAATTCAAAGACAAGATTGATGGAGTCTTCTGGGTTGCAAGGG
ATGGTGCCATGAACAAGCCCACAACGCTTGGCACTCGTGGAACCAATAACGAATCCAAACCACTGAGATTTGATGGTAAG
ATACCGCCACAGTTTCAGCTTGAAGTGAACCGTTCTAGGAACAATTCAAGGTCTGGTTCTCAGTCTAGATCTGTTTCAAG
AAACAGATCTCAATCTAGAGGAAGACACCATTCCAATAACCAGAATAATAATGTTGAGGATACAATTGTAGCCGTGCTTG
AAAAATTAGGTGTTACTGACAAACAAAGGTCACGTTCTAAACCTAGAGAACGTAGTGATTCCAAACCTAGGGACACAACA
CCTAAGAATGCCAACAAACACACCTGGAAGAAAACTGCAGGCAAGGGAGATGTGACAACTTTCTATGGTGCTAGAAGTAG
TTCAGCTAACTTTGGTGATAGTGATCTCGTTGCCAATGGTAACGCTGCCAAATGCTACCCTCAGATAGCTGAATGTGTTC
CATCAGTGTCTAGCATAATCTTTGGCAGTCAATGGTCTGCTGAAGAAGCTGGTGATCAAGTGAAAGTCACGCTCACTCAC
ACCTACTACCTGCCAAAGGATGATGCCAAAACTAGTCAATTCCTAGAACAGATTGACGCTTACAAGCGACCTTCTGAAGT
GGCTAAGGATCAGAGGCAAAGAAGATCCCGTTCTAAGTCTGCTGATAAGAAGCCTGAGGAGTTGTCTGTAACTCTTGTGG
AGGCATACACAGATGTGTTTGATGACACACAGGTTGAGATGATTGATGAGGTTACGAACTAAACGCATGCTCGTTTTCGT
CCATGCTGTACTTGTAACAGCTTTAATCTTACTACTAATTGGTAGAATCCAATTACTAGAAAGGTTGTTACTCAGTCATC
TGCTTAATCTTACAACAGTCAGTAATGTTTTAGGTGTGCCTGACAGTAGTCTGCGTGTAAATTGTTTGCAGCTTTTGAAA
CCAGACTGCCTTGATTTTAATATCTTACATAAAGTTTTAGCAGAAACCAGGTTACTAGTAGTAGTACTGCGAGTGATCTT
TCTAGTTCTTCTAGGGTTTTCCTGCTATACATTGTTGGGTGCATTATTTTAACATCATGATTGTTGTAATCCTTGTGTGT
ATCTTTTTGGCTAATGGAATTAAAGCTACTGCTGTGCAAAATGACCTTCATGAACATCCCGTTCTTACCTGGGATTTATT
ACAGCATTTCATAGGACATACCCTCTACATTACAACACACCAGGTCTTAGCACTACCGCTTGGATCTCGTGTTGAGTGTG
AGGGTATCGAAGGTTTCAATTGCACATGGCCTGGCTTTCAAGATCCTGCACATGATCATATTGATTTCTACTTTGATCTT
TCTAATCCTTTCTATTCATTTGTAGATAATTTTTATATTGTAAGTGAGGGAAATCAAAGAATCAATCTCAGATTGGTTGG
```

Fig. 23, contd.

```
TGCTGTGCCAAAACAAAAGAGATTAAATGTTGGTTGTCATACATCATTTGCTGTTGATCTTCCATTTGGGATTCAGATAT
ACCATGACAGGGATTTTCAACACCCTGTTGATGGCAGACATCTAGATTGTACTCACAGAGTGTACTTTGTGAAGTACTGT
CCACATAACCTGCATGGTTATTGCTTTAATGAGAGGCTGAAAGTTTATGACTTGAAGCAATTCAGAAGCAAGAAGGTCTT
CGACAAAATCAACCAACATCATAAAACTGAGTTATAAGGCAACCCGATGTCTAAAACTGGTCTTTCCGAGGAATTACGGG
TCATCGCGCTGCCTACTCTTGTACAGAATGGTAAGCACGTGTAATAGGAGGTACAAGCAACCCTATTGCATATTAGGAAG
TTTAGATTTGATTTGGCAATGCTAGATTTAGTAATTTAGAGAAGTTTAAAGATCCGCTATGACGAGCCAACAATGGAAGA
GCTAACGTCTGGATCTAGTGATTGTTTAAAATGTAAAATTGTTTGAAAATTTTCCTTTTGATAGTGATACAAAAAAAAAA
AAAAAAAGCGGCCGCAAAATTCTTGAAGACGAAAGGGCCTCGTGATACGCCTATTTTTATAGGTTAATGTCATGATAATA
ATGGTTTCTTAGACGTCAGGTGGCACTTTTCGGGGAAATGTGCGCGGAACCCCTATTTGTTTATTTTTCTAAATACATTC
AAATATGTATCCGCTCATGAGACAATAACCCTGATAAATGCTTCAATAATATTGAAAAAGGAAGAGTATGAGTATTCAAC
ATTTCCGTGTCGCCCTTATTCCCTTTTTTGCGGCATTTTGCCTTCCTGTTTTTGCTCACCCAGAAACGCTGGTGAAAGTA
AAAGATGCTGAAGATCAGTTGGGTGCACGAGTGGGTTACATCGAACTGGATCTCAACAGCGGTAAGATCCTTGAGAGTTT
TCGCCCCGAAGAACGTTTTCCAATGATGAGCACTTTTAAAGTTCTGCTATGTGGCGCGGTATTATCCCGTGTTGACGCCG
GGCAAGAGCAACTCGGTCGCCGCATACACTATTCTCAGAATGACTTGGTTGAGTACTCACCAGTCACAGAAAAGCATCTT
ACGGATGGCATGACAGTAAGAGAATTATGCAGTGCTGCCATAACCATGAGTGATAACACTGCGGCCAACTTACTTCTGAC
AACGATCGGAGGACCGAAGGAGCTAACCGCTTTTTTGCACAACATGGGGGATCATGTAACTCGCCTTGATCGTTGGGAAC
CGGAGCTGAATGAAGCCATACCAAACGACGAGCGTGACACCACGATGCCTGCAGCAATGGCAACAACGTTGCGCAAACTA
TTAACTGGCGAACTACTTACTCTAGCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGAGCGTGGGTCTCGCGGTATCATTG
CAGCACTGGGGCCAGATGGTAAGCCCTCCCGTATCGTAGTTATCTACACGACGGGGAGTCAGGCAACTATGGATGAACGA
AATAGACAGATCGCTGAGATAGGTGCCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTGATAATCTCATGACCAAAATCCCTT
AACGTGAGTTTTCGTTCCACTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAGCTACCAACTCTTTT
TCCGAAGGTAACTGGCTTCAGCAGAGCGCAGATACCAAATACTGTCCTTCTAGTGTAGCCGTAGTTAGGCCACCACTTCA
AGAACTCTGTAGCACCGCCTACATACCTCGCTCTGCTAATCCTGTTACCAGTGGCTGCTGCCAGTGGCGATAAGTCGTGT
CTTACCGGGTTGGACTCAAGACGATAGTTACCGGATAAGGCGCAGCGGTCGGGCTGAACGGGGGGTTCGTGCACACAGCC
CAGCTTGGAGCGAACGACCTACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATTTTTGTGATGCTCGTCAGGGGGGCGGAGCCT
ATGGAAAAACGCCAGCAACGCGGCCTTTTTACGGTTCCTGGCCTTTTGCTGGCCTTTTGCTCACATGTTCTTTCCTGCGT
TATCCCCTGATTCTGTGGATAACCGTATTACCGCCTTTGAGTGAGCTGATACCGCTCGCCGCAGCCGAACGACCGAGCGC
AGCGAGTCAGTGAGCGAGGAAGCGGAAGAGCGCCTGATGCGGTATTTTCTCCTTACGCATCTGTGCGGTATTTCACACCG
CATATGGTGCACTCTCAGTACAATCTGCTCTGATGCCGCATAGTTAAGCCAGTATACACTCCGCTATCGCTACGTGACTG
GGTCATGGCTGCGCCCCGACACCCGCCAACACCCGCTGACGCGCCCTGACGGGCTTGTCTGCTCCCGGCATCCGCTTACA
GACAAGCTGTGACCGTCTCCGGGAGCTGCATGTGTCAGAGGTTTTCACCGTCATCACCGAAACGCGCGAGGCAGCTGCGG
TAAAGCTCATCAGCGTGGTCGTGAAGCGATTCACAGATGTCTGCCTGTTCATCCGCGTCCAGCTCGTTGAGTTTCTCCAG
AAGCGTTAATGTCTGGCTTCTGATAAAGCGGGCCATGTTAAGGGCGGTTTTTTCCTGTTTGGTCACTGATGCCTCCGTGT
AAGGGGGATTTCTGTTCATGGGGGTAATGATACCGATGAAACGAGAGAGGATGCTCACGATACGGGTTACTGATGATGAA
CATGCCCGGTTACTGGAACGTTGTGAGGGTAAACAACTGGCGGTATGGATGCGGCGGGACCAGAGAAAAATCACTCAGGG
TCAATGCCAGCGCTTCGTTAATACAGATGTAGGTGTTCCACAGGGTAGCCAGCAGCATCCTGCGATGCAGATCCGGAACA
TAATGGTGCAGGGCGCTGACTTCCGCGTTTCCAGACTTTACGAAACACGGAAACCGAAGACCATTCATGTTGTTGCTCAG
GTCGCAGACGTTTTGCAGCAGCAGTCGCTTCACGTTCGCTCGCGTATCGGTGATTCATTCTGCTAACCAGTAAGGCAACC
CCGCCAGCCTAGCCGGGTCCTCAACGACAGGAGCACGATCATGCGCACCCGTGGCCAGGACCCAACGCTGCCCGAGATGC
GCCGCGTGCGGCTGCTGGAGATGGCGGACGCGATGGATATGTTCTGCCAAGGGTTGGTTTGCGCATTCACAGTTCTCCGC
AAGAATTGATTGGCTCCAATTCTTGGAGTGGTGAATCCGTTAGCGAGGTGCCGCCGGCTTCCATTCAGGTCGAGGTGGCC
CGGCTCCATGCACCGCGACGCAACGCGGGGAGGCAGACAAGGTATAGGGCGGCGCCTACAATCCATGCCAACCCGTTCCA
TGTGCTCGCCGAGGCGGCATAAATCGCCGTGACGATCAGCGGTCCAGTGATCGAAGTTAGGCTGGTAAGAGCCGCGAGCG
ATCCTTGAAGCTGTCCCTGATGGTCGTCATCTACCTGCCTGGACAGCATGGCCTGCAACGCGGGCATCCCGATGCCGCCG
GAAGCGAGAAGAATCATAATGGGGAAGGCCATCCAGCCTCGCGTCGCGAACGCCAGCAAGACGTAGCCCAGCGCGTCGGC
CGCCATGCCGGCGATAATGGCCTGCTTCTCGCCGAAACGTTTGGTGGCGGGACCAGTGACGAAGGCTTGAGCGAGGGCGT
GCAAGATTCCGAATACCGCAAGCGACAGGCCGATCATCGTCGCGCTCCAGCGAAAGCGGTCCTCGCCGAAAATGACCCAG
AGCGCTGCCGGCACCTGTCCTACGAGTTGCATGATAAAGAAGACAGTCATAAGTGCGGCGACGATAGTCATGCCCCGCGC
CCACCGGAAGGAGCTGACTGGGTTGAAGGCTCTCAAGGGCATCGGTCGACGCTCTCCCTTATGCGACTCCTGCATTAGGA
AGCAGCCCAGTAGTAGGTTGAGGCCGTTGAGCACCGCCGCCGCAAGGAATGGTGCATGCAAGGAGATGGCGCCCAACAGT
CCCCCGGCCACGGGGCCTGCCACCATACCCACGCCGAAACAAGCGCTCATGAGCCCGAAGTGGCGAGCCCGATCTTCCCC
ATCGGTGATGTCGGCGATATAGGCGCCAGCAACCGCACCTGTGGCGCCGGTGATGCCGGCCACGATGCGTCCGGCGTAGA
GGATCCACAGGACGGGTGTGGTCGCCATGATCGCGTAGTCGATAGTGGCTCCAAGTAGCGAAGCGAGCAGGACTGGGCGG
CGGCCAAAGCGGTCGGACAGTGCTCCGAGAACGGGTGCGCATAGAAATTGCATCAACGCATATAGCGCTAGCAGCACGCC
ATAGTGACTGGCGATGCTGTCGGAATGGACGATCCG
```

Fig. 24

Addendum 2: DNA sequence pBRDI2

```
CTCGAGTCGAAATTAATACGACTCACTATAGGGTTTTTAAAGTAAAGTGAGTGTAGCGTGGCTATAACTCTTCTTTTACT
TTAACTAGCCTTGTGCTAGATTTGTCTTCGGACACCAACTCGAACTAAACGAAATATTTGTCTCTCTATGAAACCATAGA
AGACAAGCGTTGATTATTTCACCAGTTTGGCAATCACTCCTAGGAACGGGGTTGAGAGAACGGCGCACCAGGGTTCCGTC
CCTGTTTGGTAAGTCGTCTAGTATTAGCTGCGGCGGTTCCGCCCGTCGTAGTTGGGTAGACCGGGTTCCGTCCTGTGATC
TCCCTCGCCGGCCGCCAGGAGAATGAGTTCCAAACAATTTAAGATCCTCGTTAATGAGGACTACCAAGTCAACGTTCCTA
GCCTTCCTTTCCGTGACGCACTGCAGGAAATTAAGTACTGCTACCGTAACGGTTTTGATGGCTATGTCTTCGTGCCTGAA
TACCGTCGTGACCTAGTTGATTGCAATCGTAAGGATCACTACGTCATTGGTGTTTTGGGTAACGGAATAAGTGATCTTAA
ACCTGTTCTCCTTACCGAACCTTCCGTCATGTTGCAGGGTTTCATTGTTAGAGCCAACTGCAATGGCGTTCTTGAGGACT
TTGACCTTAAATTCGCCCGTACTGGAAACGGCGCCATATATGTGGACCAATACATGTGTGGTGCTGATGGAAAGCCAGTT
ATTGAAGGTGAGCTCTGGACTGTGTTTTGTACAAGTGTTAATACGTCATCATCAGAAGGTTTTCTGATTGGTATTAACTA
CTTAGGACCATACTGTGACAAAGCAATAGTAGATGGAAATATAATGCATGCCAATTATATATTTTGGAGAAACTCTACAA
TTATGGCTCTATCACATAACTCAGTCCTAGACACTCCAAAATTTAAGTGCCGTTGTAACAATGCACTTATTGTTAATTTA
AAAGAAAAAGAATTGAATGAAATGGTCGTTGGATTACTAAGGAAGGGTAAGTTACTCATTAGAAATAATGGCAAGCTACT
AAACTTTGGTAATCATTTAGTTAATGTGCCATGCTGTTCGTGTTTATTCTATTTTTGCCCTCTTGTTTAGGGTATATTGG
TGATTTTAGATGTATCCAGCTTGTGAATTCAAACGGTGCTAATGTTAGTGCTCCAAGCATTAGCACTGAGACCGTTGAAG
TTTCACAAGGCCTGGGGACATATTATGTGTTAGATCGAGTTTATTTAAATGCCACATTATTGCTTACTGGTTACTACCCG
GTCGATGGTTCTAAGTTTAGAAACCTCGCTCTTAGGGGAACTAACTCAGTTAGCTTGTCGTGGTTTCAACCACCCTATTT
AAATCAGTTTAATGATGGCATATTTGCGAAGGTGCAGAACCTTAAGACAAGTACGCCATCAGGTGCAACTGCATATTTTC
CTACTATAGTTATAGGTAGTTTGTTTGGCTATACTTCCTATACCGTTGTAATAGAGCCATATAATGGTGTTATAATGGCC
TCAGTGTGCCAGTATACCATTTGTCAGTTACCTTACACTGATTGTAAGCCTAACACTAATGGTAATAAGCTTATAGGGTT
TTGGCACACGGATGTAAAACCCCCAATTTGTGTGTTAAAGCGAAATTTCACGCTTAATGTTAATGCTGATGCATTTTATT
TTCATTTTTACCAACATGGTGGTACTTTTTATGCGTACTATGCGGATAAACCCTCCGCTACTACGTTTTGTTTAGTGTA
TATATTGGCGATATTTTAACACAGTATTATGTGTTACCTTTCATCTGCAACCCAACAGCTGGTAGCACTTTTGCTCCGCG
CTATTGGGTTACACCTTTGGTTAAGCGCCAATATTTGTTTAATTTCAACCAGAAGGGTGTCATTACTAGTGCTGTTGATT
GTGCTAGTAGTTATACCAGTGAAATAAAATGTAAGACCCAGAGCATGTTACCTAGCACTGGTGTCTATGAGTTATCCGGT
TATACGGTCCAACCAGTTGGAGTTGTATACCGGCGTGTTGCTAACCTCCCAGCTTGTAATATAGAGGAGTGGCTTACTGC
TAGGTCAGTCCCCTCCCCTCTCAACTGGGAGCGTAAGACTTTTCAGAATTGTAATTTTAATTTAAGCAGCCTGTTACGTT
ATGTTCAGGCTGAGAGTTTGTTTTGTAATAATATCGATGCTTCCAAAGTGTATGGCAGGTGCTTTGGTAGTATTTCAGTT
GATAAGTTTGCTGTACCCGAAGTAGGCAAGTTGATTTACAGCTTGGTAACTCTGGATTTCTGCAGACTGCTAATTATAA
GATTGATACAGCTGCCACTTCGTGTCAGCTGCATTACACCTTGCCTAAGAATAATGTCACCATAAACAACCATAACCCCT
CGTCTTGGAATAGGAGGTATGGCTTTAATGATGCTGGCGTCTTTGGCAAAAACCAACATGACGTTGTTTACGCTCAGCAA
TGTTTTACTGTAAGATCTAGTTATTGCCCGTGTGCTCAACCGGACATAGTTAGCCCTTGCACTACTCAGACTAAGCCTAA
GTCTGCTTTTGTTAATGTGGGTGACCATTGTGAAGGCTTAGGTGTTTTAGAAGATAATTGTGGCAATGCTGATCCACATA
AGGGTTGTATCTGTGCCAACAATTCATTTATTGGATGGTCACATGATACCTGCCTTGTTAATGATCGCTGCCAAATTTTT
GCTAATATATTGTTAAATGGCATTAATAGTGGTACCACATGTTCCACAGATTTGCAGTTGCCTAATACTGAAGTGGTTAC
TGGCATTTGTGTCAAATATGACCTCTACGGTATTACTGGACAAGGTGTTTTTAAAGAGGTTAAGGCTGACTATTATAATA
GCTGGCAAACCCTTCTGTATGATGTTAATGGTAATTTGAATGGTTTTCGTGATCTTACCACTAACAAGACTTATACGATA
AGGAGCTGTTATAGTGGCCGTGTTTCTGCTGCATTTCATAAAGATGCACCCGAACCGGCTCTGCTCTATCGTAATATAAA
TTGTAGCTATGTTTTTAGCAATAATATTTCCCGTGAGGAGAACCCACTTAATTACTTTGATAGTTATTTGGGTTGTGTTG
TTAATGCTGATAACCGCACGGATGAGGCGCTTCCTAATTGTGATCTCCGTATTGGGTGCTGGCTTATGCGTTGATTATCA
AAATCACGCAGGGCTCACCGATCAGTTTCTACTGGCTATCGGTTAACTACATTTGAGCCATACATCCGATGTTAGTTAA
TGATAGTGTCCAATCCGTTGATGGATTATATGAGATGCAAATACCAACCAATTTTACTATTGGGCACCATGAGGAGTTCA
TTCAAACTAGATCTCCAAAGGTGACTATAGATTGTGCTGCATTTGTCTGTGGTGATAACACTGCATGCAGGCAGCAGTTG
GTTGAGTATGGCTCTTTCTGTGTTAATGTTAATGCCATTCTTAATGAGGTTAATAACCTCTTGGATAATATGCAACTACA
AGTTGCTAGTGCATTAATGCAGGGTGTTACTATAAGCTCGAGACTGCCAGACGGCATCTCAGGCCCTATAGATGACATTA
ATTTTAGTCCTCTACTTGGATGCATAGGTTCAACATGTGCTGAAGACGGCAATGGACCTAGTGCAATCGAGGGCGTTCT
GCTATAGAGGATTTGTTATTTGACAAGGTCAAATTATCTGATGTTGGCTTTGTCGAGGCTTATAATAATTGCACCGGTGG
TCAAGAAGTTCGTGACCTCCTTTGTGTACAATCTTTTAATGGCATCAAAGTATTACCTCCTGTGTTGTCAGAGAGTCAGA
TCTCTGGCTACACAACCGGTGCTACTGCGGCAGCTATGTTCCCACCGTGGTCAGCAGCTGCCGGTGTGCCATTTAGTTTA
AGTGTTCAATATAGAATTAATGGTTTAGGTGTCACTATGAATGTGCTTAGTGAGAACCAAAAGATGATTGCTAGTGCTTT
TAACAATGCGCTGGGTGCTATCCAGGATGGGTTTGATGCAACCAATTCTGCTTTAGGTAAGATCCAGTCCGTTGTTAATG
CAAATGCTGAAGCACTCAATAACTTACTAAATCAGCTTTCTAACAGGTTTGGTGCTATTAGTGCTTCTTTACAAGAAATT
CTAACTCGGCTTGAGGCTGTAGAAGCAAAAGCCCAGATAGATCGTCTTATTAATGGCAGGTTAACTGCACTTAATGCGTA
TATATCCAAGCAACTTAGTGATAGTACGCTTATTAAAGTTAGTGCTGCTCAGGCCATAGAAAAGGTCAATGAGTGCGTTA
AGAGCCAAACCACGCGTATTAATTTCTGTGGCAATGGTAATCATATATTATCTCTTGTCCAGAATGCGCCTTATGGCTTA
TATTTTATACACTTCAGCTATGTGCCAATATCCTTTACAACCGCAAATGTGAGTCCTGGACTTTGCATTTCTGGTGATAG
AGGATTAGCACCTAAAGCTGGATATTTTGTTCAAGATGATGGAGAATGGAAGTTCACAGGCAGTTCATATTACTACCCTG
AACCCATTACAGATAAAAACAGTGTCATTATGAGTAGTTGCGCAGTAAACTACACAAAGGCACCTGAAGTTTTCTTGAAC
ACTTCAATACCTAATCCACCCGACTTTAAGGAGGAGTTAGATAAATGGTTTAAGAATCAGACGTCTATTGCGCCTGATTT
```

Fig. 24, contd.

```
ATCTCTCGATTTCGAGAAGTTAAATGTTACTTTGCTGGACCTGACGTATGAGATGAACAGGATTCAGGATGCAATTAAGA
AGTTAAATGAGAGCTACATCAACCTCAAGGAAGTTGGCACATATGAAATGTATGTGAAATGGCCTTGGTATGTGTGGCTA
CTGATAGGTTTAGTAGTAGTATTTTGCATACCATTACTGCTATTTTGCTGTTTTAGCACAGGTTGTTGTGGATGCATAGG
TTGTTTAGGAAGTTGTTGTCACTCTATATGTAGTAGAAGACAATTTGAAAATTATGAACCAATTGAAAAAGTGCATGTCC
ACTAAATTTAAAGTTAAGGATGTTGAATAAATTCCTTAAGAACTAAACTTATTAGTCATTACAGGTCTTGTATGGACATT
GTCAAATCTATTGACATATTCGTAGACGCTGTACTTGACGAACTTGACCGTGCATACTTTGCTGTAACTCTTAAAGTAGA
ATTTAAGACTGGTAAACTACTTGTGTGTATAGGTTTTGGTGACACACTTCTTGAGGCTAAGGACAAAGCGTATGCTAAGC
TTGGTCTCTCCTTTATTGAAGAAGTCAATAGTCATACAGTTGTTTAGTATTACTGTTTACAAGTTTAAAGCCAAATTTTG
GTATAAACTACCTTTTGAAACTAGACTTTGTATCATTAAACACACAAGACCCAAAGCATTAAGTGTTACAAAACAAGTAA
AGAGAGATTATAGAAAAATTGCCATTCTAAATTCCATGCGAAAATGATTGGTGGACTTTTTCTTAACACTCTTAGTTTTG
TAATTGTTAGTAACCATGTTATTGTTAATAACACAGCAAATGTGCATACTACACAACATGAAATGTTATAGTACAACAG
CATTAGGTTGTTAGTGCTAGAACACAAAATTATTACCCAGAGTTCAGCATCGCTGTACTCTTTGTATCATTTTTGGCTTT
GTACCGTAGTACAAACTTTAAGACGTGTGTCGGCATCTTAATGTTTAAGATTGTATCAATGACACTGTAGGGCCTATGC
TTATAGCATATGGTTACTACATTGATGGCATTGTTACAATAACTGTCTTAGCTTTAAGATTTTTCTACTTAGCATACTTT
TGGTATGTTAATAGTAGGTCCGAATTTATTTTATACAATACAACGACACTCATGTTTGTACATGGCAGAGCTGCACCGTT
TATGAGAAGTTCTCACAGCTCTATTTATGTCACATTGTATGGTGGCATAAATTATATGTTTGTGAATGACCTCACGTTGC
ATTTTGTAGACCCTATGCTTGTAAGAATAGCAATACGTGGCTTAGCTCATGCTGATCTAACTGTTTTAGAGCAGTTGAA
CTTCTCAATGGTGATTTTATATATGTATTTTCACAGGAGCCCGTAGCCGGTGTTTACAATGCAGCCTCTTCTCAGGCGGT
TCTAAACGAAATTGACTTAAAAGAAGAAGAAGAAGACCATAACTATGACGTTCCCTAGGGCATTTACTATCATAGATGAC
CATGGCATGGTTGTTAGCGTCTTCTTCTGGCTCCTGTTGATAATTATATTGATATTGTTTCAATAGCATTGCTAAATGT
TATTAAATTGTGCATGGTATGTTGCAATTTGGGTAAGACTATTATAGTACTACCTGCACGCCATGCATATGATGCCTATA
AGACCTTTATGCAAACCAAGGCATATAATCCCGACGAAGCATTTTTGGTTTGAACTAAACAAAATGAAGTACATTTTGCT
AATACTCGCGTGCATAATTGCATGCGTTTATGGTGAACGCTACTGTGCCATGCAAGACAGTGGCTTGCAGTGTATTAATG
GCACAAATTCAAGATGTCAAACCTGCTTTGAACGTGGTGATCTTATTTGGCATCTTGCTAACTGGAACTTCAGCTGGTCT
GTAATATTGATTGTTTTTATAACAGTGTTACAATATGGCAGACCACAATTTAGCTGGCTCGTTTATGGCATTAAAATGCT
GATCATGTGGCTATTATGGCCTATTGTTCTAGCGCTTACGATTTTTAATGCATACTCTGAGTACCAAGTTTCCAGATATG
TAATGTTCGGCTTTAGTGTTGCAGGTGCAGTTGTAACGTTTGCACTTTGGATGATGTATTTTGTGAGATCTGTTCAGCTA
TATAGAAGAACCAAATCATGGTGGTCTTTTAATCCTGAGACTAATGCAATTCTTTGTGTTAATGCATTGGGTAGAAGTTA
TGTGCTTCCCTTAGATGGTACTCCTACAGGTGTTACCCTTACTCTACTTTCAGGAAATCTATATGCTGAAGGTTTCAAAA
TGGCTGGTGGTTTAACCATCGAGCATTTGCCTAAATACGTCATGATTGCTACACCTAGTAGAACCATCGTTTATACATTA
GTTGGAAAACAATTAAAAGCAACTACTGCCACAGGATGGGCTTACTACGTAAAATCTAAAGCTGGTGATTACTCAACAGA
AGCACGTACTGACAATTTGAGTGAACATGAAAAATTATTACATATGGTGTAACTAAACTTTCAAATGGCCACACAGGGAC
AACGCGTCAACTGGGGAGATGAACCTTCCAAAAGACGTGGTCGTTCTAACTCTCGTGGTCGGAAGAATAATGATATACCT
TTGTCATTCTACAACCCCATTACCCTCGAACAAGGATCTAAATTTTGGAATTTATGTCCGAGAGACCTTGTTCCCAAAGG
AATAGGTAATAAGGATCAACAAATTGGTTATTGGAATAGACAGATTCGTTATCGTATTGTAAAAGGCCAGCGTAAGGAAC
TCGCTGAGAGGTGGTTCTTTTACTTCTTAGGTACAGGACCTCATGCTGATGCTAAATTCAAAGACAAGATTGATGGAGTC
TTCTGGGTTGCAAGGGATGGTGCCATGAACAAGCCCACAACGCTTGGCACTCGTGGAACCAATAACGAATCCAAACCACT
GAGATTTGATGGTAAGATACCGCCACAGTTTCAGCTTGAAGTGAACCGTTCTAGGAACAATTCAAGGTCTGGTTCTCAGT
CTAGATCTGTTTCAAGAAACAGATCTCAATCTAGAGGAAGACACCATTCCAATAACCAGAATAATAATGTTGAGGATACA
ATTGTAGCCGTGCTTGAAAAATTAGGTGTTACTGACAAACAAAGGTCACGTTCTAAACCTAGAGAACGTAGTGATTCAA
ACCTAGGGACACAACACCTAAGAATGCCAACAAACACACCTGGAAGAAAACTGCAGGCAAGGGAGATGTGACAACTTTCT
ATGGTGCTAGAAGTAGTTCAGCTAACTTTGGTGATAGTGATCTCGTTGCCAATGGTAACGCTGCCAAATGCTACCCTCAG
ATAGCTGAATGTGTTCCATCAGTGTCTAGCATAATCTTTGGCAGTCAATGGTCTGCTGAAGAAGCTGGTGATCAAGTGAA
AGTCACGCTCACTCACACCTACTACCTGCCAAAGGATGATGCCAAAACTAGTCAATTCCTAGAACAGATTGACGCTTACA
AGCGACCTTCTGAAGTGGCTAAGGATCAGAGGCAAAGAAGATCCCGTTCTAAGTCTGCTGATAAGAAGCCTGAGGAGTTG
TCTGTAACTCTTGTGGAGGCATACACAGATGTGTTTGATGACACACAGGTTGAGATGATTGATGAGGTTACGAACTAAAC
GCATGCTCGTTTCGTCCATGCTGTACTTGTAACAGCTTTAATCTTACTACTAATTGGTAGAATCCAATTACTAGAAAGG
TTGTTACTCAGTCATCTGCTTAATCTTACAACAGTCAGTAATGTTTTAGGTGTGCCTCAGCAGTCTGCGTGTAATTG
TTTGCAGCTTTTGAAACCAGACTGCCTTGATTTTAATATCTTACATAAAGTTTAGCAGAAACCAGGTTACTAGTAGTAG
TACTGCGAGTGATCTTTCTTCTAGGGTTTTCCTGCTATACATTGTTGGGTGCATTATTTTAACATCATGATTGT
TGTAATCCTTGTGTATCTTTTTGGCTAATGGAATTAAAGCTACTGCTGTGCAAAATGACCTTCATGAACATCCCGTTC
TTACCTGGGATTTATTACAGCATTTCATAGGACATACCCTCTACATTACAACACACCAGGTCTTAGCACTACCGCTTGGA
TCTCGTGTTGAGTGTGAGGGTATCGAAGGTTTCAATTGCACATGGCCTGGCTTTCAAGATCCTGCACATGATCATATTGA
TTTCTACTTTGATCTTTCTAATCCTTTCTATTCATTTGTAGATAATTTTTATATTGTAAGTGAGGGAAATCAAAGAATCA
ATCTCAGATTGGTTGGTGCTGTGCCAAAACAAAAGAGATTAAATGTTGGTTGTCATACATCATTTGCTGTTGATCTTCCA
TTTGGGATTCAGATATACCATGACAGGGATTTTCAACACCCTGTTGATGGCAGACATCTAGATTGTACTCACAGAGTGTA
CTTTGTGAAGTACTGTCCACATAACCTGCATGGTTATTGCTTTAATGAGAGGCTGAAAGTTTATGACTTGAAGCAATTCA
GAAGCAAGAAGGTCTTCGACAAAATCAACCAACATCATAAAACTGAGTTATAAGGCAACCCGATGTCTAAAACTGGTCTT
TCCGAGGAATTACGGGTCATCGCGCTGCCTACTCTTGTACAGAATGGTAAGCACGTGTAATAGGAGGTACAAGCAACCCT
ATTGCATATTAGGAAGTTTAGATTTGATTTGGCAATGCTAGATTTAGTAATTTAGAGAAGTTTAAAGATCCGCTATGACG
AGCCAACAATGGAAGAGCTAACGTCTGGATCTAGTGATTGTTTAAAATGTAAAATTGTTTGAAAATTTTCCTTTTGATAG
TGATACAAAAAAAAAAAAAAAAAGCGGCCGCAAAATTCTTGAAGACGAAAGGGCCTCGTGATACGCCTATTTTTATAGGT
```

Fig. 24, contd.

```
TAATGTCATGATAATAATGGTTTCTTAGACGTCAGGTGGCACTTTTCGGGGAAATGTGCGCGGAACCCCTATTTGTTTAT
TTTTCTAAATACATTCAAATATGTATCCGCTCATGAGACAATAACCCTGATAAATGCTTCAATAATATTGAAAAAGGAAG
AGTATGAGTATTCAACATTTCCGTGTCGCCCTTATTCCCTTTTTTGCGGCATTTTGCCTTCCTGTTTTTGCTCACCCAGA
AACGCTGGTGAAAGTAAAAGATGCTGAAGATCAGTTGGGTGCACGAGTGGGTTACATCGAACTGGATCTCAACAGCGGTA
AGATCCTTGAGAGTTTTCGCCCCGAAGAACGTTTTCCAATGATGAGCACTTTTAAAGTTCTGCTATGTGGCGCGGTATTA
TCCCGTGTTGACGCCGGGCAAGAGCAACTCGGTCGCCGCATACACTATTCTCAGAATGACTTGGTTGAGTACTCACCAGT
CACAGAAAAGCATCTTACGGATGGCATGACAGTAAGAGAATTATGCAGTGCTGCCATAACCATGAGTGATAACACTGCGG
CCAACTTACTTCTGACAACGATCGGAGGACCGAAGGAGCTAACCGCTTTTTTGCACAACATGGGGGATCATGTAACTCGC
CTTGATCGTTGGGAACCGGAGCTGAATGAAGCCATACCAAACGACGAGCGTGACACCACGATGCCTGCAGCAATGGCAAC
AACGTTGCGCAAACTATTAACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGCATTGGTAACTGTCAGACCAAGTTT
ACTCATATATACTTTAGATTGATTTAAAACTTCATTTTTAATTTAAAAGGATCTAGGTGAAGATCCTTTTTGATAATCTC
ATGACCAAAATCCCTTAACGTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTGGTTTGTTTGCCGGATCAAG
AGCTACCAACTCTTTTTCCGAAGGTAACTGGCTTCAGCAGAGCGCAGATACCAAATACTGTCCTTCTAGTGTAGCCGTAG
TTAGGCCACCACTTCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGGAGAGCGCACGAGGGAGCTTCC
AGGGGGAAACGCCTGGTATCTTTATAGTCCTGTCGGGTTTCGCCACCTCTGACTTGAGCGTCGATTTTTGTGATGCTCGT
CAGGGGGCGGAGCCTATGGAAAAACGCCAGCAACGCGGCCTTTTTACGGTTCCTGGCCTTTTGCTGGCCTTTTGCTCAC
ATGTTCTTTCCTGCGTTATCCCCTGATTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCTGATGCGGTATTTTCTCCTTACGCATCTGT
GCGGTATTTCACACCGCATATGGTGCACTCTCAGTACAATCTGCTCTGATGCCGCATAGTTAAGCCAGTATACACTCCGC
TATCGCTACGTGACTGGGTCATGGCTGCGCCCCGACACCCGCCAACACCCGCTGACGCGCCCTGACGGGCTTGTCTGCTC
CCGGCATCCGCTTACAGACAAGCTGTGACCGTCTCCGGGAGCTGCATGTGTCAGAGGTTTTCACCGTCATCACCGAAACG
CGCGAGGCAGCTGCGGTAAAGCTCATCAGCGTGGTCGTGAAGCGATTCACAGATGTCTGCCTGTTCATCCGCGTCCAGCT
CGTTGAGTTTCTCCAGAAGCGTTAATGTCTGGCTTCTGATAAAGCGGGCCATGTTAAGGGCGGTTTTTTCCTGTTTGGTC
ACTGATGCCTCCGTGTAAGGGGATTTCTGTTCATGGGGGTAATGATACCGATGAAACGAGAGAGGATGCTCACGATACG
GGTTACTGATGATGAACATGCCCGGTTACTGGAACGTTGTGAGGGTAAACAACTGGCGGTATGGATGCGGCGGGACCAGA
GAAAAATCACTCAGGGTCAATGCCAGCGCTTCGTTAATACAGATGTAGGTGTTCCACAGGGTAGCCAGCAGCATCCTGCG
ATGCAGATCCGGAACATAATGGTGCAGGGCGCTGACTTCCGCGTTTCCAGACTTTACGAAACACGGAAACCGAAGACCAT
TCATGTTGTTGCTCAGGTCGCAGACGTTTTGCAGCAGCAGTCGCTTCACGTTCGCTCGCGTATCGGTGATTCATTCTGCT
AACCAGTAAGGCAACCCCGCCAGCCTAGCCGGGTCCTCAACGACAGGAGCACGATCATGCGCACCCGTGGCCAGGACCCA
ACGCTGCCCGAGATGCGCCGCGTGCGGCTGCTGGAGATGGCGGACGCGATGGATATGTTCTGCCAAGGGTTGGTTTGCGC
ATTCACAGTTCTCCGCAAGAATTGATTGGCTCCAATTCTTGGAGTGGTGAATCCGTTAGCGAGGTGCCGCCGGCTTCCAT
TCAGGTCGAGGTGGCCCGGCTCCATGCACCGCGACGCAACGCGGGGAGGCAGACAAGGTATAGGGCGGCGCCTACAATCC
ATGCCAACCCGTTCCATGTGCTCGCCGAGGCGGCATAAATCGCCGTGACGATCAGCGGTCCAGTGATCGAAGTTAGGCTG
GTAAGAGCCGCGAGCGATCCTTGAAGCTGTCCCTGATGGTCGTCATCTACCTGCCTGGACAGCATGGCCTGCAACGCGGG
CATCCCGATGCCGCCGGAAGCGAGAAGAATCATAATGGGGAAGGCCATCCAGCCTCGCGTCGCGAACGCCAGCAAGACGT
AGCCCAGCGCGTCGGCCGCCATGCCGGCGATAATGGCCTGCTTCTCGCCGAAACGTTTGGTGGCGGGACCAGTGACGAAG
GCTTGAGCGAGGGCGTGCAAGATTCCGAATACCGCAAGCGACAGGCCGATCATCGTCGCGCTCCAGCGAAAGCGGTCCTC
GCCGAAAATGACCCAGAGCGCTGCCGGCACCTGTCCTACGAGTTGCATGATAAAGAAGACAGTCATAAGTGCGGCGACGA
TAGTCATGCCCCGCGCCCACCGGAAGGAGCTGACTGGGTTGAAGGCTCTCAAGGGCATCGGTCGACGCTCTCCCTTATGC
GACTCCTGCATTAGGAAGCAGCCCAGTAGTAGGTTGAGGCCGTTGAGCACCGCCGCCAAGGAATGGTGCATGCAAGGA
GATGGCGCCCAACAGTCCCCCGGCCACGGGGCCTGCCACCATACCACGCCGAAACAAGCGCTCATGAGCCCGAAGTGGC
GAGCCCGATCTTCCCCATCGGTGATGTCGGCGATATAGGCGCCAGCAACCGCACCTGTGGCGCCGGTGATGCCGGCCACG
ATGCGTCCGGCGTAGAGGATCCACAGGACGGGTGTGGTCGCCATGATCGCGTAGTCGATAGTGGCTCCAAGTAGCGAAGC
GAGCAGGACTGGGCGGCGGCCAAAGCGGTCGGACAGTGCTCCGAGAACGGGTGCGCATAGAAATTGCATCAACGCATATA
GCGCTAGCAGCACGCCATAGTGACTGGCGATGCTGTCGGAATGGACGATCCGCTCGA
```

FIG. 25

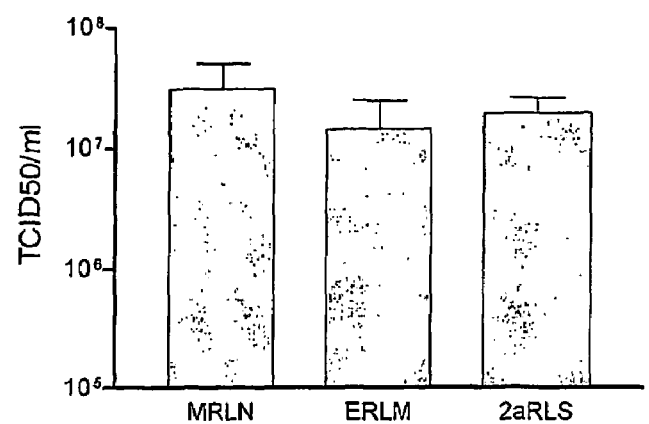
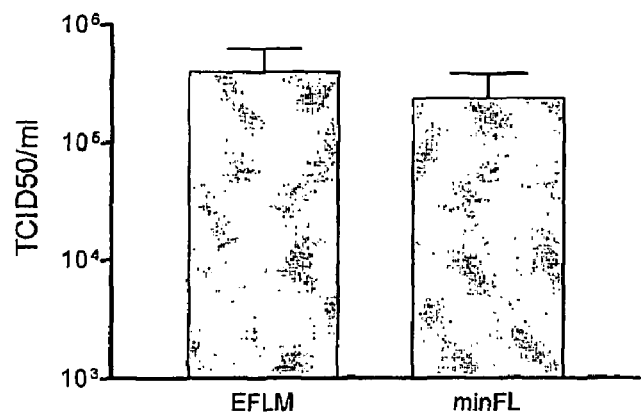
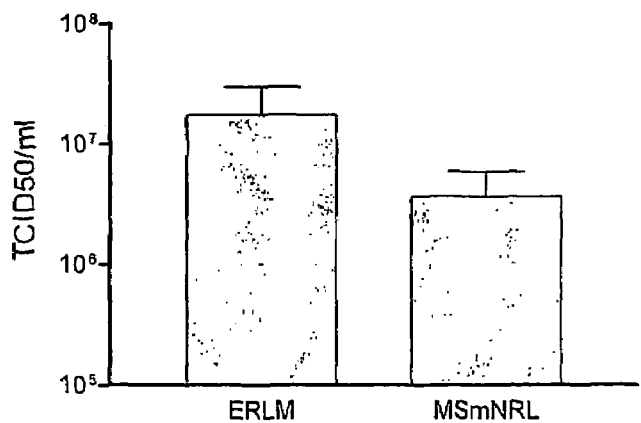
Fig. 32

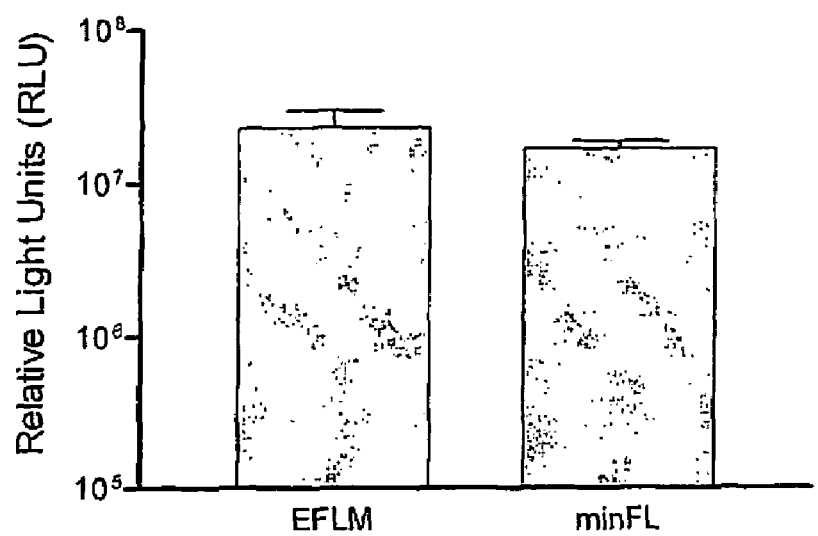
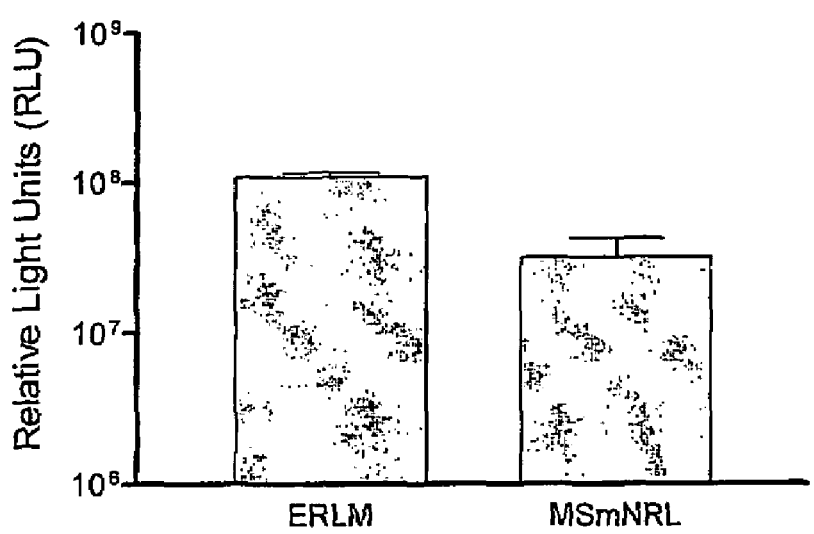
Fig. 33

Fig. 35: Pathogenicity of the deletion mutants of FIPV

— FIPV 79-1146
— r-wtFIPV
— FIPVΔ3abc
— FIPVΔ7ab
— FIPVΔ3abc+7ab

Fig.36: Neutralizing antibody titers

FIPV 79-1146
r-wtFIPV
FIPV-Δ3abc
FIPV-Δ7ab
FIPV-Δ7ab/Δ3abc

Fig.37: Survival after challenge

Fig. 38: Growth curve FIPV recombinant nr.1 and 9.
containing the Renilla Luciferase gene

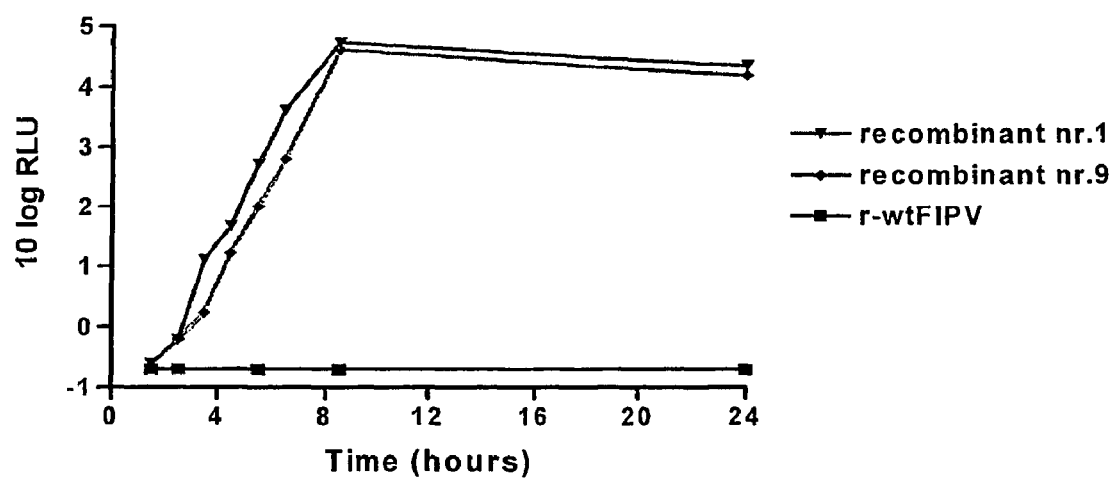
Fig.39 FIPV Renilla Luciferase expression

Fig. 40  One step growth curve FIPV deletion variants

Fig. 41

TABLE 3

RNA synthesis by recombinant MHVs [a]

| Virus [b] | RNA species | RNA length (nt) [c] | Molar ratio [d] |
|---|---|---|---|
| WT(1) | 1a/1b-2a/HE-S-4-5a/E-M-N | 31,528 | 1.00 |
|  | 2a/HE-S-4-5a/E-M-N | 9,852 | 0.14 |
|  | S-4-5a/E-M-N | 7,677 | 0.40 |
|  | 4-5a/E-M-N | 3,664 | 2.13 |
|  | 5a/E-M-N | 3,281 | 1.14 |
|  | M-N | 2,641 | 3.72 |
|  | N | 1,944 | 11.95 |
| WT(2) | 1a/1b-2a/HE-S-4-5a/E-M-N | 31,528 | 1.00 |
|  | 2a/HE-S-4-5a/E-M-N | 9,852 | 0.15 |
|  | S-4-5a/E-M-N | 7,677 | 0.42 |
|  | 4-5a/E-M-N | 3,664 | 2.24 |
|  | 5a/E-M-N | 3,281 | 1.24 |
|  | M-N | 2,641 | 3.45 |
|  | N | 1,944 | 12.38 |
| Δ45a | 1a/1b-2a/HE-S-E-M-N | 30,792 | 1.00 |
|  | 2a/HE-S-E-M-N | 9,116 | 0.29 |
|  | S-E-M-N | 6,941 | 0.59 |
|  | E-M-N | 2,935 | 0.67 |
|  | M-N | 2,641 | 2.03 |
|  | N | 1,944 | 15.74 |
| Δ2aHE | 1a/1b-S-4-5a/E-M-N | 29,370 | 1.00 |
|  | S-4-5a/E-M-N | 7,677 | 0.71 |
|  | 4-5a/E-M-N | 3,664 | 3.85 |
|  | 5a/E-M-N | 3,281 | 1.59 |
|  | M-N | 2,641 | 5.11 |
|  | N | 1,944 | 14.03 |
| min | 1a/1b-S-E-M-N | 28,634 | 1.00 |
|  | S-E-M-N | 6,941 | 0.73 |
|  | E-M-N | 2,935 | 0.74 |
|  | M-N | 2,641 | 1.40 |
|  | N | 1,944 | 14.16 |

[a] Radioactivity in RNA bands shown in Fig. 3 was quantitated by scanning with Image Quant Phosphorimager.

[b] All viruses are recombinant viruses. WT(1) and WT(2) refer to parallel infections with MHV-WT shown on the left and right side of Fig. 3, respectively.

[c] RNA length includes a polyA tail of 200 nucleotides (nt).

[d] Molar ratio (g=1) is normalized with respect to moles of genomic RNA.

Fig. 42

TABLE 4

RNA synthesis by recombinant MHVs

| Virus [a] | RNA species | RNA length (nt) [b] | number [c] |
|---|---|---|---|
| WT | 1a/1b-2a/HE-S-4-5a/E-M-N | 31,528 | 1 |
| | 2a/HE-S-4-5a/E-M-N | 9,852 | 2 |
| | S-4-5a/E-M-N | 7,677 | 3 |
| | 4-5a/E-M-N | 3,664 | 4 |
| | 5a/E-M-N | 3,281 | 5 |
| | M-N | 2,641 | 6 |
| | N | 1,944 | 7 |
| Δ2aHE | 1a/1b-S-4-5a/E-M-N | 29,370 | 8 |
| | S-4-5a/E-M-N | 7,677 | 3 |
| | 4-5a/E-M-N | 3,664 | 4 |
| | 5a/E-M-N | 3,281 | 5 |
| | M-N | 2,641 | 6 |
| | N | 1,944 | 7 |
| MSmN | 1a/1b-4-5a/E-M-S/m-N | 29,500 | 9 |
| | 4-5a/E-M-S/m-N | 7,806 | 10 |
| | 5a/E-M-S/m-N | 7,423 | 11 |
| | M-Sm-N | 6,783 | 12 |
| | Sm-N | 6,065 | 13 |
| | N | 1,944 | 7 |
| 1bMS | 1a/1b-M-S-4-5a/E-N | 29,384 | 14 |
| | M-S-4-5a/E-N | 7,698 | 15 |
| | S-4-5a/E-N | 6,980 | 16 |
| | 4-5a/E-N | 2,967 | 17 |
| | 5a/E-N | 2,584 | 18 |
| | N | 1,944 | 7 |

[a] All viruses are recombinant viruses. WT(1) and WT(2) refer to parallel infections with MHV-WT shown on the left and right side of Fig. 3, respectively.

[b] RNA length includes a polyA tail of 200 nucleotides (nt).

[c] Number corresponding with numbers in Fig. 6.

| Clinical sign | | Score/Observation |
|---|---|---|
| Fever | 40.1-40.6°C | 1 point |
| | 40.7-41.1°C | 2 points |
| | >41.1°C | 3 points |
| Depression | inactive <3 days | 1 point |
| | inactive 3-6 days | 2 points |
| | inactive > 6 days | 3 points |
| Anorexia | not eating <3 days | 1 point |
| | not eating 3-6 days | 2 points |
| | not eating > 6 days | 3 points |
| Jaundice | plasma is yellow | 1 point per week |
| Weight loss | loss >2.5% body weight per week | 1 point per week |
| Leukopenia | lymphocyte count < 0.7 10$^{-9}$/l | 1 point per week |
| Anemia | hematocrit < 0.27 l/l | 1 point per week |

Table 5: Scoring table for clinical signs following vaccination and challenge.

Fig. 43

| Cat ID | fever | depression | anorexia | jaundice | neurological disorder | weight loss | leukopenia | anemia | total score |
|---|---|---|---|---|---|---|---|---|---|
| FIPV79-1146 | | | | | | | | | |
| 249 | 2 | 3 | 3 | 4 | 0 | 3 | 6 | 4 | 25 |
| 261 | 2 | 1 | 1 | 2 | 0 | 1 | 6 | 0 | 13 |
| 277 | 1 | 2 | 2 | 3 | 1 | 2 | 6 | 0 | 17 |
| 428 | 0 | 1 | 2 | 3 | 0 | 2 | 9 | 0 | 17 |
| rFIPV79-1146 | | | | | | | | | |
| 251 | 1 | 1 | 3 | 1 | 0 | 2 | 0 | 0 | 8 |
| 263 | 0 | 2 | 3 | 1 | 1 | 3 | 0 | 0 | 10 |
| 376 | 0 | 1 | 3 | 1 | 0 | 1 | 3 | 0 | 7 |
| 380 | 2 | 1 | 2 | 0 | 1 | 0 | 0 | 1 | 7 |
| 424 | 0 | 1 | 3 | 2 | 0 | 0 | 3 | 1 | 10 |
| FIPVΔ3abc | | | | | | | | | |
| 241 | 0 | 0 | 0 | 0 | 0 | 0 | 0 | 0 | 0 |
| 279 | 0 | 0 | 0 | 0 | 0 | 0 | 0 | 1 | 1 |
| 283 | 0 | 0 | 0 | 0 | 0 | 0 | 0 | 0 | 0 |
| 400 | 0 | 0 | 0 | 0 | 0 | 0 | 0 | 0 | 0 |
| 440 | 0 | 0 | 0 | 0 | 0 | 0 | 0 | 0 | 0 |
| FIPVΔ7ab | | | | | | | | | |
| 243 | 0 | 0 | 0 | 0 | 0 | 0 | 0 | 0 | 0 |
| 281 | 0 | 0 | 0 | 0 | 0 | 0 | 3 | 0 | 3 |
| 378 | 0 | 0 | 1 | 0 | 0 | 0 | 0 | 0 | 1 |
| 426 | 0 | 0 | 0 | 0 | 0 | 0 | 0 | 0 | 0 |
| 430 | 0 | 0 | 0 | 0 | 0 | 0 | 3 | 1 | 4 |
| FIPVΔ7ab/Δ3abc | | | | | | | | | |
| 245 | 0 | 0 | 0 | 0 | 0 | 0 | 0 | 0 | 0 |
| 247 | 0 | 0 | 0 | 0 | 0 | 0 | 0 | 1 | 1 |
| 420 | 0 | 0 | 0 | 0 | 0 | 0 | 0 | 0 | 0 |
| 422 | 0 | 0 | 0 | 0 | 0 | 0 | 0 | 0 | 0 |
| 432 | 0 | 0 | 0 | 0 | 0 | 0 | 3 | 1 | 4 |

Table 6: total clinical score following initial vaccination with different mutants of FIPV79-1146

Fig. 44

| Cat ID | fever | depression | anorexia | jaundice | neurological disorder | weight loss | leukopenia | anemia | total score |
|---|---|---|---|---|---|---|---|---|---|
| Control | | | | | | | | | |
| 149 | 0 | 1 | 1 | 2 | 0 | 1 | 0 | 2 | 7 |
| 151 | 0 | 1 | 1 | 2 | 0 | 1 | 6 | 2 | 13 |
| 153 | 0 | 1 | 1 | 2 | 0 | 1 | 0 | 0 | 5 |
| 155 | 1 | 2 | 2 | 3 | 0 | 2 | 12 | 1 | 23 |
| FIPV-Δ3abc | | | | | | | | | |
| 241 | 0 | 0 | 0 | 0 | 0 | 2 | 0 | 0 | 2 |
| 279 | 0 | 0 | 0 | 0 | 0 | 0 | 0 | 0 | 0 |
| 283 | 0 | 0 | 0 | 0 | 0 | 3 | 0 | 1 | 4 |
| 400 | 0 | 0 | 0 | 0 | 0 | 0 | 3 | 1 | 4 |
| 440 | 0 | 0 | 0 | 0 | 0 | 0 | 0 | 0 | 0 |
| FIPV-Δ7ab | | | | | | | | | |
| 243 | 0 | 0 | 0 | 0 | 0 | 0 | 0 | 0 | 0 |
| 281 | 0 | 0 | 0 | 0 | 0 | 0 | 0 | 0 | 0 |
| 378 | 0 | 0 | 0 | 0 | 0 | 0 | 0 | 0 | 0 |
| 426 | 0 | 0 | 0 | 0 | 0 | 0 | 0 | 0 | 0 |
| 430 | 0 | 0 | 0 | 0 | 0 | 0 | 0 | 0 | 0 |
| FIPV-Δ7ab/Δ3abc | | | | | | | | | |
| 245 | 2 | 2 | 2 | 2 | 1 | 1 | 3 | 0 | 14 |
| 247 | 0 | 0 | 0 | 0 | 0 | 1 | 0 | 0 | 1 |
| 420 | 1 | 3 | 3 | 3 | 1 | 7 | 3 | 0 | 21 |
| 422 | 1 | 0 | 0 | 0 | 0 | 1 | 0 | 0 | 2 |
| 432 | 0 | 0 | 0 | 0 | 0 | 0 | 0 | 1 | 1 |

Table 7: Total clinical score following

CORONAVIRUS-LIKE PARTICLES COMPRISING FUNCTIONALLY DELETED GENOMES

CROSS-REFERENCE TO RELATED APPLICATION

This application is a continuation of PCT International Patent Application No. PCT/NL/02/00318, filed on May 17, 2002, designating the United States of America, and published, in English, as PCT International Publication No. WO 02/092827 A2 on Nov. 21, 2002, the contents of the entirety of which are incorporated herein by this reference.

TECHNICAL FIELD

The invention relates to the field of coronaviruses and diagnosis, therapeutic use and vaccines derived thereof.

BACKGROUND

Coronavirions have a rather simple structure. They consist of a nucleocapsid surrounded by a lipid membrane. The helical nucleocapsid is composed of the RNA genome packaged by one type of protein, the nucleocapsid protein N. The viral envelope generally contains 3 membrane proteins: the spike protein (S), the membrane protein (M) and the envelope protein (E). Some coronaviruses have a fourth protein in their membrane, the hemagglutinin-esterase protein (HE). Like all viruses, coronaviruses encode a wide variety of different gene products and proteins.

Most important among these are the proteins responsible for functions related to viral replication and virion structure. However, besides these elementary functions, viruses generally specify a diverse collection of proteins, the function of which is often still unknown, but which are known or assumed to be in some way beneficial to the virus. These proteins may either be essential-operationally defined as being required for virus replication in cell culture- or dispensable. Coronaviruses constitute a family of large, positive-sense RNA viruses that usually cause respiratory and intestinal infections in many different species. Based on antigenic, genetic and structural protein criteria they have been divided into three distinct groups: Group I, II and III. Actually, in view of the great differences between the groups, their classification into three different genera is presently being discussed by the responsible ICTV Study Group. The features that all these viruses have in common are a characteristic set of essential genes encoding replication and structural functions. Interspersed between and flanking these genes, sequences occur that differ profoundly among the groups and that are, more or less, specific for each group.

Of the elementary genes, the most predominant one occupies about two-thirds of the genome. Located at the 5' end, this so-called "polymerase gene" encodes two large precursors, the many functional cleavage products of which are collectively held responsible for RNA replication and transcription. The other elementary genes specify the basic structural proteins N, M, E, and S. The nucleocapsid (N) protein packages the viral RNA forming the core of the virion. This RNP structure is surrounded by a lipid envelope in which the membrane (M) protein abundantly occurs constituting a dense matrix. Associated with the M protein are the small envelope (E) protein and the spike (S) protein, the latter forming the viral peplomers that are involved in virus-cell and cell-cell fusion. The genes for these structural proteins invariably occur in the viral genome in the order 5'-S-E-M-N-3'.

In infected cells, the coronavirus nucleocapsids are assembled in the cytoplasm. The nucleocapsids interact with the viral envelope proteins which, after their synthesis in the endoplasmic reticulum, accumulate in the intermediate compartment, a membrane system localized between the endoplasmic reticulum (ER) and the Golgi complex. This membrane system acts as the budding compartment: the interaction of the nucleocapsids with the viral envelope proteins leads to the pinching off of virions that are then released from the cell by exocytosis.

We have recently demonstrated that the assembly of coronaviral particles does not require the involvement of nucleocapsids. Particles devoid of a nucleocapsid are assembled in cells when the viral envelope protein genes are co-expressed. The minimal requirements for the formation of virus-like particles (VLPs) are the M and E protein: the S protein is dispensable but is incorporated if present through its interactions with the M protein. Biochemical and electron microscopical analysis revealed that the VLPs are homogeneous in size and have similar dimensions as authentic corona virions. Clearly, the M and E protein have the capacity to associate in the plane of cellular membranes and induce curvature leading to the budding of specific "vesicles" which are subsequently secreted from the cells. An article describing these results has appeared in EMBO Journal (vol. 15, pp. 2020-2028, 1996).

In yet another article, coronavirus like particles were shown which were not devoid of a nucleocapsid, assembly here did not take place independent of a nucleocapsid (Bos et al., Virology 218, 52-60, 1996). Furthermore, packaging of RNA was not very efficient. Furthermore, neither of these two publications provides sufficient targeting and delivery features which would make the VLPs suitable as therapeutic carrier, for example being equipped with specific targeting information and/or with a genetic or nongenetic message.

However, coronaviruses do have several distinct theoretical advantages for their use as vectors over other viral expression systems (see, also, PCT International Publication WO98/49195): (i) coronaviruses are single-stranded RNA viruses that replicate within the cytoplasm without a DNA intermediary, making unlikely the integration of the virus genome into the host cell chromosome; (ii) these viruses have the largest RNA genome known having, in principle, room for the insertion of large foreign genes; (iii) since coronaviruses in general infect the mucosal surfaces, both respiratory and enteric, they may be used to induce a strong secretory immune response; (iv) the tropism of coronaviruses may be modified by the manipulation of the spike (S) protein allowing the engineering of the tropism and virulence of the vector; and, (v) nonpathogenic coronavirus strains infecting most species of interest are available to develop expression systems.

Two types of expression vectors have been developed based on coronavirus genomes. One requires two components (helper dependent) and the other a single genome that is modified either by targeted recombination or by engineering a cDNA encoding an infectious RNA. Helper dependent expression systems, also called minigenomes have been developed using members of the three groups of coronaviruses. Coronavirus derived minigenomes have a theoretical cloning capacity close to 25 kb, since minigenome RNAs of about 3 kb are efficiently amplified and packaged by the helper virus and the virus genome has about 30 kb. This is, in principle, the largest cloning capacity for a vector based on RNA virus genomes. Reverse genetics has been possible by targeted recombination between a helper virus and either nonreplicative or replicative coronavirus derived RNAs (9). Targeted recombination has been mediated by one or two cross-overs. Changes were introduced within the S gene that modified MHV pathogenicity. The gene encoding green fluorescent protein (GFP) was inserted into MHV between genes S and E by targeted recombination, resulting in the creation of a vector with the largest known RNA viral genome (1d). Mutations have also been created by targeted mutagenesis within the E and the M genes showing the crucial role of these genes in assembly.

DISCLOSURE OF THE INVENTION

The construction of a full-length genomic cDNA clone could considerably improve the genetic manipulation of coronaviruses. The construction of an infectious TGEV cDNA clone has recently been made possible (1c). To obtain an infectious cDNA, three strategies have been combined; (i) the construction of the full-length cDNA was started from a DI that was stably and efficiently replicated by the helper virus. Using this DI, the full-length genome was completed and the performance of the enlarged genome was checked after each step. This approach allowed for the identification of a cDNA fragment that was toxic to the bacterial host. This finding was used to advantage by reintroducing the toxic fragment into the viral cDNA in the last cloning step; (ii) in order to express the long coronavirus genome, and to add the 5' cap, a two-step amplification system that couples transcription in the nucleus from the CMV promoter, with a second amplification in the cytoplasm, driven by the viral replicase, was used; and, (iii) to increase viral cDNA stability within bacteria, the cDNA was cloned as a bacterial artificial chromosome (BAC), that produces only one or two plasmid copies per cell. The full-length cDNA was divided into two plasmids because their fusion into one reduced the stability of the cDNA. One plasmid contained all virus sequences except for a fragment Cla I to Cla I of about 5 kb that was included within a second BAC. A fully functional infectious cDNA clone, leading to a virulent virus able to infect both the enteric and respiratory tracts, was engineered by inserting the Cla I fragment into the rest of the TGEV cDNA sequence.

As said, both helper-dependent expression systems, based on two components and single genomes constructed by targeted recombination or by using an infectious cDNA have been developed. The sequences that regulate transcription have been characterized. Expression of high amounts of heterologous antigens (1 to 8 $\mu g/10^6$ cells) have been achieved, and the expression levels have been maintained for around 10 passages. These expression levels should be sufficient to elicite protective immune responses.

Single genome coronavirus vectors have been constructed efficiently expressing a foreign gene such as GFP. Thus, a new avenue has been opened for coronaviruses which have unique properties, such as a long genome size and enteric tropism, that makes them of high interest as expression vectors, be it that for vaccine development and gene therapy also other conditions need be met, notably that host virulence of vector constructs, and viability of vector constructs in cell culture need to be within distinct limitations. One the one hand, the vector may not remain too virulent, but should have at least some attenuated properties rendering it useful for in vivo replication as a gene delivery vehicle or vaccine for the host or subject undergoing therapy. On the other hand, the vector should replicate well in cell-culture, at least when commercial use is desired.

The invention provides replicative coronaviruses and replicative coronavirus-like particles (VLPs) from which large parts of their genome are (at least functionally) deleted and/or are rearranged without abolishing their replicative capacities. The deletion is preferably resulting in at least a functional deletion in that the corresponding gene is not, or is only partly, expressed wherein the resulting gene product is absent, dysfunctional or at least functionally distinct from a corresponding wild-type gene product. One striking result seen with VLPs provided with deletions and/or rearrangements as provided herein, is that the deleted or rearranged VLP, albeit capable of replication in vitro and in vivo, is in general well attenuated, in that it does not cause disease (or causes much less) in the target host, making it very suitable for therapeutic use, for example, as a delivery vehicle for genes and other cargo (wherein specific targeting may be provided as well when desired), or for use as a vaccine, being attenuated while carrying important immunogenic determinants that help elicit an immune response. Such determinants may be derived from a (homologous or heterologous) coronavirus, but may also be derived from other pathogens. In other words, the invention provides the use of a replicative VLP with a partly deleted and/or rearranged genome as a vector. Into the vector, a foreign nucleic acid sequence may be introduced. This foreign gene sequence encodes (part of) a protein. It is this protein, or part thereof, encoded by the inserted sequence, which may serve as an immunogen or a "targeting means" (i.e., a ligand capable of binding to a receptor).

In a preferred embodiment, the VLP as provided herein are further modified in one of various ways, genomically or in their protein composition, thereby exposing at their surface various biological or target molecules and/or carrying within the particles molecules with biological activity which need to be protected or shielded and/or containing genomes into which foreign genes or sequences have been incorporated. One of the major needs in present-day medicine is systems for the targeted delivery of therapeutic agents in the body. By consequence, the development of carriers that can direct cargo to specified groups of cells and introduce this cargo into these cells such that it can exert its biological activity, is a major challenge in biomedical research. Tremendous efforts have already been spent in the development and testing of systems based on liposomes, microspheres, antibodies, etc. for delivery of drugs, genes, peptides and proteins. Though many of these approaches are promising, the actual successes so far are limited. The genome of a VLP as provided herein has been deleted and/or rearranged to such an extent without abolishing replication in that it serves very well as a delivery vehicle for the cargo. Providing the VLP with cargo or using the VLP as a vector is, e.g., done by inserting a foreign gene sequence that encodes a desired molecule such as a ligand or binding molecule, whether this is an immunogen or receptor binding molecule or any other protein or peptide. In a preferred embodiment, the cargo comprises a nucleic acid into which foreign genes or sequences of interest have been incorporated. Foreign genes can be expressed by a VLP both by the additional insertion of such a gene in its genome or by using the genetic space created by deletion of nonessential genes. To further increase the safety of gene delivery therapy with corona-like viruses, such as with VLP as provided herein, the invention also provides a method for inhibiting or blocking infection with coronaviruses in general and with a coronavirus-like particle in particular, comprising treatment of an organism or cells at risk for an infection or infected with such a coronavirus or VLP with a so-called heptad repeat peptide as provided herein. All coronaviruses have herein been found to contain one or two characteristic heptad repeat regions in their S protein, which are instrumental in coronavirus entry into cells. Peptides derived from the membrane-proximal heptad repeat region (HR2; e.g., for MHV strain A59 the peptide composed of amino acids 1216-1254 of the S protein, see also FIG. 20) are particularly potent in inhibiting infection as well as fusion of infected cells with surrounding ones, as was determined in the detailed description, illustrating the advantages provided. Peptide therapy is not restricted to situations of gene therapy or delivery vehicle therapy as provided here, but can also be used in the prevention or treatment of coronaviral infections in general.

In a further embodiment, the invention provides a replicative VLP according to the invention which is also modified at the ectodomain and/or the endodomain of a viral protein. For example, by modifying the ectodomain of the spike protein, the VLP is provided with modified biological molecules as targeting means that serve to direct the VLP to interact with other biological molecules that mirror or can interact, with the target means, such as receptor proteins on cells, be it hormone receptors, specific immunoglobulinimmunoglobulins on B-cells, MHC and MHC associated molecules present on T-cells and other cells, transfer proteins or other receptor molecules known to the person skilled in the field of cell surface receptors. The targeting means can also be provided to interact with known binding sites of selected enzymes on proteins or other molecules that serve as substrate for the selected enzyme.

In another embodiment, replicative VLPs are provided exposing an immunogenic determinant, such as a bacterial toxin or a heterologous viral or bacterial protein comprising a relevant antigenic determinant specific for a pathogen. This is an example where the VLPs serve as immunogen or vaccine, here, for example, directed against the bacterial toxin. B-lymphocytes carrying the corresponding immunoglobulinimmunoglobulin at their surface are in this case the target cells for the VLPs, once recognized by the B-lymphocyte, this cell(s) will multiply and produce the appropriate antibody.

Preparation of VLPs or coronaviruses with modified spikes can be achieved genetically by modification of the viral genome such that it expresses the modified S protein in infected cells. Here, we also provide the preparation of coronaviruses containing altered spikes in a different way by expressing modified S genes in cells which are in addition infected with coronavirus. The co-incorporation of the mutant spike provides the virus with new targeting means. In one embodiment, the invention provides a corona-like viral particle (VLP) comprising a genome from which at least a fragment of one of several genes or gene clusters not belonging to the genes specifying the polymerase functions (ORF1a/1b) or the structural proteins N, M, E, and S, are deleted without resulting in a total loss of replicative capacities, thereby providing these VLP with advantageous properties for therapeutic use, for example, as a vector for gene delivery purposes or for use as a vaccine delivering a suitable antigen or epitope for eliciting an immune response in the host of interest. In other words, the nonessentialnonessential genes of coronaviruses are not crucial for in vitro growth but determine viral virulence. The attenuation acquired by their deletion thus provides excellent viral vaccines and therapeutic vectors. Gene delivery or vaccination with a coronavirus can now be achieved with the assuring knowledge that the virus-like particle delivering the gene or antigen of interest is sufficiently attenuated to not cause specific coronaviral disease. Of course, besides a VLP being only deleted in any one or several of the above mentioned nonessentialnonessential genes, the invention also provides a VLP provided with a, preferably functional (in that a substantial peptide fragment of at least 4 of the original amino acids, preferably of at least 40, is notexpressed), deletion in any of the genes encoding the structural proteins, in particular, such a deletion in a structural protein leads to a VLP with modified spike protein (S) in which part of the nucleic acid encoding the spike is deleted and optionally replaced by a foreign gene sequence, thus for example providing the spike with something other than the natural ectodomain (or endodomain) of the spike protein of the original coronavirus.

The viruses of group I, with the feline infectious peritonitis virus (FIPV) probably as the most complex member, have their typical genes located between genes S and E and downstream of the N-gene, i.e., between N-gene and 3' UTR (untranslated region). Group II viruses, to which the mouse hepatitis viruses (MHV) belong, have their particular genes between the polymerase and S genes and between the genes for the S and E proteins. One of the encoded proteins characteristic for this group is the hemagglutinin-esterase (HE) protein, which is incorporated into virions and of which the hemagglutinating and esterase activities have been demonstrated. HE activities are not essential and their significance remains to be elucidated. Finally, also the group III viruses, with the prototype coronavirus infectious bronchitis virus (IBV) as the representative, have sequences between the S and E genes but also between the M and N genes. For some of the group-specific genes, no expression products could be detected in infected cells, while for others (e.g., the HE gene in MHV), naturally occurring viral mutants carrying deletions in these genes have been observed, the possibility exists that for some of these genes, not the protein products but other gene products, such as the nucleotide sequences (DNA or RNA) per se, are important or essential.

Considering that, based on their genome organization, three groups of coronaviruses can be distinguished, the invention provides for group I (FCoV) a recombinant VLP from which preferably a fragment (preferably resulting in at least a functional deletion in that the corresponding gene is not or is only partly expressed wherein the resulting gene product is absent, dysfunctional or at least functionally distinct from a corresponding wild-type gene product) from gene 3a, 3b, 3c, 7a or 7b, or the gene as a whole has been deleted. Such a deleted VLP, albeit capable of replication in vitro and in vivo, is well attenuated, in that it does essentially not cause disease in the target host, making it very suitable for therapeutic use, for example, as a delivery vehicle for genes and other cargo (wherein specific targeting may be provided as well when desired), and for use as a vaccine, being attenuated while carrying important immunogenic determinants that help elicit an immune response. Such a deleted group I virus, especially a feline coronavirus, such as FIPV, from which a fragment corresponding to gene 3c, and/or 7b is deleted, is in particular immediately useful as a vaccine in that it expresses relevant antigenic and immunogenic determinants through its structural (among others, spike) proteins and is functionally deleted in such a way that attenuation is achieved, leading to a safe and efficacious vaccine. These live attenuated viruses still induce the fullest spectrum of humoral and cellular immune responses required to protect against infection and/or disease. Additionally, such a deleted VLP for the prevention of feline disease can be provided with heterologous proteins (or functional fragments thereon, such as (glyco)proteins of feline leukemia virus, feline calicivirus, feline herpes virus, allowing the production of a bivalent or even multivalent vaccine. When desired, other immunologically or therapeutically important polypeptides, such as cytokines, are incorporated instead or as well.

Furthermore, the invention provides for group II (MHV) a recombinant VLP from which preferably a fragment (preferably resulting in at least a functional deletion) from gene 2a, HE, 4a, 4b, or 5a, or the gene as a whole has been deleted. Such a deleted group II virus, especially an MHV, is provided with advantageous properties for therapeutic use, for example, especially as a vector for delivery purposes. Such a deleted VLP, albeit capable of replication in vitro and in vivo, is well attenuated, in that it does essentially not cause disease in the target host, making it very suitable for therapeutic use, as a delivery vehicle for genes and other cargo (wherein specific targeting may be provided as well as when desired), and for use as a vaccine, being attenuated while carrying important immunogenic determinants that help elicit an immune response.

For group III (IBV), a recombinant VLP is provided from which preferably a fragment (preferably resulting in at least a functional deletion) from gene 3a, 3b, 5a or 5b, or the gene as a whole has been deleted. In another embodiment, for groups I, II, or III, the invention provides a virus-like particle capable of replication, the particle derived from a coronavirus wherein the genes for the structural proteins do not occur in the order 5'-S-E-M-N-3'. Such a replicative VLP with rearranged gene order has two important features. One is safety, resulting from the fact that homologous recombination of the VLP genome with that of an accidental field virus is unlikely to generate viable new progeny. The other is attenuation due to the shuffling of the genes. Such a replicative VLP with rearranged gene order provides well attenuated VLPs for vaccine or gene delivery use, and is herein provided bearing the deletions from the nonessential genes as well. It is shown herein that changes in the so-called invariable order of the genes specifying the polymerase functions (ORF1a/1b) and the structural proteins S, E, M, and N in the coronaviral genome is surprisingly well tolerated, for example VLPs with gene order S, M, E, N, or E, S, M, N are easily obtained. Also here, foreign genes can be inserted at different positions in the viral genome, either as an additional gene or replacing deleted nonessential genes; these genes are expressed and are stably maintained during passage of the virus.

In another embodiment, the invention provides a recombinant VLP where nucleic acid encoding the S-protein has been modified or at least partly deleted. The S protein of these viruses is responsible for binding to the cell receptor and for subsequent fusion of viral and cellular membrane during entry. These two functions occur in separate regions of the molecule: receptor binding in the amino-terminal and fusion in the carboxy-terminal part. Therefore, by replacing (parts of) the receptor binding domain by biological molecules with different targeting specificities, coronaviruses can be directed to interact with a wide variety of target molecules that are, for instance, expressed on the surface of cells. Doing so without affecting the fusion function of the S-protein, the VLP according to the invention can fuse with or penetrate into cells not normally injectable by the original virus.

The invention provides virus-like particles (VLPs) derived from coronaviruses in which one or more copies of the viral membrane proteins have been modified so as to contain foreign protein moieties of viral (either coronaviral or noncoronaviral) or nonviral origin, which moieties either are replacing part(s) of the VLP membrane proteins or are incorporated within these membrane proteins thereby constituting an integral part of them. By this, the VLP is provided with novel biological properties such as new targeting means, or immunological information, or proteins with specific biological activity contained within the virus-like particle, which biological properties are associated with the VLP next to or in place of the natural spike protein of the original coronavirus.

In one embodiment, recombinant VLPs with deleted and/or rearranged genome are provided in which (a part of) the ectodomain (i.e., the part exposed at the outside of the viral particle) of the spike protein has been replaced by the corresponding domain (or part thereof) of the spike protein of another coronavirus. Hereby, the VLP has acquired another cell substrate specificity wherein the VLP is capable of entering cells otherwise not accessible or susceptible to the original coronavirus. In a further embodiment of the invention, VLPs are provided which are composed of the mouse hepatitis coronavirus (MHV) M and E proteins and which contain chimericchimeric spike molecules consisting of the transmembrane+carboxy-terminal domain of MHV S but the ectodomain of the spike protein of feline infectious peritonitis coronavirus (FIPV). These VLPs can now enter feline cells and deliver MHV-like particles. Particles with these chimericchimeric spikes are produced by making constructs of the coronavirus MHV S gene in which the region encoding the amino-terminal domain is replaced by the corresponding domain of FIPV. These constructs are inserted into plasmids behind a bacteriophage T7 polymerase promoter. The constructs are then co-transfected with plasmids carrying the MHV M and E genes, both also behind the T7 promotor, in OST-7 cells which have been infected with a recombinant vaccina virus expressing the T7 polymerase. The resulting VLPs contain the chimericchimeric MHV/FIPV S protein. In another embodiment of the invention, the VLP is provided by the methods used as above with ectodomains of the spike protein of infectious bronchitis coronavirus (IBV), or the ectodomain (or part thereof) of an envelope protein of any enveloped virus not belonging to the coronaviruses. For example, MHV-based VLPs are provided by the invention that carry at their surface the ectodomain of the pseudorabies virus (PRV) glycoprotein gD instead of the MHV spike ectodomain or the luminal (i.e., amino-terminal) domain (or part thereof) of any nonviral type I membrane protein. In this way, VLPs are provided that have a cell specificity for chicken cells, or pig cells, or cells reactive with the type I membrane protein.

In yet another embodiment, replicative VLPs are produced with modifications that are contained within the particles. This is achieved by the incorporation of modified constructs of any of the corona viral proteins S, M, E, and HE. In coronavirus particles, these proteins have their carboxy-terminal domain enclosed within the interior of the viral envelope. Thus, foreign protein sequences incorporated within, appended to or replacing the carboxy-terminal domain are enclosed as well. In this way, VLPs can be provided that contain protein moieties, or fragments thereof, from another virus, or nonviral proteins such as hormones, such as erythropoietin. This allows the production of VLPs containing a biological active protein or fragments thereof, which is/are shielded by the viral envelope and can be released and/or retrieved later, when the viral membrane is degraded or fused with another membrane. This allows the in vitro production in cells, or the in vivo production in secretory glands such as milk glands of biologically active substance which are otherwise harmful or toxic to the producing cells, or which for other reasons need to be produced in a shielded form.

In another embodiment, MHV-based VLPs are provided carrying on their surface or inside an enzymatically active molecule like furin, or a cytokine, or a hormone receptor, or another viral or nonviral polypeptide with biological activity. In these examples, VLPs are provided with (additional) targeting means that serve to direct the VLP to cells otherwise not accessible to the original coronavirus. The invention provides recombinantly obtained replicative VLPs which are further modified at the ectodomain and/or the ectodomain of any of the viral proteins. By modifying the ectodomain of the spike protein, the VLPs are provided with modified biological molecules as a targeting means that serve to direct the VLP to interact with other biological molecules that mirror or can interact with the target means, such as receptor proteins on cells, be it hormone receptors, specific immunoglobulins on B-cells, MHC and MHC associated molecules present on T-cells and other cells, transfer proteins or other receptor molecules known to the person skilled in the field of cell surface receptors. The targeting means can also be provided to interact with known binding sites of selected enzymes on proteins or other molecules that serve as substrate for the selected enzyme.

Preparation of VLPs or coronaviruses with modified spikes can be achieved genetically by modification of the viral genome such that it expresses the modified S protein in infected cells. Here we also provide the preparation of coronaviruses containing altered spikes in a different way by expressing modified S genes in cells which are in addition infected with coronavirus. The co-incorporation of the mutant spike provides the virus with new targeting means. As an example, we demonstrate the production of MHV particles containing the chimericchimeric MHV/FIPV S protein. The chimeric S gene construct is expressed in L cells which are subsequently infected with wild-type MHV strain A59 (MHV-A59) or a mutant thereof. The progeny virus released by the cells contains the modified S protein. To demonstrate the altered targeting, the virus was used to infect feline cells that are naturally not susceptible to MHV. The cells are now infected as shown by immunofluorescence and produce normal MHV. As another example, we demonstrate the production of MHV containing chimeric S proteins in which part of the S ectodomain has been replaced by the corresponding part (i.e., the luminal or amino-terminal domain) of the human CD4 molecule, as an example of a nonviral protein. These modified coronaviruses have acquired the property to infect HIV-infected cells and cells expressing HIV envelope glycoprotein through the specific recognition of the CD4 and HIV gp120 complex. As a result, the HIV-infected cells will undergo a lytic infection, effectively reducing the number of HIV-infected cells in the body and thereby reducing the severity of the disease or even terminating the infection.

As another example, we demonstrate the production of a VLP according to the invention containing spike molecules of which the amino-terminal part has been replaced by a single chain-antibody fragment recognizing a specific cell surface protein that is expressed on cells that can normally not be infected with the coronavirus laying at the basis of the VLP. The modified virus is able to infect these otherwise refractory cells. This example illustrates the principle that in this way, i.e., by inserting very specific targeting information into the viral spike, coronaviruses can be directed to selected cells or tissues. The single chain-antibody fragment can, for instance, be selected in phage-display systems, or in other clonal selection systems of single-chain antibody fragments known in the field.

Another aspect of the invention relates to the use of the replicative VLPs or coronaviruses as gene delivery vehicles. This can be achieved in different ways. One way is by incorporating foreign genes or sequences into the viral genome such that upon entry of the virus into cells these genes are expressed or that the inserted sequences become otherwise biologically active (as is the case with ribozymes or antisense RNAs generated by the virus within the cells). The other way uses VLPs to package foreign RNA into particles by making use of the coronaviral packaging signal(s). Incorporating foreign sequences into the coronaviral genome can be accomplished by genetic manipulation using an infectious (c-)DNA clone, a full-size DNA copy of the viral genome. It can also be achieved by RNA recombination in which case RNA representing part of the viral genome and containing the foreign sequences is introduced in infected cells allowing the foreign sequences to be incorporated through homologous recombination. Because coronaviruses will usually kill the cells they infect, it is important for most purposes to attenuate them so that they will not kill the cells with which they interact. Attenuation is here accomplished by genomically altering the virus through deletion or rearrangement.

As an example of the invention, attenuation is provided by the preparation of an MHV mutant from which an essential gene has been deleted by recombination. A mouse cell line is provided in which the MHV E gene has been chromosomally integrated allowing the E protein to be produced by the expression of the gene. MHV lacking an E gene has been produced in normal mouse cells by recombination using a synthetic RNA containing a perfect copy of the MHV genomic 3'-end except for the lack of an intact E gene. The E-defective virus is able to grow only in the cells complementing the defect. The virus produced is attenuated such that it can infect other mouse cells, but nonproductively: the lack of an E protein prevents the assembly of progeny. As an example of the principle of incorporating foreign genetic sequences into attenuated or not-attenuated VLPs or coronaviruses and of their expression is the following, provided by the invention. An MHV derived VLP is provided into which a reporter gene such as LacZ or green fluorescent protein has been recombined and one in which the chimeric MHV/FIPV S gene has been incorporated. The expression of the genes is shown by blue or green-fluorescent staining of VLP infected cells and by the acquired ability to infect feline cells, respectively. The other way to obtain coronavirus-based delivery vehicles uses VLPs comprising foreign RNA sequences. Incorporation of foreign RNA sequences into these particles requires their packaging into nucleocapsids. Viral RNA-packaging by nucleocapsid (N) protein molecules occurs by the recognition of specific sequences, packaging signal(s) by the N protein. In MHV the packaging signal includes a 69 nucleotides long region in gene 1B. Foreign (noncoronaviral) RNAs containing the coronavirus packaging signal(s), or defective coronaviral genomes in which these signal(s) have been retained but into which foreign sequences have been incorporated, are assembled into VLPs when introduced into cells expressing the N, M and E (±S) genes. The VLP can introduce into a target cell a defined RNA that may have one of several functions. An example provided by the invention is a RNA acting as mRNA and specifying a particular protein such as a toxin or an inducer of apoptosis or an antibody fragment. Another example is an antisense RNA or an RNA with ribozyme activity. For most purposes it is essential to acquire multiple copies of the RNA in each cell to obtain the desired effect. This may not be feasible with VLPs which will only carry one or a few pseudo-NC. The invention thus provides the RNAs with amplification signals such that they will be multiplied in the target cell. To achieve this goal, Semliki Forest virus (SFV) replication sequences are used as the basis of the RNA construct. SFV-derived mRNA further comprising the coronavirus encapsidation sequences and specifying a reporter protein are assembled into VLPs. The SFV-driven amplification allows synthesis of the reporter protein in cells; in animals the appearance of antibodies to the reporter protein testifies to the productive delivery of the VLPs' content. The invention also provides a VLP which is an antigen or epitope delivery vehicle meant for the induction of specific immune responses, cellular and/or humoral, systemic and/or local, including the induction and production of specific antibodies against proteins, to achieve protection against infection by pathogens, of viral and nonviral origin.

As an example, the invention provides the induction of antibodies against the reporter protein derived from SFV-derived mRNA further comprising the coronavirus encapsidation sequences and specifying a reporter protein, as described above. As another example, the induction of antibodies is demonstrated in mice to the FIPV spike and to PRV gD by immunization with the VLPs, also described hereinabove. Thus, immune responses can be elicited both against proteins which are encoded by the altered genome of the VLP and/or against proteins which have been incorporated as targeting means in the VLP, thereby partly or wholly replacing the original spike protein. The examples illustrate the applicability of the approach for the induction of immune responses against proteins as diverse as, for instance, viral, bacterial, parasitic, cellular and hormonal origins.

The invention also provides VLPs which have fully maintained the original spike protein, but which are altered genomically to attenuate the VLP and/or to encode nucleotide sequences that need to be delivered at the cells to which the original coronavirus was targeted. For example, in this way, intestinal epithelial cells, or respiratory epithelial cells, that are normally infected by TGEV, or PRCV, respectively, can now interact with VLPs derived from TGEV or PRCV, or other cell-specific coronaviruses if needed, to express proteins normally not expressed by the viruses. In this way, respiratory epithelial cells of cystic fibrosis patients can, for instance, be induced to express lung surfactant molecules that are encoded by the altered genome of the VLP. To further demonstrate the invention, various examples are provided in the detailed description which is not limiting the invention.

B. The nucleotide sequences are shown of the new junctions created in the plasmid constructs (and the resulting viruses), the positions and numbers of which are indicated in part A (left side). The first sequences is SEQ ID NO:33. The second sequence is SEQ ID NO:34. The third sequence is SEQ ID NO:35.

Figure 2:
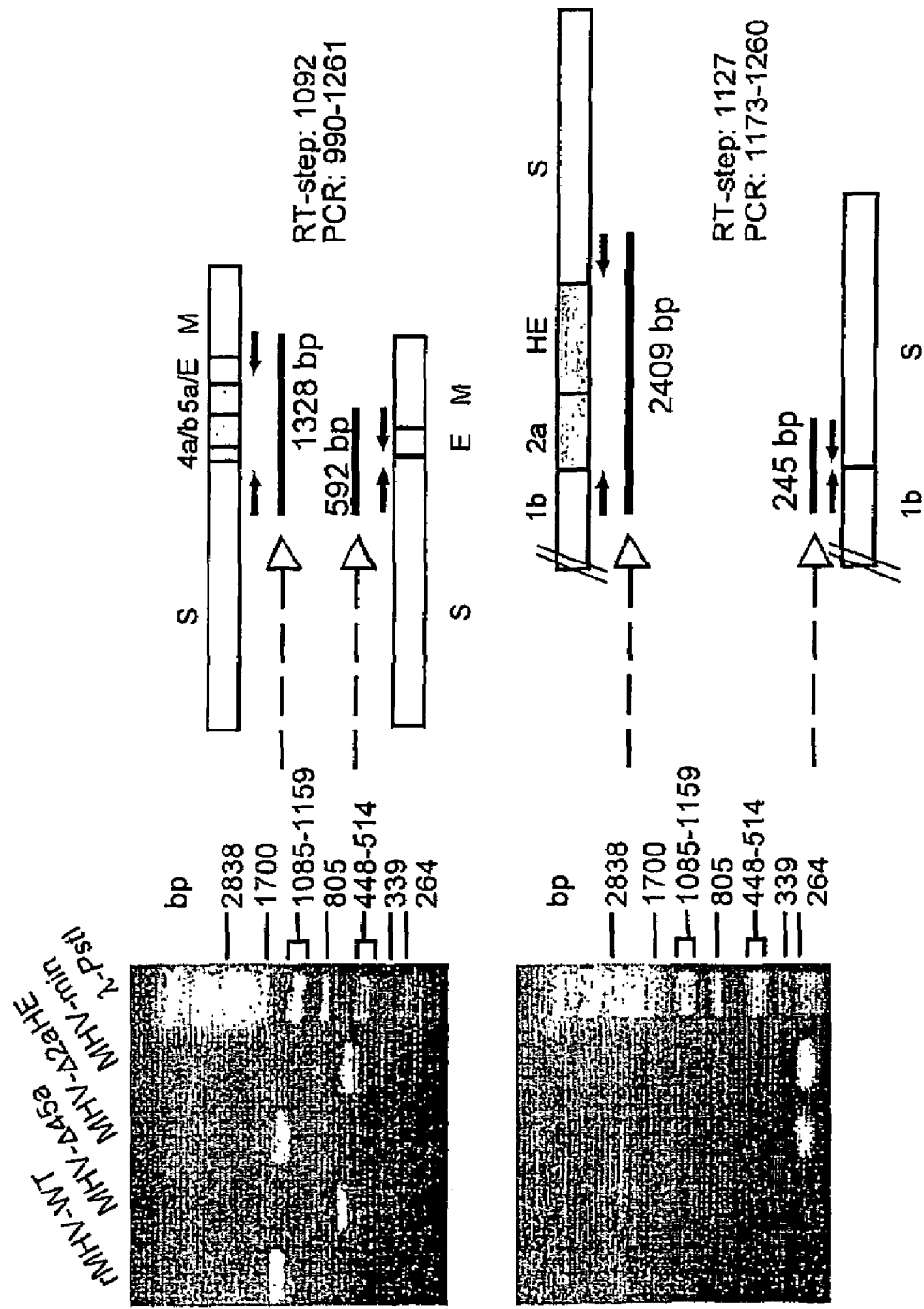

FIG. 2: RT-PCR analysis of recombinant viruses with genetic deletions. Genomic RNA was isolated from cloned virus, cDNA was prepared by RT with proper primers (1092 and 1127) and PCR was done with primers 1261+990 or with primers 1173+1260 to analyze the region of genes 4a/b/5a or of genes 2a+HE, respectively. The outline of the analyses is shown at the right, the results of the agarose gel analyses of the PCR products is shown at the left. The viruses analyzed are shown above the gel. In the right lane marker DNAs were run.

FIG. 3: Viral RNAs synthesized in infected cells by the different MHV deletion mutants were analyzed by extraction of total cytoplasmic RNA, metabolically labeled with [$^{33}$P] orthophosphate in the presence of actinomycin D, followed by electrophoresis in 1% agarose gel. The genetic make-up of the deletion viruses is shown at the top while the subgenomic RNA species are designated at the right also according to their genetic composition.

Figure 4:
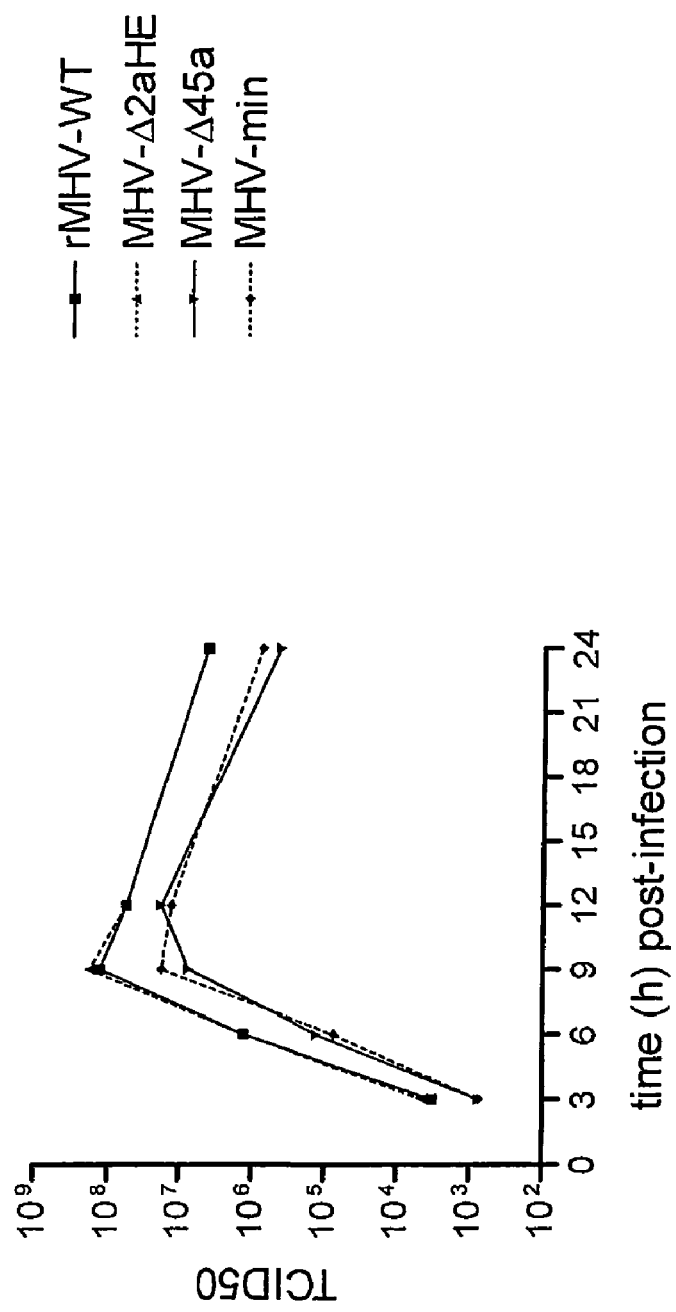

FIG. 4: One-step growth curves of the recombinant deletion viruses. After high-m.o.i. infection of LR7 cells with the deletion viruses and MHV-WT samples were taken from each culture medium at different times and the infectivity in these samples was analyzed by titration.

Figure 5:
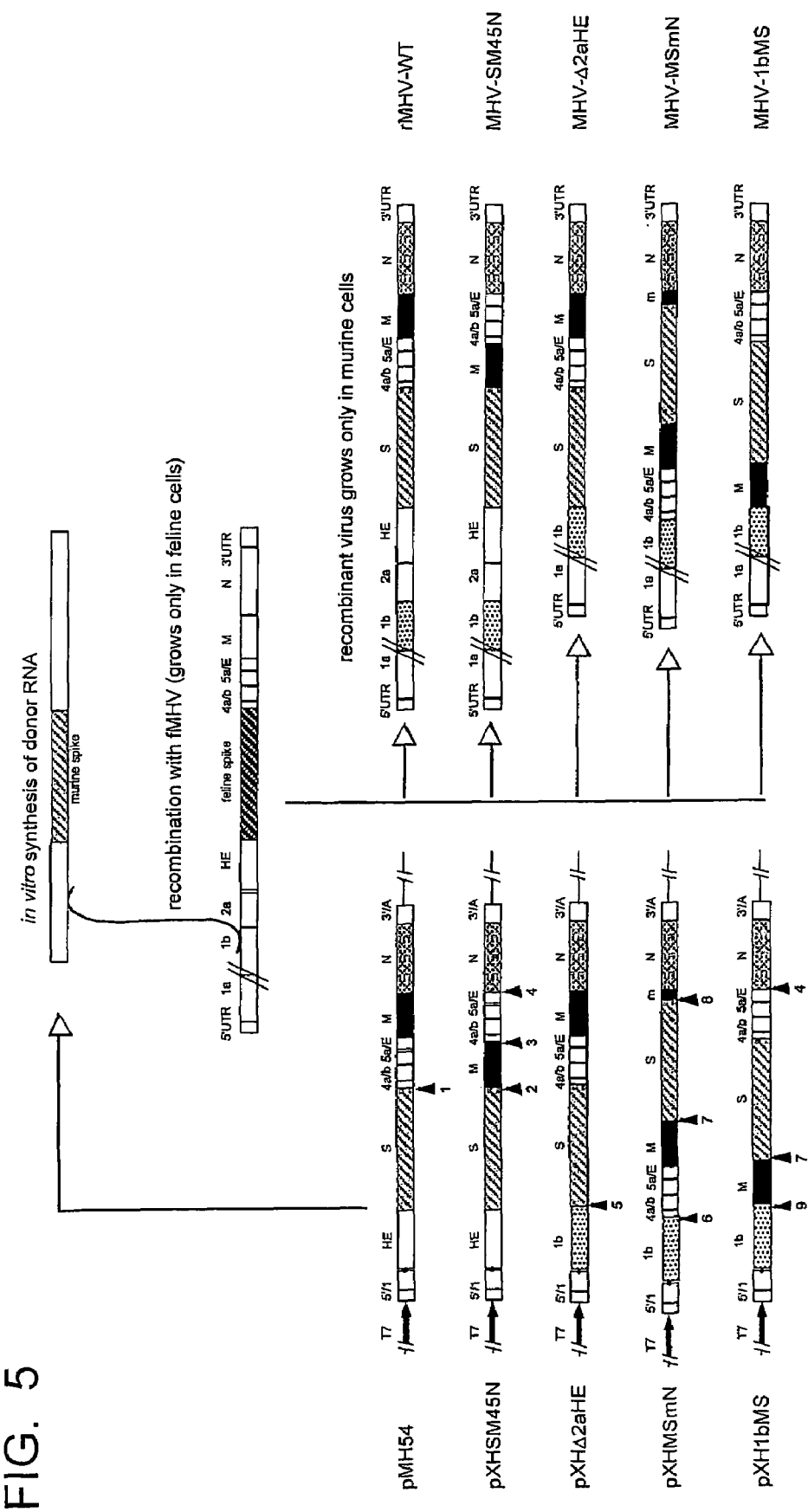

FIG. 5: As in FIG. 1 the construction of viruses with rearranged gene order is depicted. On the left are the relevant parts of plasmid constructs: the genome organization of their MHV cDNA sequences and the designations of the plasmids. On the right are the respective viruses with their genome structure and their names.

Figure 6:
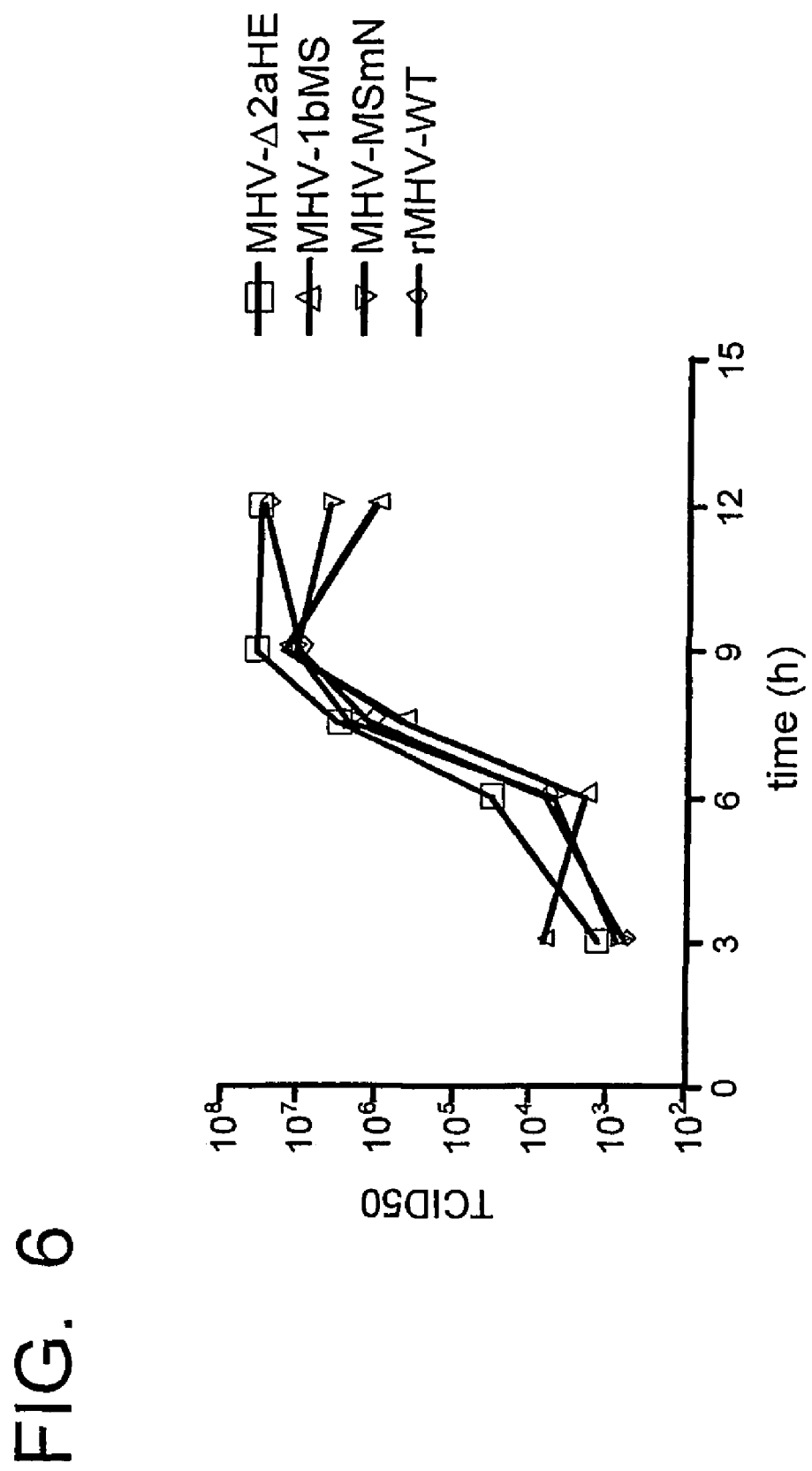

FIG. 6: One-step growth curves of the recombinant viruses with rearranged genome. After high-m.o.i. infection of LR7 cells with the viruses MHV-Ä2aHE (Δ2aHE), MHV-1bMS, MHV-MSmN, or MHV-WT samples were taken from each culture medium at different times and the infectivity in these samples was analyzed by titration.

Figure 7B:
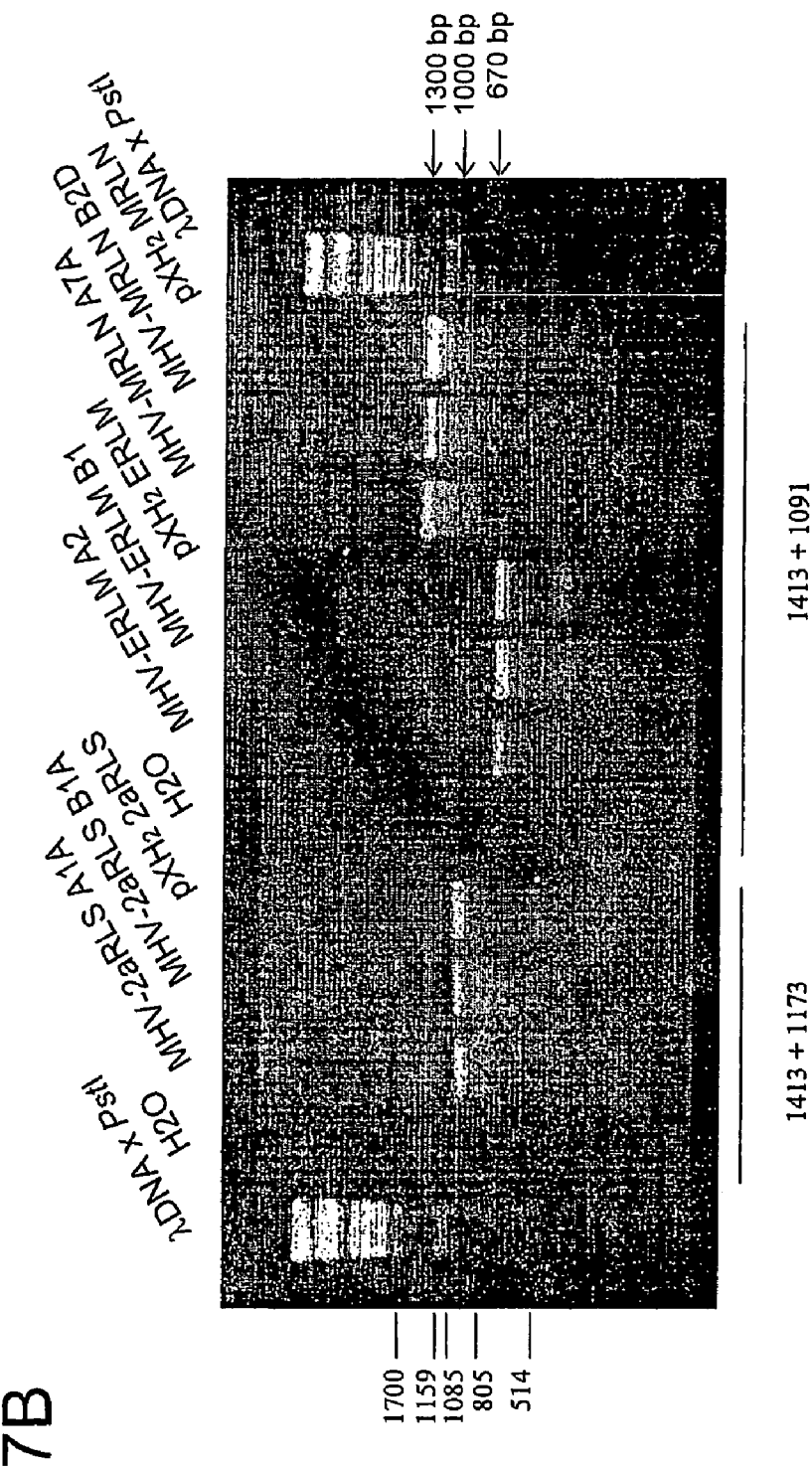

FIG. 7: A. As in FIG. 1 the construction of viruses with foreign gene insertions is depicted. At the left the various plasmid (vector) constructs, with their names, are depicted. At the right, the genetic make-up of viruses obtained with these plasmids by RNA recombination in feline cells are shown together with their names. Below: the primer sequences (and numbers) used for the introduction of an intergenic promoter sequence (IGS) in front of the renilla (RL) and firefly luciferase (FL) gene. Primer 1286 is SEQ ID NO:16, and Primer 1287 is SEQ ID NO:36.

B. RT-PCR analysis of recombinant viruses carrying the RL gene. cDNA was prepared using primer 1412 by RT on viral RNA; for each virus two independently derived viruses (designated by the extensions A1A and B1A; A2 and B1; A7A and B2D) were analyzed in parallel. Subsequently, PCR was carried out on the resulting cDNA as well as on the plasmids used to generate the viruses (see FIG. 7A) with the primer pairs indicated at the bottom of the figure. For each set, a negative control sample (H$_2$O) was also included. The agarose gel analysis of the PCR fragments together with DNA markers (flanking lanes) are shown and the sizes of the products are indicated at the right.

Figure 8A:
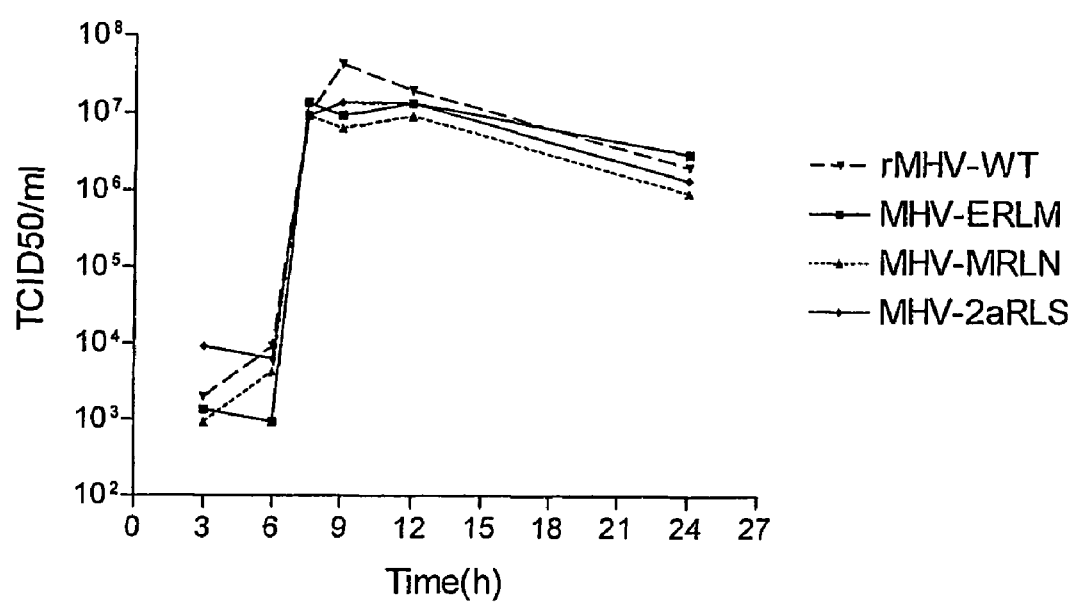

FIG. 8: One-step growth curves of the recombinant viruses carrying foreign genes. After high-m.o.i. infection of LR7 cells with viruses, samples were taken from each culture medium at different times and the infectivity in these samples was analyzed by titration.

A. Growth curves of different viruses having the renilla luciferase gene as compared to MHV-WT.

B. The growth of two independently obtained clones of MHV-EFLM virus carrying the firefly luciferase gene is shown as compared to MHV-WT.

Figure 9A:
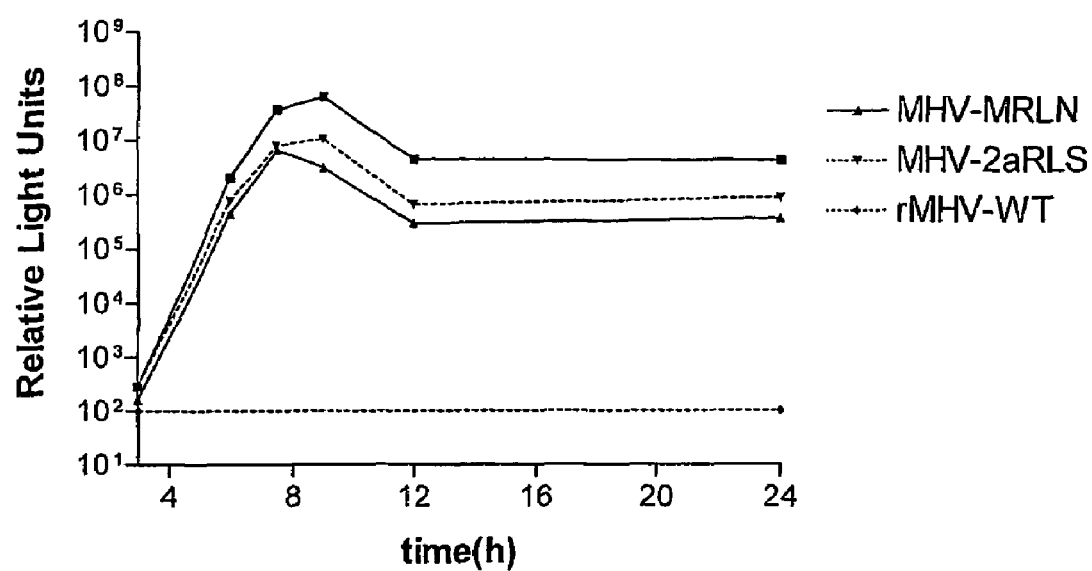
Figure 9B:
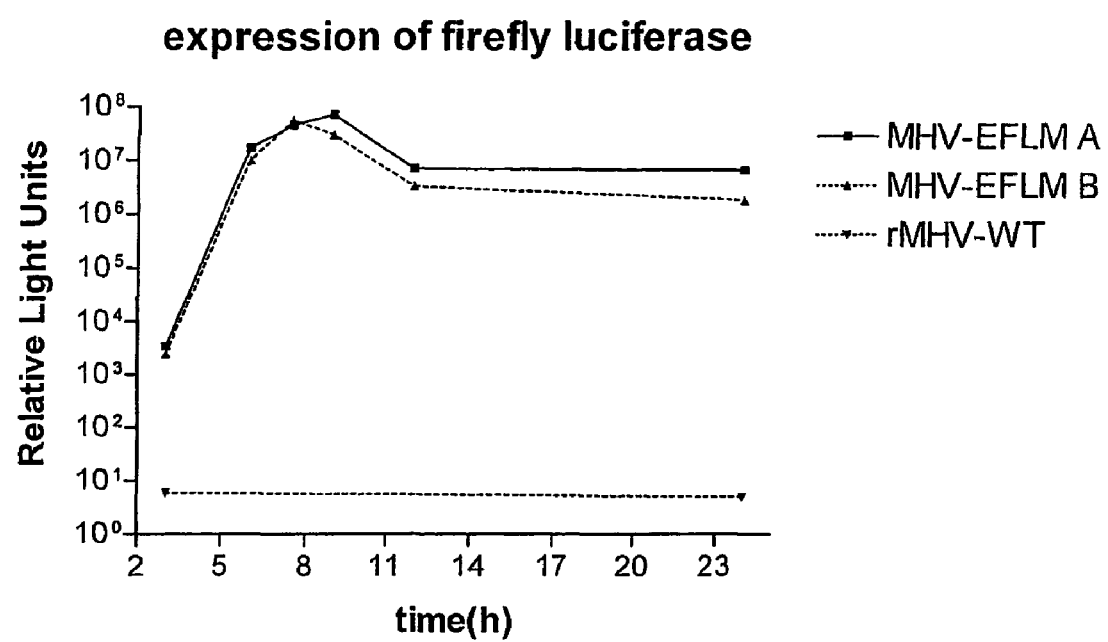

FIG. 9: Expression of luciferase by recombinant viruses. LR7 cells were infected with viruses expressing the renilla (A) or firefly (B) luciferase and with MHV-WT, and the luciferase activity generated in the cells was monitored over time. In B the two independently obtained clones of MHV-EFLM virus (see FIG. 8B) are compared to MHV-WT.

Figure 10:
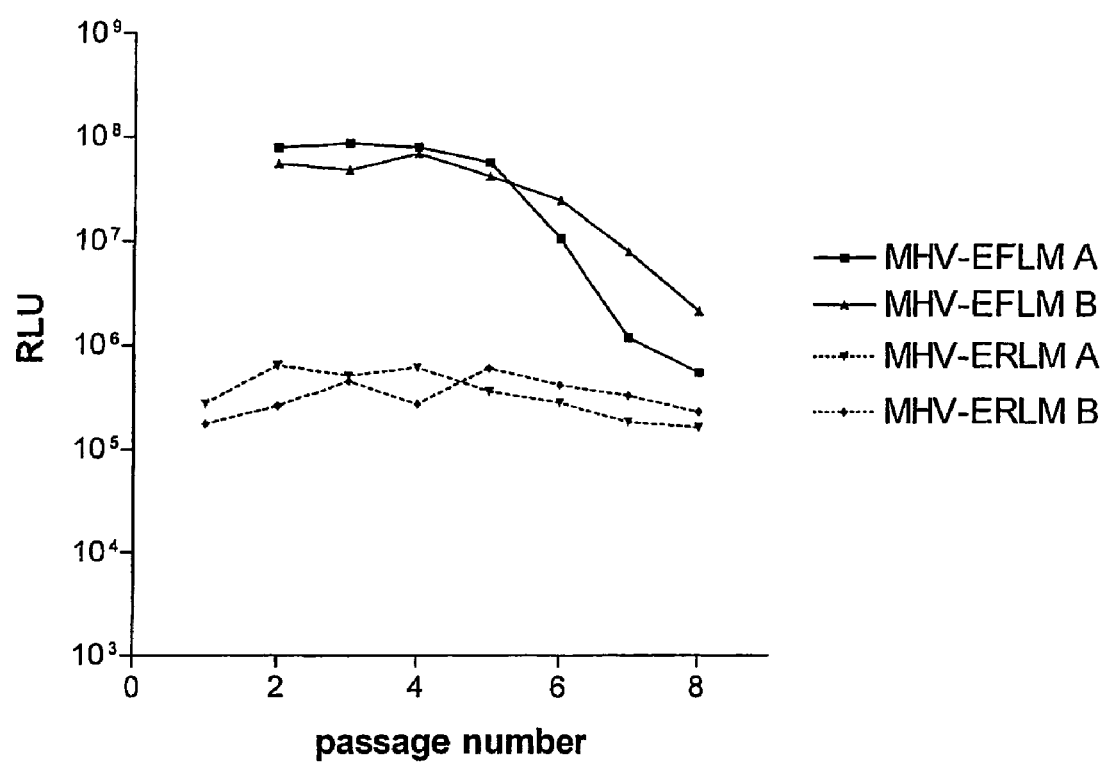

FIG. 10: Stability of viruses carrying foreign genes. The recombinant viruses MHV-ERLM and MHV-EFLM (two independently obtained clones in each case) were passaged 8 times, over LR7 cells at low m.o.i. After each passage, the viral infectivity (TCID50) in the harvested culture medium was determined. The collection of viruses thus obtained was inoculated in parallel into LR7 cells at m.o.i. of 5 and the luciferase expression in the cells at 8 hours post-infection was quantified. Results are plotted as a function of passage number.

FIG. 11: Inhibition of MHV infection by the HR2 peptide. LR7 cells were inoculated with the virus MHV-EFLM in the presence of different concentrations of HR2 peptide or, as a control, a peptide corresponding to amino acids 1003-1048 of the viral S protein. After one hour of inoculation, cells were washed and incubated further in the absence of peptide. To evaluate the success of the infection, cells were analyzed at 4 hours post-infection for luciferase expression. In the figure luciferase activity is plotted against the different peptide concentrations used.

Figure 12:
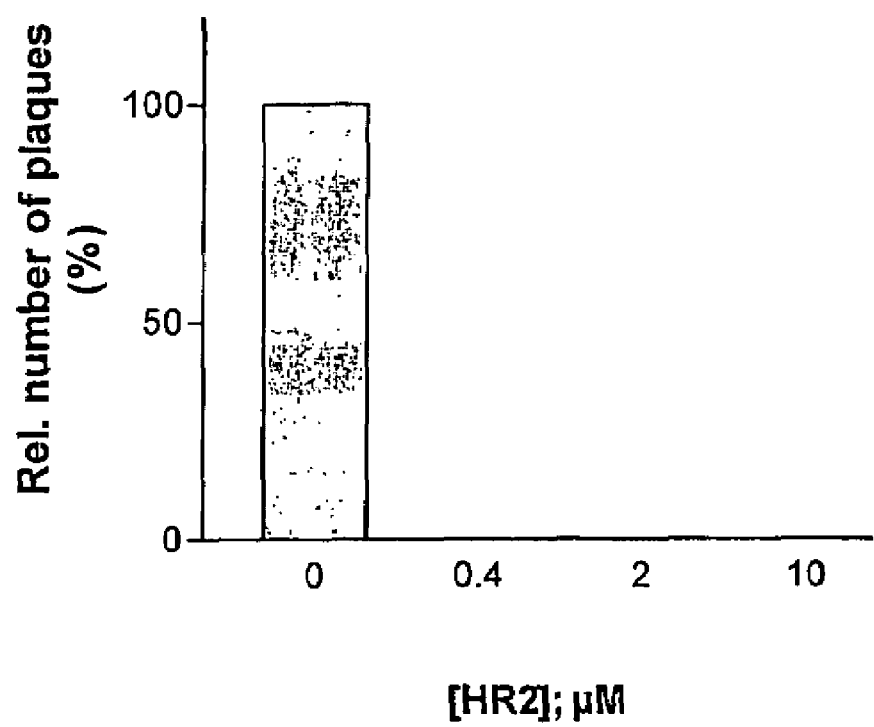

FIG. 12: Inhibition of cell-cell fusion by HR2 peptide. After inoculation of parallel cultures of LR7, cells with MHV-A59 cells were overlaid with agar medium containing different concentrations of HR2 peptide and plaques were counted the following day.

FIG. 13: A. The genetic structure of the primary plasmid vector pBRDI1 as compared to that of the parental virus from which it was derived. The top part shows the genome organization of FIPV strain 79-1146. The dotted parts (i.e., the very 5'-most 702 bases and the 3'-derived 9,262 bases) were assembled into the cDNA construct of pBRDI1; in this plasmid the viral cDNA is preceded by a phage T7 promoter sequence and the insert is flanked by XhoI (5') and NotI (3') restriction sites.

B. Plasmid pBRDI2 is a derivative of pBRDI1 in which the FIPV S gene has been replaced by a chimeric S gene (designated mS) which encodes the MHV-A59 S ectodomain while having retained the sequences for the FIPV S protein transmembrane and endodomain. Plasmid pBRDI2 was obtained by substituting in pBRDI1 the SacI-AflII segment by the corresponding fragment of pTMFS1. The latter plasmid is a derivative of plasmid pTMFS (12) which contains the chimeric gene sequence and into which a SacI-StuI fragment was cloned to extend the MHV S sequence at its 5' end with sequences corresponding to the FIPV pol1B 3' end.

FIG. 14: Sequence details of the pBRDI constructs.

A. The nucleotide sequence of pBRDI1 and pBRDI2 around the very 5' end of the FIPV genome sequence: the XhoI site and the phage T7 sequence are followed by a G-triplet and subsequently by the FIPV sequence. The entire sequence is SEQ ID NO:37.

B. The sequence at the pol1A/pol1B junction. The codon sequence is SEQ ID NO:38. The amino acid sequence is SEQ ID NO:39.

C. The nucleotide sequence at the very 3' end of the cDNA construct. The 3' untranslated region (3' UTR) is followed by a stretch of adenine nucleotides and a NotI sequence. The entire sequence is SEQ ID NO:40.

D. Nucleotide sequence at the FIPV pol1B-MHV S transition in pTMFS1 and pBRDI2. The codon sequence is SEQ ID NO:41. The top amino acid sequence is SEQ ID NO:42, and the bottom amino acid sequence is SEQ ID NO:43.

FIG. 15: Schematic picture of the generation of mFIPV by the recombination of FIPV genomic RNA and pBRDI2 derived synthetic RNA in feline cells. The genetic organization in each RNA is indicated as well as the selection for recombinant (i.e., chimeric mS containing) virus by growth on murine cells.

FIG. 16: Analysis of the mFIPV structural proteins. Murine LR7 cells were infected with mFIPV and, for comparison, with MHV-A59; feline FCWF cells were infected with FIPV strain 79-1146. Infected cells were labeled with $^{35}$S-amino acids from 5-7 hours post-infection cell lysates were prepared and immunoprecipitations were carried out with different antibodies: polyclonal antibodies against FIPV (lanes 1, 6, and 10) and MHV (lanes 3, 4, 8 and 12) and monoclonal antibodies against the feline S protein ($S_f$; lanes 2, 7, and 11) and the murine S protein ($S_m$; lanes 5, 9, and 13). The proteins were analyzed by electrophoresis in SDS-12% polyacrylamide gel. The position in the gel of the MHV and FIPV proteins are indicated at the left and right side, respectively. The mFIPV S protein is precipitated by the MHV S specific sera, not by those precipitating the FIPV S protein, and its migration in gel is similar to that of the MHV S protein.

Figure 17:
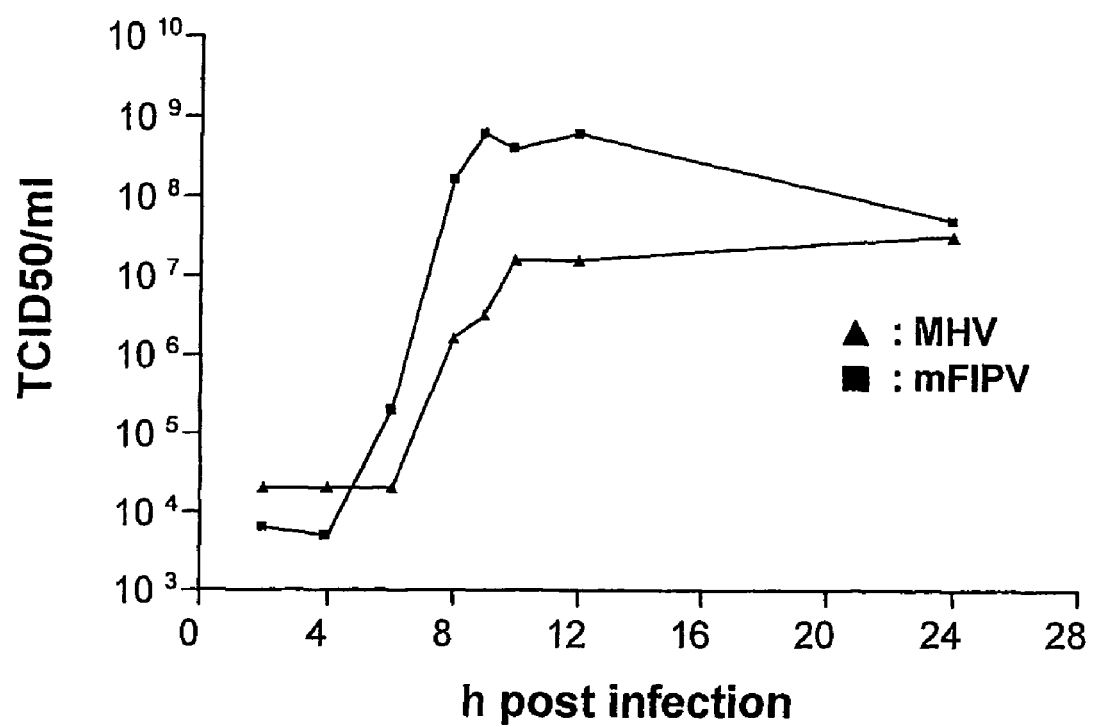

FIG. 17: One-step growth curves of mFIPV as compared to MHV. After high-m.o.i. infection of LR7 cells with the two viruses, samples were taken from each culture medium at different times and the infectivity in these samples was analyzed by titration.

Figure 18:
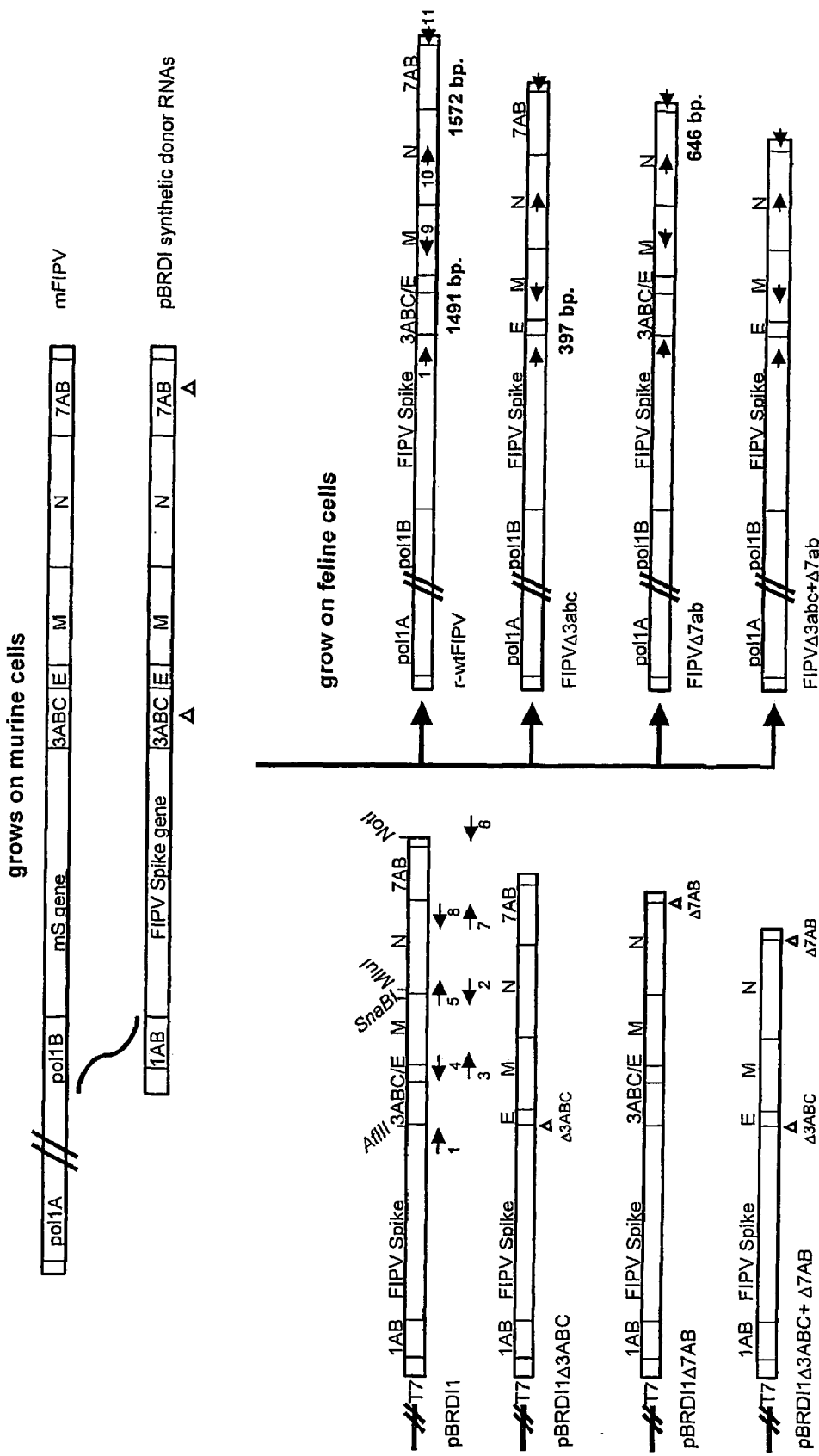

FIG. 18: Generation of FIPV deletion mutants. At the top the principle of the method is shown: recombination of the mFIPV RNA with synthetic pBRDI derived donor RNA carrying the intact FIPV S gene. Below this are depicted the genetic make-up of the constructed pBRDI1 plasmids (left) and of the generated viruses (right). Arrows indicate the position (and number) of the primers used, open triangles indicate deletions. At the right, numbers of base pairs (bp) indicate the sizes of PCR fragments predicted to be obtained with the indicated primer pairs.

Figure 19:
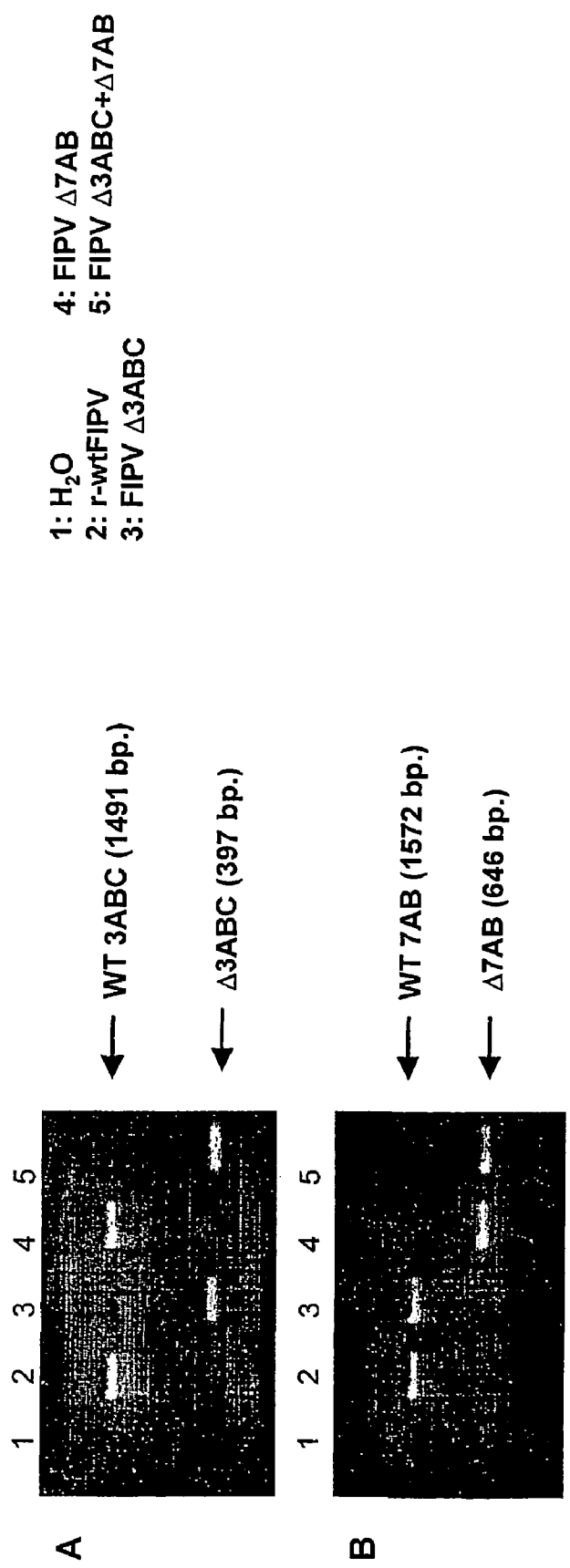

FIG. 19: Genetic analysis of the recombinant FIPV deletion viruses. Genomic RNA was isolated from the deletion viruses as well as from recombinant wild-type FIPV. RT and PCR reactions were carried out using the primers 1 and 9 for the analysis of the genes 3ABC region (panel A) and primers 10 and 11 for the genes 7AB (panel B). The positions of the DNA fragments in the agarose gels are indicated alongside the gel together with their predicted size (c.f. FIG. 18, right). The viral RNAs analyzed in the different lanes are indicated at the right.

FIG. 20: Heptad repeat (HR) regions and their amino acid sequences in coronavirus spike proteins. In the HR1 region, MHV is SEQ ID NO:44, HCV-OC43 is SEQ ID NO:45, HCV-229E is SEQ ID NO:46, FIPV is SEQ ID NO:47, and IBV is SEQ ID NO:48. Peptide HR1 is SEQ ID NO:49. Peptide HR1a is SEQ ID NO:50. Peptide HR1b is SEQ ID NO:51. Peptide HR1c is SEQ ID NO:52. In the HR2 region, MHV is SEQ ID NO:53, HCV-OC43 is SEQ ID NO:54, HCV-229E is SEQ ID NO:55, FIPV is SEQ ID NO:56, and IBV is SEQ ID NO:57. Peptide HR2 is SEQ ID NO:58.

A. Schematic representation of the coronavirus MHV-A59 spike structure. The spike (S) glycoprotein contains an N-terminal signal sequence (SS) and a transmembrane domain (TM) close to its C-terminus. S is proteolytically cleaved (arrow) in an S1 and S2 subunit, which are noncovalently linked. S2 contains two conserved heptad repeat regions, HR1 and HR2, as indicated.

B. Sequence alignment of HR1 and HR2 domains of MHV-A59, HCV-OC43 (human coronavirus strain OC43), HCV-229E (human coronavirus strain 229E), FIPV and IBV (infectious bronchitis virus strain Beaudette). The alignment shows a remarkable insertion of exactly 2 heptad repeats (14 aa) in both HR1 and HR2 of HCV-229E and FIPV, which is present in S proteins of all group I viruses. The predicted hydrophobic heptad repeat a and d residues are indicated above the sequence. The frame shift of predicted heptad repeats in HR1 is caused by a stutter. Asteriks denote conserved residues. The amino acid sequences of the peptides HR1, HR1a, HR1b, HR1c and HR2 used in this study are presented in italics below the alignments. N-terminal residues derived from proteolytic cleavage site of the GST-fusion protein are between brackets.

FIG. 21=Table 1: The sequences are shown of the junctions that were generated in the plasmids depicted in FIG. 5 and in the viruses obtained with these plasmids. The numbers correspond to the numbering of the junctions as indicated by arrowheads in the plasmids (FIG. 5, left). The first sequence is SEQ ID NO:59. The second sequence is SEQ ID NO:60. The third sequence is SEQ ID NO:61. The fourth sequence is SEQ ID NO:62. The fifth sequence is SEQ ID NO:63. The sixth sequence is SEQ ID NO:64. The seventh sequence is SEQ ID NO:65. The eighth sequence is SEQ ID NO:66. The ninth sequence is SEQ ID NO:67.

FIG. 22=Table 2: Primers used for splicing overlap extension (SOE)-PCR and for RT-PCR in the construction and analysis of recombinant FIPVs. For their position on the FIPV genome: see FIG. 18, in which their numbers and sense are indicated by arrows. The numbering of the primers refers to that in the pBRDI1 sequence. Primer 1 is SEQ ID NO:68. Primer 2 is SEQ ID NO:69. Primer 3 is SEQ ID NO:70. Primer 4 is SEQ ID NO:71. Primer 2 is SEQ ID NO:72. Primer 6 is SEQ ID NO:73. Primer 7 is SEQ ID NO:74. Primer 8 is SEQ ID NO:75. Primer 9 is SEQ ID NO:76. Primer 10 is SEQ ID NO:77. Primer 11 is SEQ ID NO:78.

FIG. 23=Addendum 1: Nucleotide sequence of plasmid pBRDI1 (SEQ ID NO:79). The sequence starts with the XhoI site (ctcgag) followed by the phage T7 polymerase promoter sequence and the triple G sequence, after which it proceeds with the 5' FIPV cDNA sequence.

FIG. 24=Addendum 2: Nucleotide sequence of plasmid pBRDI2 (SEQ ID NO:80). The sequence starts with the XhoI site (ctcgag) followed by the phage T7 polymerase promoter sequence and the triple G sequence, after which it proceeds with the 5' FIPV cDNA sequence.

FIG. 25: Survival of C57B1/6 mice infected with MHV recombinants. Four-week-old mice were inoculated intracranially with various dilutions of recombinant wild type and deletion viruses (n=5 per virus) and survival was monitored. The data for mice infected with $2.5\times10^5$ PFU are shown. While the animals infected with MHV-WT had all succumbed by day 7 post-infection, all mice inoculated with the deletion mutant viruses survived until 21 days post-infection.

FIG. 26A: Infected 17Cl1 cells were metabolically labeled with [$^{33}$P]orthophosphate in the presence of actinomycin D essentially as described (4, 10). Samples of total cytoplasmic RNA, purified using Ultraspec reagent (Biotecx), were denatured with formaldehyde and formamide, separated by electrophoresis through 1% agarose containing formaldehyde, and visualized by fluorography. The different RNA species are indicated by numbers corresponding with Table 4 (=FIG. 42).

FIG. 26B: Mice inoculated intraperitoneally with $1\times10^6$TCID$^{50}$ of each MHV recombinant were euthanized at day 4 post-infection and the viral replication in the liver was determined by quantitative plaque assays.

FIG. 27: RT-PCR analysis of recombinant viruses MHV-EFLM and MHV-minFL.cDNA was prepared using primer 1475 by RT on viral RNA; for each virus two independently derived viruses (designated by the extensions A1A and B1A, A6F and B4A) were analyzed in parallel. Subsequently, PCR was carried out on the resulting cDNA as well as on the plasmids used to generate the viruses (see, FIG. 7A) with the primer pair 935 and 1474. The agarose gel analysis of the PCR fragments together with a DNA marker is shown.

FIG. 28: RT-PCR analysis of recombinant viruses MHV-EFLM and MHVminFL. cDNA was prepared using primer 1412 by RT on viral RNA; for each virus two independently derived viruses (designated by the extensions A2E and B4D) were analyzed in parallel. Subsequently, PCR was carried out on the resulting cDNA as well as on the plasmids used to generate the viruses (see, FIG. 7A) with the primer pairs indicated at the bottom of the figure. The agarose gel analysis of the PCR fragments together with a DNA marker is shown.

FIGS. 29-31: RNA synthesis by recombinant MHVs. The genomes of the recombinant viruses are depicted at the top, their observed RNA expression patterns are shown below. Infected 17Cl1 cells were metabolically labeled with [$^{33}$P] orthophosphate in the presence of actinomycin D essentially as described (4, 10). Samples of total cytoplasmic RNA, purified using Ultraspec reagent (Biotecx), were denatured with formaldehyde and formamide, separated by electrophoresis through 1% agarose containing formaldehyde, and visualized by fluorography. Note that the subgenomic RNA species in this figure are designated by their composition, rather than as RNA2 through RNA7, since the numerical designations would be ambiguous for the mutants.

FIG. 29: MHV-WT, MHV-ERLM and MHV-EFLM

FIG. 30: MHV-EFLM and MHV-minFL

FIG. 31: MHV-MRLN, MHV-ERLM, MHV-2aRLS, MHV-MSmNRL, and MHV-MSmN

FIG. 32: In vitro replication of the recombinant viruses carrying foreign genes. After high-m.o.i. infection of LR7 cells with viruses (top: MHV-MRLN, MHV-ERLM, MHV-2aRLS; middle: MHV-EFLM, MHV-minFL; bottom, MHV-ERLM, MHV-MSmNRL), samples were taken from each culture medium at 9 hours post-infection and the infectivity in these samples was analyzed by titration.

FIG. 33: Expression of luciferase by recombinant viruses. Intracellular expression of firefly and renilla luciferase of several recombinant viruses was determined according to the manufacturer's instructions (Promega) at 9 hours post-infection. Top: MHV-EFLM and MHV-minFL; bottom: MHV-ERLM and MHV-MSmNRL.

FIG. 34: Expression of firefly luciferase in vivo. Eight-week-old, MHV-negative, female BALB/c mice were used in the experiment. Mice were inoculated intranasally with MHV-EFLM. Four animals per dose ($10^6$ TCID$^{50}$) were used. Mice were sacrificed and the livers and brains were removed at day 4 post-infection. Organs were quick-frozen in liquid nitrogen and homogenized in Cell Culture Lysis Reagent provided with the Luciferase Assay System (Promega). FL activity was measured according to the manufacturer's instructions using a luminometer (Lumac Biocounter M2500).

FIG. 35: Survival rates following inoculation of cats with various deletion mutants: FIPW 79-1146; r-wtFIPV; FIPVΔ3abc; FIPVΔ7a; and FIPVΔ3abc+7ab (100 pfu).

FIG. 36: FIPV neutralizing antibody titers raised at different time points after infection of cats with FIPV deletion variants.

FIG. 37: Survival rates following challenge of cats with FIPV 79-1146 (100 pfu). Cats (N=4) not previously vaccinated (□); cats (N=5) previously vaccinated with FIPVΔ3abc (♦); cats (N=5) previously vaccinated with FIPVΔ7ab (□); and cats (N=5) previously vaccinated with FIPVΔ3abc+7ab (□).

FIG. 38: One-step growth curves of the recombinant FIPV viruses carrying foreign genes. After high-m.o.i. infection of FCWF cells with viruses, samples were taken from each culture medium at different times and the infectivity in these samples was analyzed by titration. Recombinant nr. 1 (□) and nr. 9 (♦).

FIG. 39: Expression of luciferase by recombinant viruses. FCWF cells were infected with viruses expressing the renilla luciferase (nr. 1☐; and nr. 9◆) and with wt-rFIPV (☐), and the luciferase activity generated in the cells was monitored over time.

FIG. 40: One-step growth curves of the recombinant FIPV viruses with deletion of nonessential genes. After high-m.o.i. infection of FCWF cells with viruses, samples were taken from each culture medium at different times and the infectivity in these samples was analyzed by titration.

FIG. 41=Table 3 Quantifications of RNA synthesis by recombinant MHVs carrying deletions of nonessential genes.

FIG. 42=Table 4 Quantifications of RNA synthesis by recombinant MHVs with rearranged genomes.

FIG. 43=Table 5 Scoring table for clinical signs following vaccination and challenge.

FIG. 44=Table 6 Total clinical score following initial vaccination with different mutants of FIPV79-1146.

FIG. 45=Table 7 Total clinical score following challenge with FIPV 79-1146.

FIG. 46A: Replication of the recombinant virus carrying 2 foreign genes. After high-m.o.i. infection of LR7 cells with viruses (MHV-RLFL, MHV-2aRLS, and MHV-EFLM) samples were taken from each culture medium at 9 hours post-infection and the infectivity in these samples was analyzed by titration.

Figure 46B:
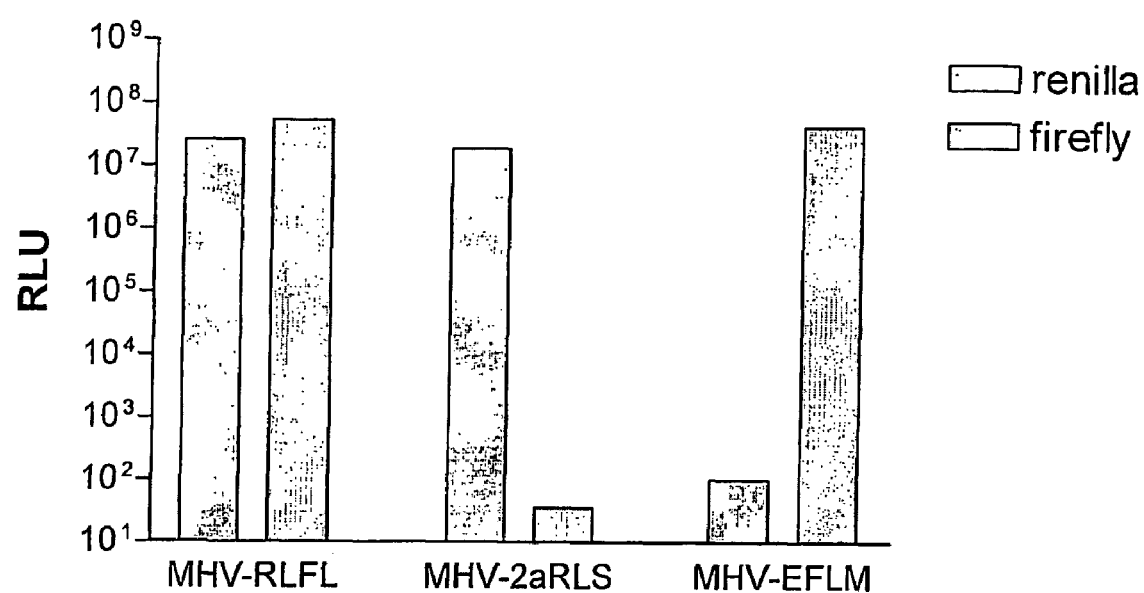

FIG. 46B: Expression of luciferase by recombinant viruses. Intracellular expression of firefly and renilla luciferase of several recombinant viruses was determined according to the manufacturer's instructions (Promega) at 9 hours post-infection (MHV-RLFL, MHV-2aRLS, and MHV-EFLM).

Experimental data related to the patent:

I. Mouse Hepatitis Virus (MHV), strain A59 (MHV-A59)
  1. Generation of live attenuated viruses
    a. Construction of recombinant MHVs lacking genes
    b. Confirmation of the recombinant genotypes
    c. RNA synthesis by MHV deletion mutants
    d. Tissue culture growth phenotype
    e. Virulence of recombinant viruses in mice
  2. Generation of recombinant viruses with rearranged gene order
    a. Construction of recombinant viruses with rearranged gene order
    b. RNA synthesis by MHV mutants with rearranged gene order
    c. Tissue culture growth phenotype
    d. Replication of recombinant viruses in mice
  3. Generation of recombinant viruses expressing foreign genes
    a. Construction of recombinant viruses carrying reporter genes
    b. RNA synthesis by recombinant viruses
    c. Replication of viruses expressing renilla or firefly luciferase
    d. Expression of renilla and firefly luciferase in cell culture
    e. Maintenance of foreign genes during viral passage
    f. Expression of firefly luciferase in mice
    g. Generation of MHV expressing two foreign genes from one genome
    h. Generation of MHV expressing a chimeric Spike-GFP gene
  4. Inhibition of infection and of cell fusion by spike protein derived peptide II. Feline Infectious Peritonitis Virus (FIPV), strain 79-1146
  1. Generation of mFIPV, a feline coronavirus growing on murine cells
    a. Construction of a synthetic RNA transcription vector
    b. Generation of mFIPV by RNA recombination
    c. mFIPV protein analysis
    d. mFIPV growth characteristics
  2. Generation of live attenuated FIPV vaccine by gene deletions
    a. Construction of synthetic RNA transcription vectors
    b. Generation of recombinant FIPVs lacking genes
    c. Genetic analysis of recombinant FIPVs lacking genes
    d. Growth characteristics of FIPVs lacking genes
    e. Virulence of recombinant viruses in cats
    f. Immune-response induced by recombinant viruses
    g. FIPV deletion viruses serve as attenuated, live vaccines
  3. Insertion and expression of foreign genes
    a. Construction of recombinant viruses carrying reporter genes
    b. One-step growth of viruses
    c. Expression of renilla luciferase
  4. Generation of multivalent FIPV-based vaccines
    a. Construction of a multivalent Feline leukemia virus (FeLV) vaccine based on FIPV vector
    b. Construction of a multivalent Feline immunodeficiency virus (FIV) vaccine based on a FIPV vector
    c. Construction of a multivalent Feline calicivirus (FCV) vaccine based on a FIPV vector
    d. Construction of a multivalent Feline panleucopenia virus (FPV) vaccine based on a FIPV vector
    e. Construction of a multivalent Feline herpes virus (FHV) vaccine based on an FIPV vector
    f. Construction of a multivalent FIPV serotype I and II vaccine based on an FIPV serotype II vector
  5. Generation of recombinant viruses with rearranged gene order
  6. Generation of FIPV based vaccines against canine pathogens
    a. Generation of FIPV based vaccine against canine distemper
    b. Generation of FIPV based vaccine against canine parvo disease
    c. Generation of FIPV based vaccine against infectious canine hepatitis
    d. Generation of FIPV based vaccine against hemorrhagic disease of pups III. Transmissible gastro-enteritis virus (TGEV)
  1. Generation of a live attenuated vaccine against TGEV
  2. Generation of multivalent TGEV-based vaccines
    a. Construction of a multivalent Porcine Parvovirus (PPV) vaccine based on a TGEV vector
    b. Construction of a multivalent swine influenza virus vaccine based on a TGEV vector
    c. Construction of a multivalent African swine fever virus vaccine based on a TGEV vector
    d. Construction of a multivalent Porcine circovirus type 2 vaccine based on a TGEV vector
    e. Construction of a multivalent Porcine respiratory and reproductive syndrome virus vaccine based on a TGEV vector
  3. Generation of recombinant viruses with rearranged gene order IV. Avian Infectious Bronchitis Virus (IBV)
  1. Generation of a live vaccine based on attenuated IBV
  2. Generation of multivalent IBV-based vaccines
    aI. Construction of a multivalent vaccine based on an IBV vector that protects against more than one IBV serotype.
    aII. Construction of a multivalent vaccine based on an IBV vector that protects against Newcastle Disease.

b. Construction of a multivalent vaccine based on an IBV vector that protects against Avian Influenza.
c. Construction of a multivalent vaccine based on an IBV vector that protects against Chicken Anemia Virus (CAV) disease.
d. Construction of a multivalent vaccine based on an IBV vector that protects against Avian reovirus disease.
e. Construction of a multivalent vaccine based on an IBV vector that protects against Infectious Bursal Disease.
f. Construction of a multivalent vaccine based on an IBV vector that protects against Marek's disease.
g. Construction of a multivalent vaccine based on an IBV vector that protects against Infectious laryngotracheitis.
3. Generation of recombinant viruses with rearranged gene order V. Human Coronavirus (HCoV) strain 229E (HCoV-229E)
1. Generation of a live vaccine based on attenuated HCoV-229E
2. Generation of a live attenuated vaccine against HCoV strain OC43
3. Generation of multivalent HCoV-based vaccines
a. Construction of a multivalent vaccine based on an HCoV vector that protects against Respiratory Syncytial Virus (RSV)
b. Construction of a multivalent vaccine based on an HCoV vector that protects against rotavirus
c. Construction of a multivalent vaccine based on an HCoV vector that protects against Norwalk-like viruses
d. Construction of a multivalent vaccine based on an HCoV vector that protects against influenza virus
4. Generation of recombinant viruses with rearranged gene order

DETAILED DESCRIPTION OF THE INVENTION

I. Mouse Hepatitis Virus (MHV), Strain A59 (MHV-A59):

I.1 Generation of Live Attenuated Viruses:
General aim: establish whether deletion from the coronaviral (i.e. MHV-A59) genome of genes or gene clusters not belonging to the genes specifying the polymerase functions (ORF1a/1b) or the structural proteins N, M, E, and S, is tolerated and yields viable viruses even if these gene sequences are removed altogether; establish whether such deletions have an attenuating effect on the virus when inoculated into mice.

Figure 1A:
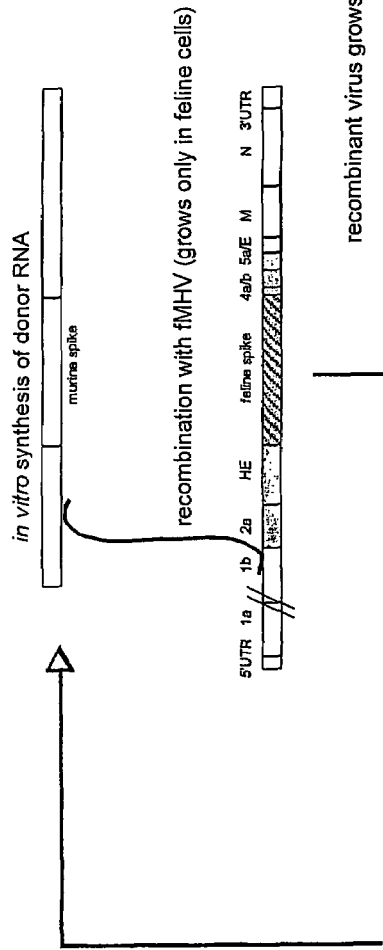
FIG. 1: A. The top part shows the principle of the RNA recombination technology. Feline cells are infected with fMHV (the MHV-derivative carrying a chimeric S protein with an ectodomain from the FIPV S protein allowing the virus to grow in feline cells) and transfected with synthetic donor RNA that carries, among others, the intact MHV S gene. Proper RNA recombination leads to viruses that have regained the ability to grow in murine cells by the acquisition of the cognate spikes. The lower part shows, on the left, the schematic representation of the relevant parts of the plasmid constructs from which donor RNAs were generated. On the right, the genomic organization of the recombinant viruses generated with these donor RNAs are depicted.
Figure 1B:
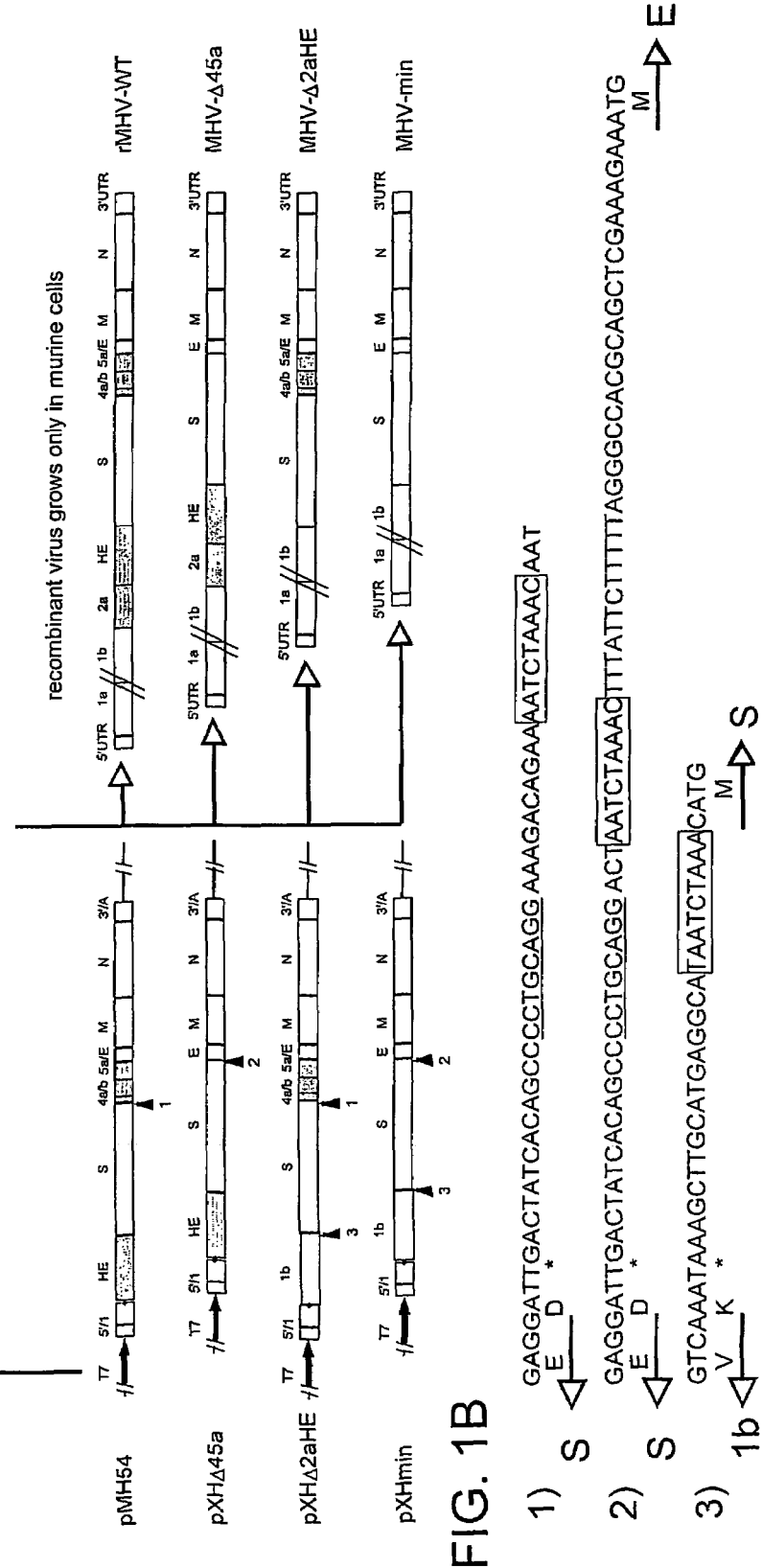

I.1.a. Construction of Recombinant MHVs Lacking Genes:
Specific aim: generate MHV-A59 deletion mutants lacking genes 2a+HE (MHV-□Δ2aHE) genes 4a+4b+5a (MHV-□Δ45a), and genes 2a+HE+4a+4b+5a (MHV-min).
Approach: targeted RNA recombination (3, 9, 10) using fMHV, the MHV-A59 derivative infecting feline (FCWF) cells not murine (LR7) cells (7), and synthetic donor RNAs carrying the intended deletions (FIG. 1A, top).
Procedure: Transcription vectors for the production of synthetic donor RNAs were constructed from the plasmid pMH54 (7), which encodes a run-off transcript consisting of the 5' end of the MHV-A59 genome (467 nt) fused to codon 28 of the HE gene and running to the 3' end of the genome (FIG. 1). Plasmid pMH54 was used to reconstruct the recombinant WT-MHV, an fMHV derivative again infecting murine cells. Transcription vector pXH□Δ45a lacks the ORFs 4a, 4b, and 5a. For the construction of this plasmid, a PCR product was obtained from plasmid pB59 (2) by using primer 1089 (5'-ACCTGCAGGACTAATCTAAACTTTAT-TCTTTTTAGGGCCACGA-3) (SEQ ID NO: 1), which encodes a PstI/Sse8387I restriction site, an intergenic sequence (IGS) and which is complementary to the sequence just upstream of the E or 5b gene, and primer 1092 (5'-CCTTAAGGAATTGAACTGC-3') (SEQ ID NO:2) which is complementary to the 5' end of the M protein coding region. The PCR product was cloned into pGEM-T Easy (Promega) according to the manufacturer's instructions, yielding pXH0803. The PCR product was subsequently excised with PstI and EcoRV and cloned into pMH54 treated with Sse8387I and EcoRV, resulting in pXH□Δ45a. Transcription vector pXH□Δ2aHE lacks ORFs 2a and HE and contains approximately 1200 bp of the 3' end of the polymerase gene fused to the S gene. To construct this plasmid a PCR product was obtained by splicing overlap extension PCR. One PCR product was obtained from plasmid p96 (1) using primer 1128 (5'-ACGGTCCGACTGCGCGCTTGAACACGTTG-3') (SEQ ID NO:3) which encodes a RsrII restriction site and is complementary to the region 1200 bp upstream of the ORF1b stop codon, and primer 1130 (5'-CATGCAAGCTT-TATTTGACATTTACTAGGCT-3') (SEQ ID NO:4) which is complementary to the 3' end of the polymerase coding region and the IGS region upstream of the S gene. The other PCR product was obtained from pMH54 using primer 1129 (5'-GTCAAATAAAGCTTGCATGAGGCATAAATCTAAAC-3) (SEQ ID NO:5) which is complementary to primer 1130, and primer 1127 (5'-CCAGTAAGCAATAATGTGG-3) (SEQ ID NO:6) which is complementary to the 5' end of the S gene. The PCR products were purified and mixed and then amplified with primers 1128 and 1127. The PCR product obtained in the second round of PCR was cloned into pGEM-T Easy, yielding pXH1802. The PCR product was excised with RsrII and AvrII and cloned into pMH54 treated with the same enzymes, resulting in pXHΔ□2aHE. Transcription vector pXHmin has the ORF1b 3' end fused to the S gene and the deletion of ORF4a, 4b and 5a. This vector was constructed by cloning the fragment excised with PstI and EcoRV from pXH0803 into pXH□2aHE treated with Sse8387I and EcoRV. The composition of all PCR-generated segments was confirmed by DNA sequencing.

To generate the deletion mutant viruses, donor RNAs were transcribed from the (PacI-linearized) pMH54-derived plasmids and transfected by electroporation into feline FCWF cells that had been infected with fMHV. These infected and transfected cells were then plated onto a monolayer of mouse LR7 (7) cells. After 24 hours of incubation at 37° C., progeny viruses were harvested by taking off the cell culture supernatant and candidate recombinants were selected by two rounds of plaque purification on LR7 cells.

Result: With each of the synthetic donor RNAs used, clear plaques were obtained.
Conclusion: Recombinant viruses had been obtained that had regained the ability to grow on murine cells.

I.1.b. Confirmation of the Recombinant Genotypes:
Aim: Confirming by RT-PCR, the genetic make-up of the recombinant viruses obtained.
Procedure and Results: Cloned recombinant viruses, one from each recombination experiment, were produced on LR7 cells, viral RNA was isolated and RT-PCR was done using standard methods on genomic RNA as shown in FIG. 2. To confirm the deletion of the ORFs 4 and 5a, the RT step was performed with primer 1092 (5'-CCTTAAGGAAT-TGAACTGC-3') (SEQ ID NO:2), which is complementary to the 5' end of the M gene, while the PCR was performed with primer 1261 (5'-GCTGCTTACTCCTATCATAC-3') (SEQ ID NO:7) and primer 990 (5'-CCTGATTTATCTCTCGATTTC-3) (SEQ ID NO:8) which are complementary with the 3' end of the E and S gene, respectively. In the case of the recombinant MHV-WT, an RT-PCR product corresponding in size with the expected 1328 bp was observed (FIG. 2, top). As expected, a PCR product of the same length was observed for MHV-Δ☐2aHE. In contrast, both for MHV-☐Δ45a and MHV-min much smaller RT-PCR products were detected. The smaller size of the RT-PCR products corresponded with the deletion of 736 bp. The deletion of ORFs 2a and HE was analyzed in a similar way. The RT step was performed with primer 1127 (5'-CCAGTAAGCAATAATGTGG-3) (SEQ ID NO:6) which is complementary to the 5' end of the S gene. The PCR was performed with primer 1173 (5'-GACT-TAGTCCTCTCCTTGA-3') (SEQ ID NO:9) and primer 1260 (5'-CTTCAACGGTCTCAGTGC-3) (SEQ ID NO:10), which are complementary to the 3' end of the 1b gene and the 5' end of the S gene, respectively. Both for MHV-WT and MHV-☐Δ45a PCR products were detected, which were much bigger than the PCR products detected for MHV-Δ2aHE and MHV-min (FIG. 2, bottom). The difference in size corresponded with the deletion of 2164 bp. Finally, the newly generated junctions, present in the genomes of the deletion mutant viruses (FIGS. 1A [triangles] and 1B [sequence]), were analyzed by sequencing of the RT-PCR products. To this end the PCR products were cloned into the pGEM-T easy vector (Promega). The sequences obtained were in perfect agreement with the predictions.

Conclusion: The constructed viral mutants had the intended genetic deletions.

I.1.c. RNA Synthesis by MHV Deletion Mutants:

Aim: Confirming the patterns of RNAs synthesized in cells infected by the mutant viruses.

Procedure: Infected 17Cl1 cells were metabolically labeled with [$^{33}$P]orthophosphate in the presence of actinomycin D essentially as described (4, 10). Samples of total cytoplasmic RNA, purified using Ultraspec reagent (Biotecx), were denatured with formaldehyde and formamide, separated by electrophoresis through 1% agarose containing formaldehyde, and visualized by fluorography (FIG. 3; note that the subgenomic RNA species in this figure are designated by their composition, rather than as RNA2 through RNA7, since the numerical designations would be ambiguous for the deletion mutants).

Result: For the recombinant MHV-WT, the RNA pattern and the relative molar amounts of the six subgenomic (sg) RNA species and the genomic (g) RNA were very similar to those reported previously for MHV (10)(4)(5)(8), with one notable exception. The 4-5a/E-M-N sgRNA, which is usually denoted RNA4, was far more abundant than previously observed for this species in wild-type MHV (10)(4)(5)(8). This was presumably due to the three nucleotide changes at positions 13, 15, and 18 upstream of the consensus transcription regulatory signal, (5'-AAUCUAAAC3-') (SEQ ID NO:11) that precedes gene 4 (FIG. 1) which were introduced into the transcription vector pMH54 to create the Sse8387I site downstream of the S gene (7). For the deletion mutants, all variant sgRNAs had mobilities that corresponded to their predicted sizes (FIG. 3 and Table 3), and no prominent extra species were observed. The relative molar amounts of the mutant sgRNA species were quite similar to those of their wild-type counterparts originating from the corresponding transcription regulatory signals.

Conclusion: The results confirm the genotypes of the recombinant viruses and demonstrate their expected phenotypes at the RNA level.

I.1.d. Tissue Culture Growth Phenotype:

Aim: Comparing the in vitro growth phenotypes.

Procedure and Results: Confluent LR7 cell monolayers grown in 35-mm dishes were infected with each recombinant virus (8 PFU/cell) and viral infectivity in culture media at different times post-infection (p.i.) was determined by titration on LR7 cells. TCID$^{50}$ (50% tissue culture infective doses) values were calculated and plotted (FIG. 4). The recombinant viruses did not differ appreciably with respect to the induction of extensive syncytia or cytopathic effects or in their plaque size. However, MHV-☐Δ45a and MHV-min differed from MHV-WT and MHV-☐Δ2aHE in their one-step growth kinetics (FIG. 4). The two viruses displayed approximately 10-fold lower titers at all time points.

Conclusion: All deletion viruses multiply well in vitro although the deletion of genes 4 and 5a had a slightly negative effect.

I.1.e. Virulence of Recombinant Viruses in Mice:

Aim: Establishing whether the genetic deletions affect viral virulence.

Procedure and Results: The recombinant viruses were characterized in their natural host, the mouse. As a first step, we determined the virulence of the recombinant viruses. An LD$^{50}$ (50% lethal dose) assay was carried out by inoculating MHV-negative, C57B1/6 mice intracranially with four 10-fold serial dilutions ($5 \times 10^{5}$–$5 \times 10^{2}$) of recombinant viruses. Viruses were diluted using PBS containing 0.75% bovine serum albumin. A volume of 25 µl was used for injection into the left cerebral hemisphere. Five animals per dilution per virus were analyzed. LD$^{50}$ values were calculated by the Reed-Muench method based on death by 21 days post-infection. Clearly, deletion mutant viruses were attenuated when compared to the recombinant MHV-WT. While the MHV-WT virus had an LD$^{50}$ of $1.8 \times 10^{4}$ no LD$^{50}$ could be derived for the deletion mutants. Although the animals inoculated with the higher doses showed some signs of illness, none of the animals infected with any of the deletion mutant viruses died up to input of 50,000 PFU/mouse. This implies that the LD$_{50}$ for these viruses exceeds a value of 50,000 and may well be above 100,000.

FIG. 25 illustrates the kinetics of mortality of mice infected with the highest inoculation dose, $2.5 \times 10^{5}$ plaque forming units (PFU), of WT and deletion viruses. While all the animals inoculated with wild type virus had died by seven days post infection, the deletion viruses were highly attenuated, displaying no death and less severe clinical symptoms. Despite the observation of no mortality, all mice infected with the ☐45a and ☐2aHE viruses showed clinical signs of hunched posture, disheveled appearance and waddling gait during the first weekpost-infection; these symptoms were less severe and observed in fewer mice infected with MHV-min.

Conclusion: Viruses with deletions of the sequences specifying the genes 2a+HE or genes 4a+4b+5a or of the combination of all these genes exhibit a significantly attenuated phenotype in mice. In other words, the nonessential genes of coronaviruses are not crucial for in vitro growth but determine viral virulence. The attenuation acquired by their deletion thus provides excellent viral vaccines and therapeutic vectors.

I.2. Generation of Recombinant Viruses with Rearranged Gene Order:

General aim: establish whether the invariable order of the genes specifying the polymerase functions (ORF1a/1b) and the structural proteins S, E, M, and N in the coronaviral genome is essential for the viability of these viruses or whether rearrangement of this order is tolerated.

I.2.a. Construction of Recombinant Viruses with Rearranged Gene Order:

Specific aim: generate MHV-A59 mutants in which the relative positions of structural protein genes in the MHV-A59 genome are changed by moving the M and/or E gene.

Approach: targeted RNA recombination using fMHV and synthetic donor RNAs carrying the intended rearrangements (FIG. 5, top).

Procedure: Transcription vectors for the production of donor RNA for targeted recombination were constructed from plasmids pMH54 and pXH☐2aHE (described above). In order to generate transcription vector pXHSM45N (FIG. 5, lower left part), a PCR product was generated by splicing overlap extension (SOE)-PCR that contained the 3' end of the M gene and the 5'end of the N gene and in which a EcoRV restriction site was introduced between the M gene and IGS just upstream of the N gene. To generate this PCR fragment, outside primer 1C (5'-GTGTATAGATATGAAAGGTAC-CGTG-3') (SEQ ID NO:12) corresponding to the region of the M gene that contains the unique KpnI site, and outside primer 1097 (5'-CGAACCAGATCGGCTAGCAG-3') (SEQ ID NO:13), corresponding to the region of the N gene that contains the unique NheI site, were used. Primer 1095 (5'-AGATTAGATATCTTAGGTTCTCAACAATGCGG-3) (SEQ ID NO:14) and primer 1096 (5'-GAACCTAA-GATATCTAATCTAAACTTTAAGGATG-3') (SEQ ID NO:15) were used as inside primers. They correspond to the sequence between the M and the N gene and introduce the EcoRV restriction site. The resulting PCR product was cloned into pGEM-T easy (Promega) yielding vector pXH0302. As a next step in the construction of pXHSM45N, pMH54 was treated with the restriction enzymes Sse8387I and EcoRV and the resulting fragment was cloned into the EcoRV site of pXH0302 after being blunted by T4 DNA polymerase treatment, yielding vector pXH0902. After excision of the Sse8387I-EcoRV fragment of pMH54, the remaining vector was also blunted by T4 DNA polymerase treatment and religated resulting in plasmid pXH1401. Finally, plasmid pXH0902 was treated with restriction enzymes NheI and BssHII and the resulting fragment was cloned into pXH1401 treated with the same enzymes, yielding pXHSM45N.

For the construction of pXHMSmN, first the ORFs 4, 5 and M were removed from pMH54 by restriction of this vector with enzymes Sse8387I and BssHII, followed by treatment with T4 DNA polymerase and religation of the remaining vector, which yielded pXH☐45M5'. Next, the fragment resulting from treatment of pXH0302 with enzymes NheI and BssHII was cloned into pMH54 treated with the same enzymes, resulting in pXHMeN. Subsequently, the fragment obtained after restriction of pXHMeN with EcoRV was cloned into pXH1802 (described above), which was digested with HindIII and treated with Klenow fragment of DNA polymerase I, yielding pXH0305B. The fragment obtained by restriction of pMH54 with enzymes MluI and EcoRV was cloned into pB59 (2) treated with the same enzymes, which resulted in vector pXH2801. Next, the fragment resulting from the treatment of pXH2801 with restriction enzymes KpnI and PstI was treated with T4 DNA polymerase and cloned into pXH1802 treated with restriction enzyme HindIII and with Klenow fragment of DNA polymerase I, yielding pXH0806. Subsequently, the fragment obtained by digestion of pXH0305B with SpeI and AflII was cloned into pXH0806 treated with the same enzymes, resulting in pXH1506. Finally, pXHSmN was obtained by cloning the fragment resulting from restriction of pXH1506 with RsrII and AvrII into pXH☐45M5' treated with the same enzymes.

For the construction of transcription vector pXH1bMS, vector pXHMeN was restricted with EcoRV. The resulting fragment was removed and the vector was religated yielding pXH☐M. Next, the fragment obtained by digestion of pXH0305B with RsrII and AvrII was cloned into pXH☐M treated with the same enzymes, yielding pXH1bMS.

All constructs were confirmed by restriction and/or sequence analysis. They are depicted schematically in FIG. 5 (left). All new junctions generated, including the introduction of the Sse8387I site downstream of the S gene in pMH54 (7), are indicated with arrowheads, while their sequences are shown in Table 1. Recombinant viruses were generated by RNA-RNA recombination between transcription vector run-off transcripts and the fMHV genome as described above. After 2 rounds of plaque purification on LR7 cells the viruses were analyzed by reverse transcriptase-PCR on genomic RNA and found to contain the genomes with the expected organization.

Conclusion: The strict gene order of the coronaviruses is not an essential prerequisite for viability.

I.2.b. RNA Synthesis by MHV Mutants with Rearranged Gene Order:

Aim: Confirming the patterns of RNAs synthesized in cells infected by the mutant viruses.

Figure 26A:
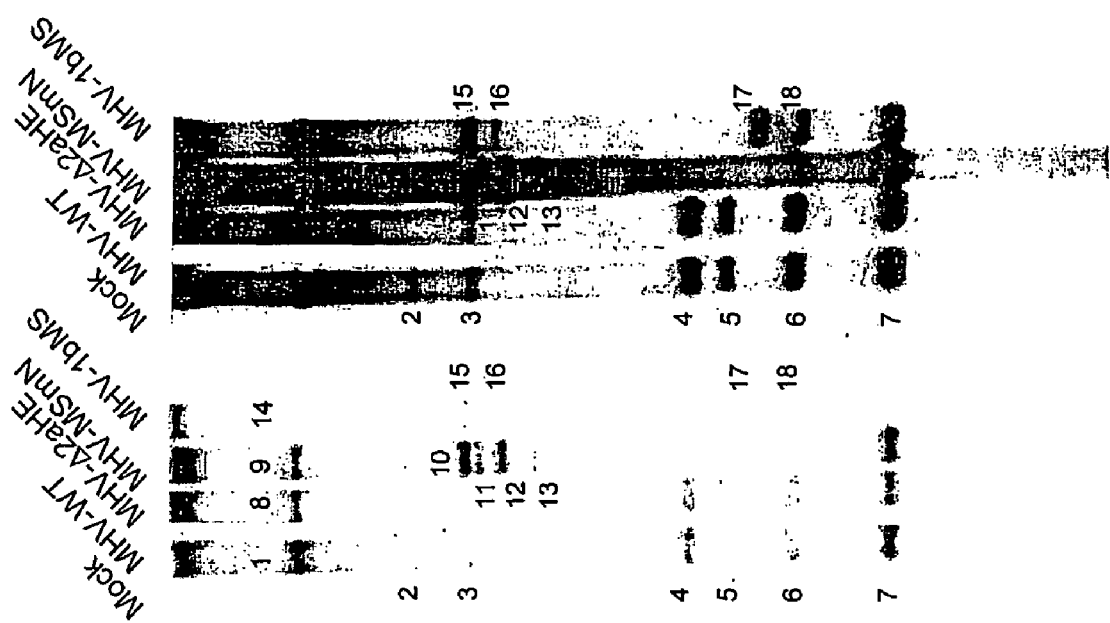

Procedure: Infected 17Cl1 cells were metabolically labeled with [$^{33}$P]orthophosphate in the presence of actinomycin D essentially as described (4, 10). Samples of total cytoplasmic RNA, purified using Ultraspec reagent (Biotecx), were denatured with formaldehyde and formamide, separated by electrophoresis through 1% agarose containing formaldehyde, and visualized by fluorography (FIG. 26A).

Result: Coronaviruses express their genome via the generation of a 3' co-terminal nested set of sg RNAs. Recombinant viruses with a rearranged genome organization are therefore predicted to synthesize patterns of viral RNAs that are distinctly different from that of the parent virus. For the reconstructed wild-type virus (MHV-WT) and for MHV-☐2aHE, the RNA patterns and the amounts of the genomic (g) and sg RNA species appeared to be similar to those observed previously (FIG. 3). Note that MHV-☐2aHE—as well as its derivatives MHV-MSmN and MHV-1bMS—does not synthesize the sg RNA species encoding the 2a protein. For the MHV mutants with the rearranged genomes, all variant sg RNAs had mobilities that corresponded to their predicted sizes (FIG. 26A and Table 4), and no obvious additional species were observed. MHV-SM45N grew very poorly, and was therefore labeled only weakly. All sg RNAs could be detected except the one from which the M protein should be translated. The low abundance of this sg RNA, the reason of which is unknown, is likely to be the cause of the impaired growth of this virus. Overall, the patterns of viral RNAs synthesized by the cells infected with the recombinant viruses nicely reflect the changes made to the coronavirus genome organization.

Conclusion: The results confirm the genotypes of the recombinant viruses and demonstrate their expected phenotypes at the RNA level.

I.2.c. Tissue Culture Growth Phenotype:

Aim: Comparing the in vitro growth phenotypes of the mutant viruses.

Procedure and Results: Confluent LR7 cell monolayers grown in 35-mm dishes were infected with each recombinant virus (8 PFU/cell) and viral infectivity in culture media at different times post-infection was determined by titration on LR7 cells. TCID$^{50}$ values were calculated and plotted (FIG. 6). All viruses except the mutant MHV-SM45N were analyzed in this way. The infectious titer of this latter virus was too low (approximately 1000 times lower than the WT recombinant MHV) to perform a one-step growth curve. Although MHV-1bMs appeared to induce syncytia somewhat slower than the WT recombinant, all viruses replicated approximately to the same extent in the one-step growth curve.

Conclusion: Except for mutant virus MHV-SM45N, the gene rearrangement had no dramatic effect on their in vitro growth characteristics.

I.2.d. Replication of Recombinant Viruses in Mice:

Aim: Establishing whether viruses with rearranged gene order are able to replicate in mice.

Figure 26B:
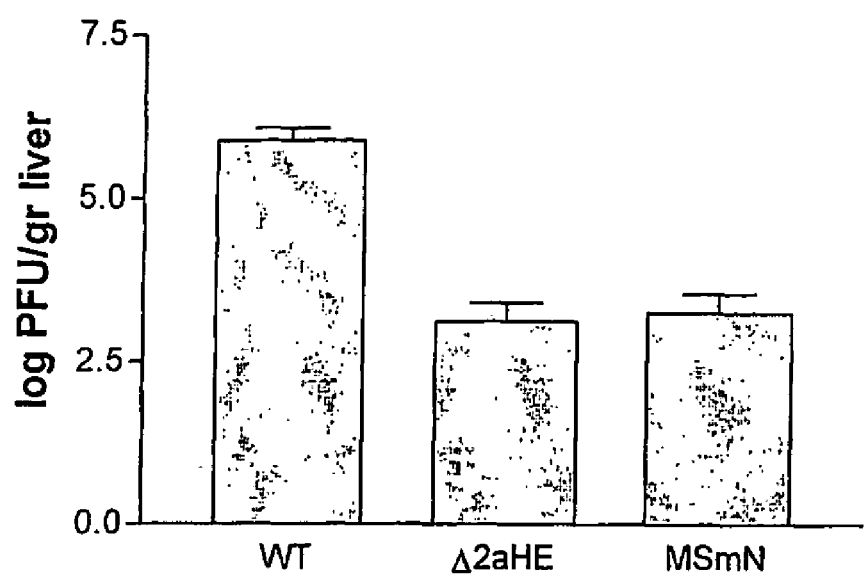

Procedure and Results: Eight week old, MHV-negative, female BALB/c mice were used in the experiment. Viruses were diluted in PBS and a total volume 100 μl ($10^6$ $TCID^{50}$) was used for injection in the peritoneal cavity. Four animals per virus were inoculated. Mice were sacrificed and the livers were removed at day 4 post-infection. The livers were placed in 1.5 ml DMEM, weighed and then frozen at −80° C. until tittered for virus. Virus titers were determined by plaque-assay on LR7 cell monolayers following homogenization of the organs. The replication of MHV-WT, MHV-□2aHE and MHV-MSmN was studied in their natural host, the mouse. While the 50% lethal dose of MHV-WT in mice was previously determined at $2.7\times10^4$ PFU, MHV-□2aHE was not virulent enough for a 50% lethal dose value determination (section I.1.e.). Therefore, we now decided to analyze the in vivo replication of the recombinant viruses. Mice inoculated intraperitoneally with $1\times10^6$ $TCID^{50}$ were euthanized at day 4 post-infection and the viral replication in the liver was determined. The results are shown in FIG. 26B. MHV-U□2aHE and MHV-MSmN replicated in the liver to a similar extent albeit much lower than MHV-WT. Deletion of ORFs 2a and HE generated a recombinant virus (MHV-□2aHE) that was attenuated in the natural host, as shown in section I.1.e., while additional rearrangement of the coronavirus gene order (MHV-MSmN) did not result in a more attenuated phenotype in this assay.

Conclusion: Viruses with a rearranged gene order, which lack the typical coronavirus genome organization, and viruses that lack ORFs 2a and HE are able to replicate in their natural host, the mouse.

I.3. Generation of Recombinant Viruses Expressing Foreign Genes:

Aim: Establish whether foreign genes can be inserted at different positions in the viral genome, either as an additional gene or replacing deleted nonessential genes or in combination with a rearranged gene order; establish whether these genes are expressed and whether they are stably maintained during in vitro passage of the virus.

I.3.a. Construction of Recombinant Viruses Carrying Reporter Genes:

Aim: Generate MHV-A59 viruses with foreign gene insertions.

Procedure: Several viruses were constructed containing a foreign reporter gene in their genome at different positions (see FIG. 7A). Two reporter genes were used, encoding renilla luciferase (RL) and firefly luciferase (FL). For both genes, a plasmid was constructed in which the gene was preceded by the MHV intergenic sequence (IGS). From this construct the expression cassette (gene plus IGS) could then be transferred into the different transcription vectors.

Figure 27:
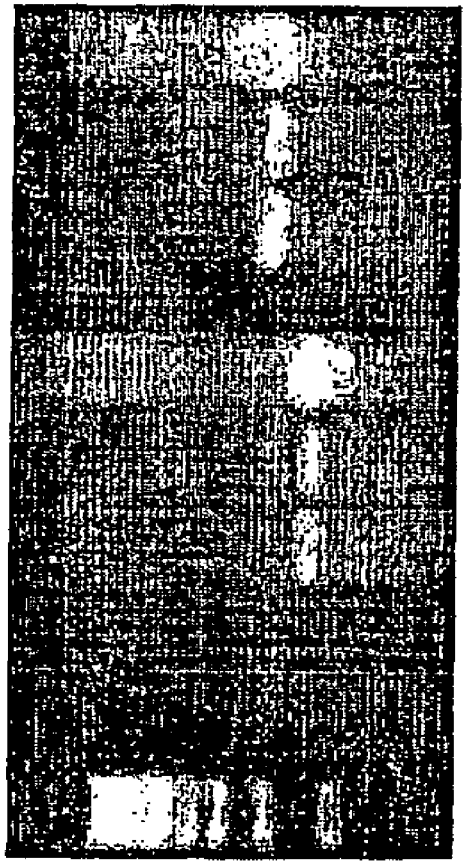

As a first step, the MHV IGS was cloned in front of the RL gene. To this end, primer 1286 (5'-GGATACTAATCTAAACTTTAG-3') (SEQ ID NO:16) and 1287 (5'-CTAGCTAAAGTTTAGATTAGATATCCTGCA-3') (SEQ ID NO:17) were annealed to each other and cloned into pRL-null (Promega) treated with NheI and PstI, resulting in pXH1909. For the construction of the transcription vector containing the RL gene between genes 2a and S (pXH22aRLS), the following steps were taken. Vector $p^{96}$ (1) was restricted with HindIII and MluI and the resulting fragment was cloned into pXH1802 (described above) treated with HindIII and BssHII, yielding pXH2103. Next, the RL expression cassette was removed from pXH1909 by restriction with EcoRV and XbaI, treated with Klenow fragment of DNA polymerase I and cloned into pXH2103 digested with HindIII and treated with Klenow fragment, resulting in pXH2509A. Finally, pXH22aRLS was constructed by cloning the fragment resulting from digestion of pXH2509A with RsrII and AvrII into pMH54 treated with the same enzymes.

For the construction of pXH2ERLM the same expression cassette that was used to make pXH2509A, was cloned into pMH54 digested with EcoRV.

This same expression cassette was also cloned into pXH-MeN (described above) treated with EcoRV, yielding pXH2ERLN. Subsequently, pXH2MRLN was constructed by cloning the fragment resulting from restriction of pXH-MeN with EcoRV into pXH2ERLN treated with the same enzyme. pXHMSmNRL was constructed by cloning the renilla expression cassette into pXHMSmN (described above) treated with EcoRV.

For the construction of pXHEFLM, the FL gene was first cloned behind the same IGS as was used for the RL expression cassette. To this end, the luciferase gene was removed from pSP-Luc+ (Promega) by restriction with AvrII and XbaI and cloned into pXH1909 treated with NheI and XbaI, yielding pXH2711. Subsequently, the FL expression cassette was cut out of pXH2711 by restriction with EcoRV and XbaI, treated with Klenow fragment of DNA polymerase I, and cloned into pMH54 restricted by EcoRV, resulting in pXHE-FLM.

Plasmid pXHminFL was constructed by cloning the FL expression cassette into pXHmin (described above) digested with EcoRV. This plasmid lacks ORFs 2a/HE/4a/4b/5a and contains the FL gene between genes E and M.

After confirmation of all constructs by restriction and sequence analysis, recombinant viruses were generated by RNA-RNA recombination between transcription vector run-off transcripts and the fMHV genome as described above. The resulting viruses were genetically confirmed by RT-PCR analysis.

Results of recombinant viruses containing the RL gene are shown in FIGS. 7B and 27. To confirm the insertion of this gene an RT step was performed on genomic RNA with primer 1412 (5'-CTGCGGACCAGTTATCATC-3') (SEQ ID NO:18) which is complementary to the 5' end of the RL gene. Subsequently, a PCR was performed with primer 1091 (5'-GTTACAAACCTGAATCTCATCTTAATTCTGGTCG-3') (SEQ ID NO:19) and primer 1413 (5'-CATCCGTTTCCTTTGTTCTGG-3) (SEQ ID NO:20) for MHV-ERLM and MHV-MRLN or with primer 1173 (5'-GACTTAGTCCTCTCCTTGATTG-3) (SEQ ID NO:21) and primer 1413 for MHV-2aRLS.

Primer 1091 and primer 1173 correspond with the 3' end of gene 4b and gene 1b, respectively, while primer 1413 corresponds with the 5' end of the RL gene. As positive controls, the appropriate transcription vectors were taken along. In all cases, PCR fragments were obtained of the same size as the positive controls, while the water control was negative. The observed (and predicted) fragment sizes were approx. 1,000 bp for MHV-2aRLS, approx. 670 bp for MBV-ERLM, and approx. 1,300 bp for MHV-MRLN (7B). For MHV-MSm-NRL a PCR was performed with primer 1091 and primer 1413 and with primer 1173 and primer 1413. As positive controls, the appropriate transcription vector was taken along. In all cases, PCR fragments were obtained of the same size as the positive controls. The observed (and predicted) fragment sizes were approx. 670 bp for the PCR reaction with primers 1091 and 1413, and approx. 1,200 bp for the PCR reaction with primers 1173 and 1413 (7B) (note that in FIGS. 7B and 27 for each type of virus 2 independently obtained, viral clones were analyzed and included). The results confirmed the insertion of the RL gene into the MHV genome at the correct position.

Figure 28:
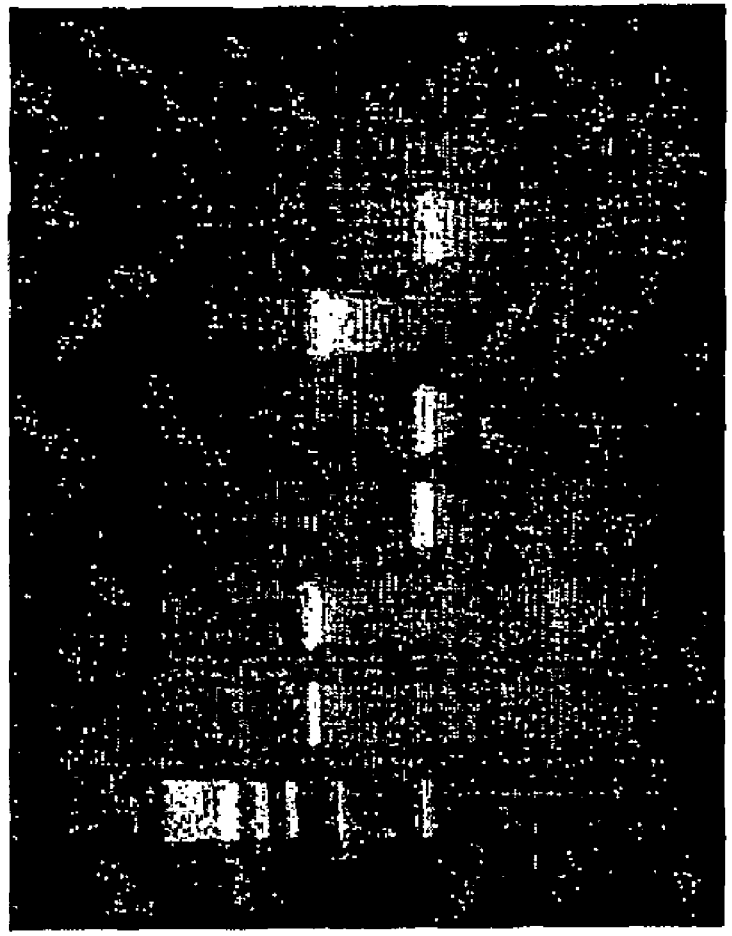
Figure 29:
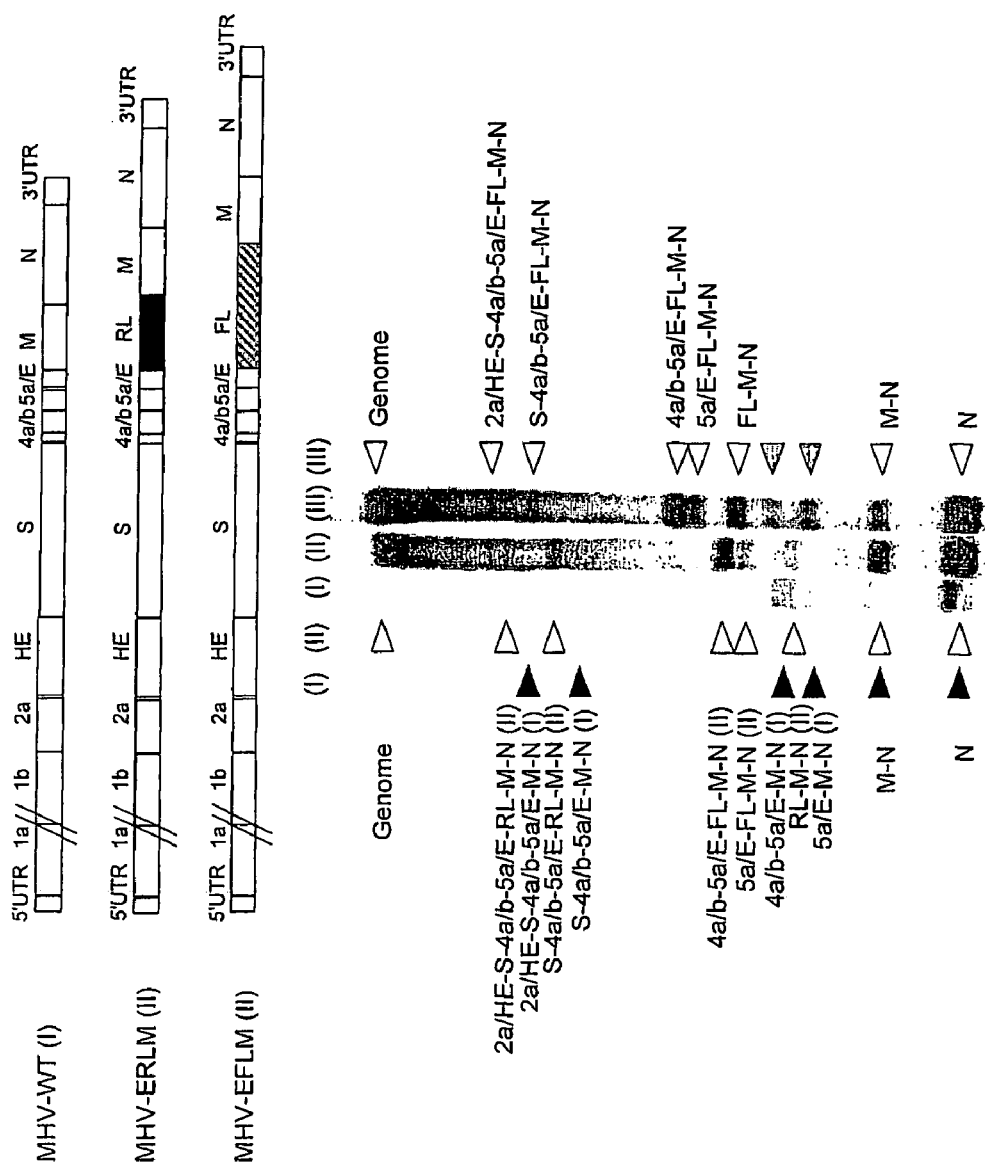
Figure 30:
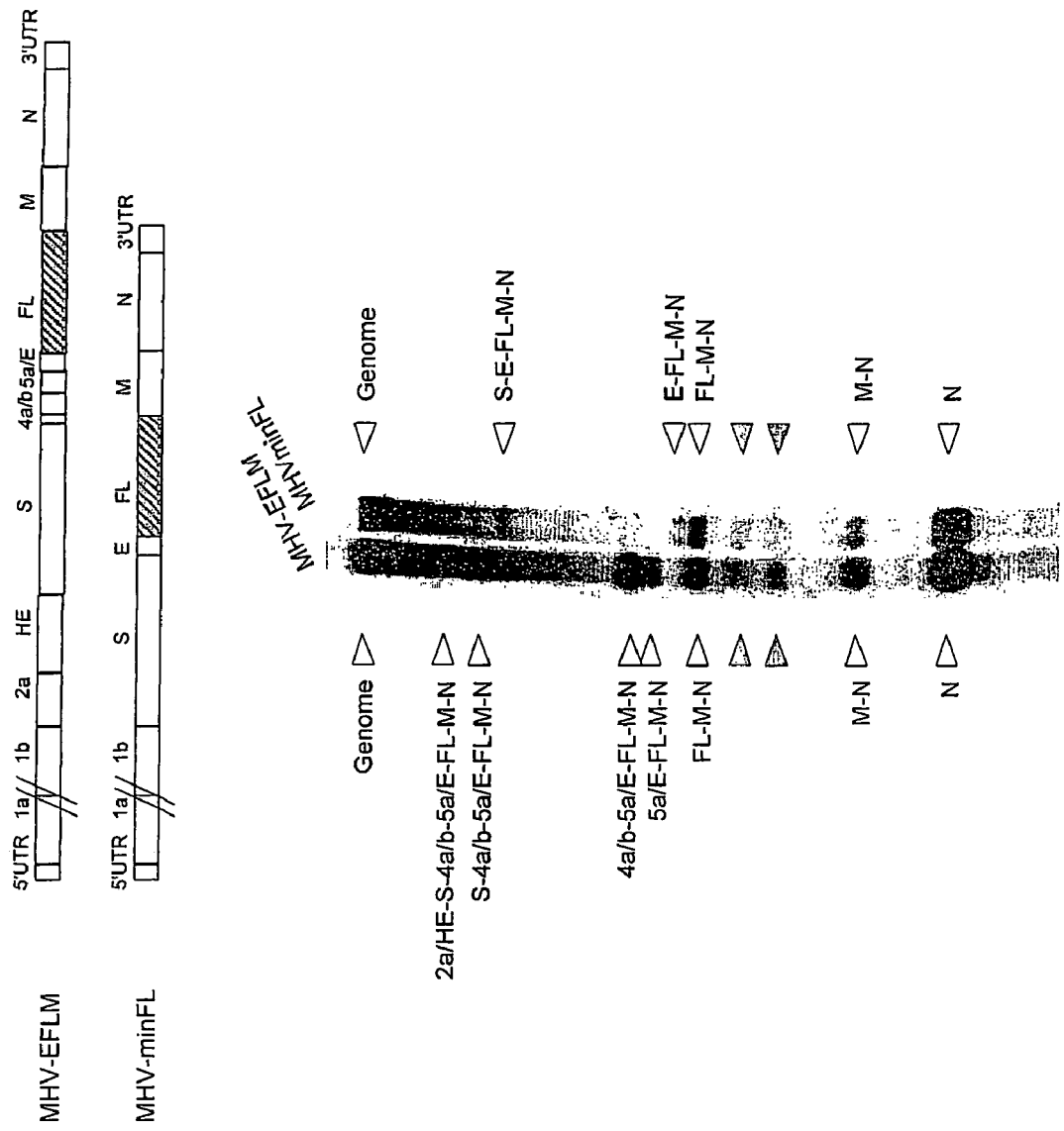
Figure 31:
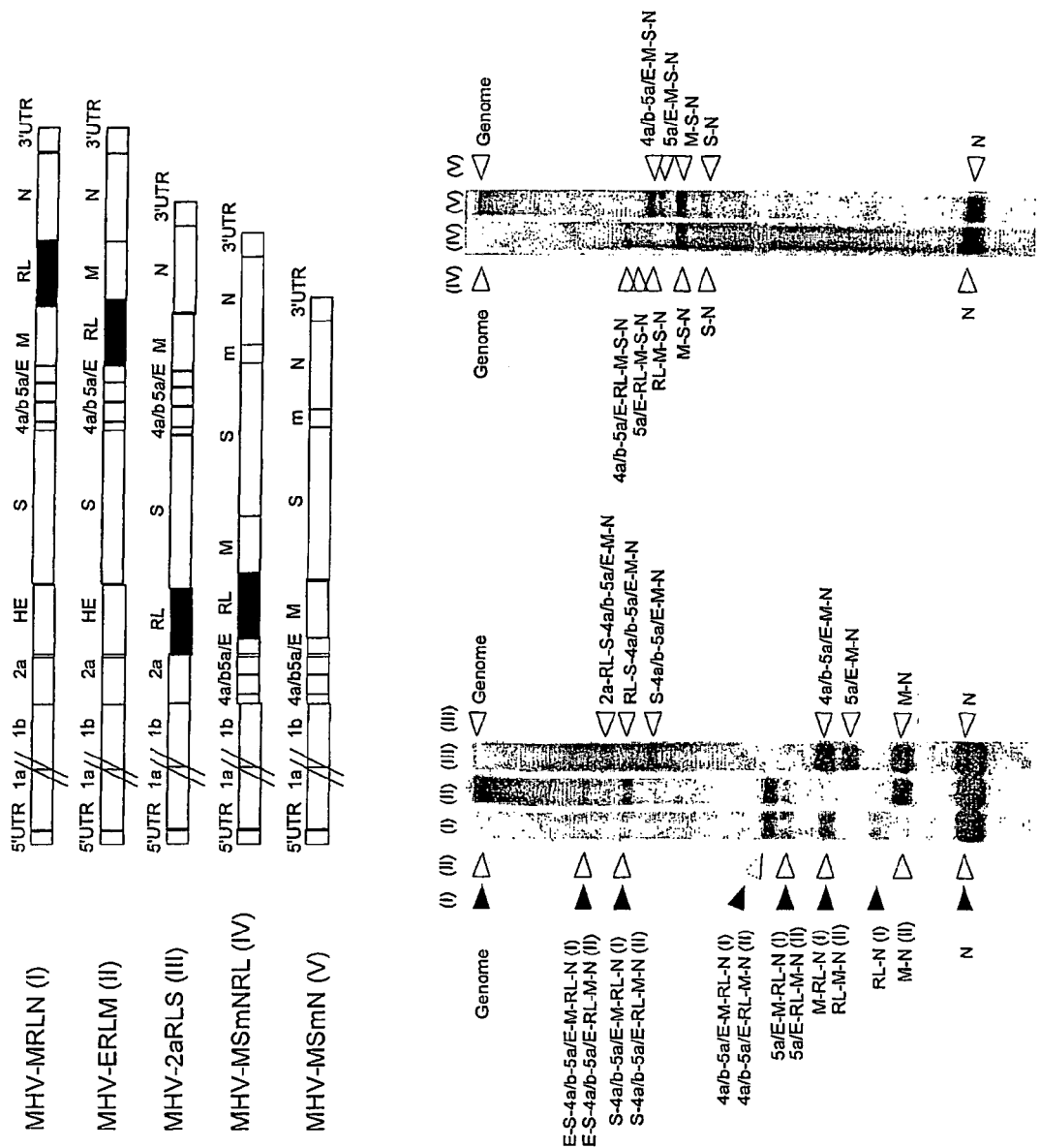

Results of recombinant viruses containing the FL gene are shown in FIG. 28. To confirm the insertion of this gene an RT step was performed on genomic RNA with primer 1475 (5'-GCCTAATGCAGTTGCTCTCC-3) (SEQ ID NO:22) which is complementary to the 5' end of the FL gene. Subsequently, a PCR was performed with primer 935 (5'-GTTTTAGCACAGGGTGTGGCTCATG-3) (SEQ ID NO:23), which corresponds with the 3' end of the S gene, and primer 1474 (5'-CCATCTTCCAGCGGATAG-3) (SEQ ID NO:24), which corresponds with the 5' end of the FL gene. As positive controls, the appropriate transcription vectors were taken along. In all cases, PCR fragments were obtained of the same size as the positive controls, while the water control was negative. The observed (and predicted) fragment sizes were approx. 1,200 bp for MHV-EFLM, and approx. 500 bp for MHV-minFL (note that in FIG. 28 for each type of virus 2 independently obtained, viral clones were analyzed and included).

Conclusion: Insertion of genetic modules into the coronaviral genome is tolerated at all positions tested; all the intended viruses were viable.

I.3.b. RNA Synthesis by Recombinant Viruses:

Aim: Confirming the patterns of RNAs synthesized in cells infected by the mutant viruses.

Procedure: Infected 17Cl1 cells were metabolically labeled with [$^{33}$P]orthophosphate in the presence of actinomycin D essentially as described (4, 10). Samples of total cytoplasmic RNA, purified using Ultraspec reagent (Biotecx), were denatured with formaldehyde and formamide, separated by electrophoresis through 1% agarose containing formaldehyde, and visualized by fluorography (FIGS. 29-31; note that the subgenomic RNA species in this figure are designated by their composition, rather than as RNA2 through RNA7, since the numerical designations would be ambiguous for the mutants).

Result: For all the MHV mutants with the luciferase genes, all variant sg RNAs had mobilities that corresponded to their predicted sizes (FIGS. 29-31). For the viruses containing the renilla luciferase gene no obvious additional species were observed.

For the viruses containing the firefly luciferase gene two additional RNA species were observed, which correspond in size with transcription of sgRNAs from sequences in the firefly luciferase gene that are similar to the MHV IGS. Overall, the patterns of viral RNAs synthesized by the cells infected with the recombinant viruses nicely reflect the insertion of the luciferase expression cassettes into the coronavirus genome.

Conclusion: The results confirm the genotypes of the recombinant viruses and demonstrate their expected phenotypes at the RNA level.

I.3.c. Replication of Viruses Expressing Renilla or Firefly Luciferase:

Aim: Compare the growth characteristics of the viruses with wild-type virus and with each other.

Procedure and Results: After two rounds of plaque purification virus stocks were prepared, titrated and used for high m.o.i (m.o.i. of 8) infection of LR7 cells after which the viral infectivities in the culture media were monitored. The results are represented by the growth curves shown in FIGS. 8A and 8B, and by the results shown in FIG. 32. Of MHV-EFLM two viral clones, independently obtained from the recombination experiment described under I.3.a, were analyzed. In FIG. 32, the $TCID^{50}$ values obtained at 8-9 hours post-infection are shown. Obviously, the growth characteristics of the recombinant viruses shown in FIGS. 8A and 8B are essentially indistinguishable; all viruses grew to titers that were comparable to that of recombinant wild-type virus. MHV-MSmNRL reached somewhat lower titers (FIG. 32).

Conclusion: The inserted expression cassettes hardly affected the in vitro growth characteristics of the recombinant viruses.

I.3.d. Expression of Renilla and Firefly Luciferase in Cell Culture:

Aim: Establish whether the inserted expression cassettes were functional.

Procedure and Results: Confluent monolayer cultures of LR7 cells were infected at an m.o.i. of 8 and the production of luciferase activity in the cells was monitored over time. RL expression in cells was measured by using the Dual-Luciferase Reporter Assay System (Promega) according to the manufacturer's instructions. Similarly, FL expression was measured by using the Luciferase Assay System (Promega) according to the manufacturer's instructions. RL and FL activity was measured in relative light units (RLU) using a luminometer (Lumac Biocounter M2500 or Turner Designs Model TD-20/20).

The results are shown graphically in FIGS. 9A, 9B and 33. All recombinant viruses except for the recombinant wild-type virus expressed high levels of luciferase, indicating that both the renilla and the firefly luciferase gene cassettes were functional at each genomic position tested. For most viruses, the highest expression level was reached at 9 hours post-infection. The expression level of firefly luciferase at this time-point was determined at 1.6 ug/$10^6$ cells. MHV-minFL expressed levels of luciferase activity that were comparable to those produced by the other recombinant viruses containing the FL gene, while expression of the renilla luciferase gene in cells infected with MHV-MSmNRL was approx. 10-fold lower than in cells infected with MHV-ERLM. This difference corresponds with the difference found in replication between MHV-MSmNRL and MHV-ERLM.

Conclusion: Foreign genes can be expressed by coronaviruses both by the additional insertion of such a gene, by using the genetic space created by deletion of nonessential genes, or in combination with a rearranged genome organization.

I.3.e. Maintenance of Foreign Genes During Viral Passage:

Aim: Evaluate the stability of the inserted luciferase genes during viral passage.

Procedure and Results: The recombinant viruses MHV-ERLM and MHV-EFLM were passaged 8 times over LR7 cells at low m.o.i. (<0.05). After each passage, the viral infectivity ($TCID^{50}$) in the culture medium at 9 hours post-infection was determined. Subsequently, the firefly and renilla luciferase activity was determined in a parallel expression experiment (m.o.i.=5) at 8 hours post-infection (FIG. 10). Both of MHV-ERLM and of MHV-EFLM two independently obtained clones A and B were analyzed. While the renilla luciferase expression was consistently stable for at least 8 passages, that of the firefly luciferase was stable only for 5 passages. After passage 5 of MHV-EFLM, the expression level clearly decreased for both independent clones. After 8 passages, 10 viral clones were isolated by plaque assay both of MHV-ERLM and of MHV-EFLM and tested for luciferase expression. While for MHV-ERLM all 10 clones were positive, 9 of the MHV-EFLM clones no longer showed clearly detectable luciferase expression.

Conclusion: A foreign gene can be stably maintained in the coronaviral genome for at least 8 passages in vitro.

I.3.f. Expression of Firefly Luciferase in Mice:

Aim: Establish whether the inserted luciferase gene is expressed in the natural host, the mouse.

Figure 34:
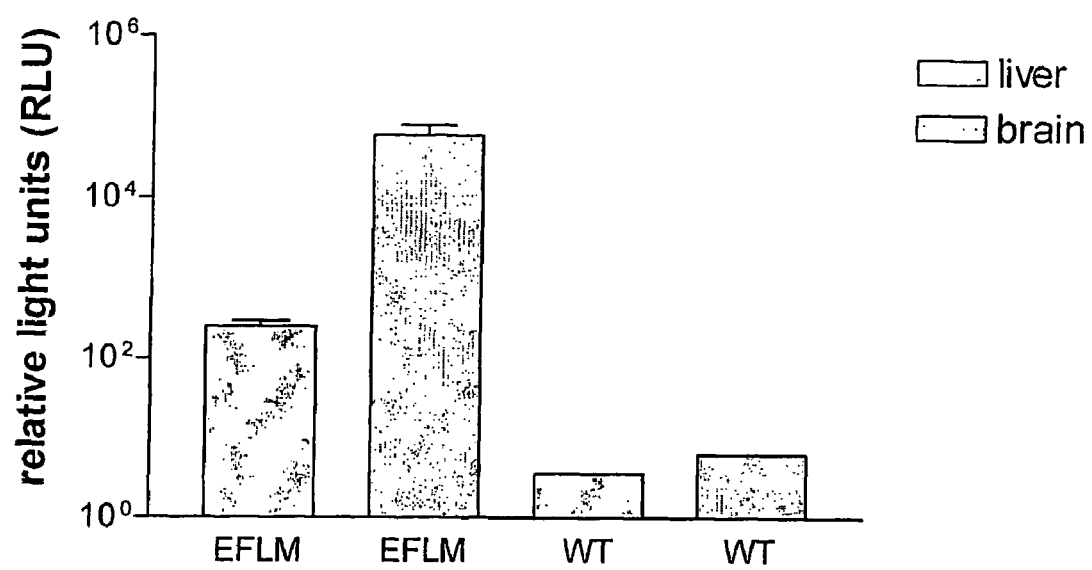

Procedure and Results: Eight weeks old, MHV-negative, female BALB/c mice were used in the experiment. Mice were inoculated intranasally with $10^6$ $TCID^{50}$ MHV-EFLM. Four animals per virus were used. Mice were sacrificed and the livers and brains were removed at day 4 post-infection. Organs were quick-frozen in liquid nitrogen and homogenized in Cell Culture Lysis Reagent provided with the Luciferase Assay System (Promega). FL activity was measured according to the manufacturer's instructions using a luminometer (Lumac Biocounter M2500). Clearly, as shown in FIG. 34, luciferase activity could be detected both in liver and brain. As an alternative way to evaluate whether the foreign gene was also expressed in vivo, i.e., in animals, a mouse was inoculated intraperitoneally with $10^6$ $TCID^{50}$ MHV-EFLM. Four days later the mouse was sedated and luciferain was administered subcutaneously. The luciferase expression was evaluated 5 minutes later by real time recording of the emission of light from the body of the sedated mouse using a sensitive screen coupled to a CCD camera. Light emanating from the liver area of the mouse was clearly observed.

Conclusion: A foreign gene can be expressed by coronaviruses in their natural host.

I.3.g. Generation of MHV Expressing Two Foreign Genes from One Genome:

Aim: Establish whether two foreign genes can be expressed from a single genome.

Procedure and Results: pXH2aRLSEFLM was generated by cloning the FL expression cassette into pXH2aRLS digested with EcoRV. After confirmation of the construct by restriction and sequence analysis, recombinant viruses were generated by RNA-RNA recombination between transcription vector run-off transcripts and the fMHV genome as described above. The resulting virus, MHV-RLFL, was genetically confirmed by RT-PCR analysis. Both renilla luciferase activity and firefly luciferase activity could be detected in individual plaques. After generation of a high titer stock, confluent monolayer cultures of LR7 cells were infected at an m.o.i. of 8 and the production of luciferase activity in the cells was monitored over time. RL expression in cells was measured by using the Renilla Assay System (Promega) according to the manufacturer's instructions. Similarly, FL expression was measured by using the Luciferase Assay System (Promega) according to the manufacturer's instructions at 8 hours post-infection. RL and FL activity was measured in relative light units (RLU) using a luminometer (Lumac Biocounter M2500). The results show that MHV-RLFL replicated to the same extent as MHV-2aRLS and MHVEFLM (FIG. 46A). MHV-RLFL expressed both renilla luciferase and firefly luciferase, MHV-2aRLS expressed renilla luciferase only, while MHV-EFLM expressed firefly luciferase only (FIG. 46B).

Conclusion: Two foreign genes can be expressed from a single coronavirus genome:

I.3.h. Generation of MHV Expressing a Chimeric Spike-GFP Gene:

Aim: Establish whether recombinant MHV can be generated that expresses and incorporates chimeric spike-GFP proteins.

Procedure and Results: The GFP gene was cloned in frame with the S gene in pMH54. After confirmation of the construct by restriction and sequence analysis, recombinant viruses were generated by RNA-RNA recombination between transcription vector run-off transcripts and the fMHV genome as described above. The resulting virus, MHV-SGFP, was genetically confirmed by RT-PCR analysis. Plaques were microscopically analyzed and showed expressing of GFP as evidenced by the green fluorescence. Immunoprecipitation analysis indicated that hybrid proteins were generated that could be precipitated with specific antibodies to MHV-S and GFP.

Conclusion: MHV can be generated that expresses a chimeric S-GFP gene in stead of a wild-type S gene. This mutant virus is viable and could be propagated in cell culture indicating that these hybrid proteins are incorporated into the viral particle.

I.4. Inhibition of Infection and of Cell Fusion by Spike Protein Derived Peptide:

General aim: inhibit coronaviral infection and the spread of an ongoing infection by interfering with membrane fusion using peptides.

Specific aim: produce a peptide constituting a sequence derived from the membrane-proximal heptad repeat region (HR2) of the MHV-A59 S protein and demonstrate its inhibitory effect on MHV-A59 entry into LR7 cells and on cell-cell fusion in an infected culture of these cells.

Procedures: a. Plasmid Constructions:

A PCR fragment from a template plasmid pTUMS (13) containing the MHV-A59 spike gene was obtained, corresponding to amino acid residues 1216-1254 (HR2) of the S protein (FIG. 20). The forward primer used was: 5'-GCG-GATCCATCGAAGGTCGTGATTTATCTCTCGATTTC-3' (SEQ ID NO:25). This primer introduced an upstream BamHI site and a sequence encoding a factor Xa cleavage site immediately downstream of the BamHI site into the amplified fragment. The reverse primer (5'-CGAATTCATTCCT-TGAGGTTGATGTAG-3') (SEQ ID NO:26) contained a downstream EcoRI site as well as a stop codon preceding the EcoRI site. The PCR fragment was cloned into the BamHI-EcoRI site of the pGEX-2T bacterial expression vector.

b. Bacterial Protein Expression and Purification:

Freshly transformed BL21 cells (NOVAGEN) were grown in 2YT medium to log phase ($OD_{600}$ of 1.0) and subsequently expression was induced by adding IPTG (GibcoBRL) to a final concentration of 0.4 mM. Two hours after the start of induction the cells were pelleted, resuspended in 1/25 of culture volume 10 mM Tris pH (8.0), 10 mM EDTA, 1 mM PMSF and sonicated on ice (5 times for 2 min with 1-min intervals). Cell lysates were centrifuged at 20,000×g for 60 minutes at 4° C. Then, 2 ml glutathione-sepharose 4B (50% v/v in PBS) was added per 50 ml of supernatant and the suspension was incubated overnight (O/N) at 4° C. under rotation. Beads were washed three times with 50 ml PBS and resuspended in a final volume of 1 ml PBS. Peptides were cleaved from the GST moiety on the beads using 20 U of thrombin by incubation for 4 hours at room temperature (RT).

Peptides in the supernatant were HPLC purified on a Phenyl column with a linear gradient of acetonitrile containing 0.1% trifluoroacetic acid. Peptide containing fractions were vacuum-dried O/N and dissolved in water. Peptide concentration was determined by measuring the absorbance at $A_{280}$ nm or by BCA protein analysis (Micro BCA™ Assay Kit, PIERCE).

c. Virus-Cell Entry and Cell-Cell Fusion Inhibition Assays:

The potency of the HR2 peptide in inhibiting viral infection was determined using the recombinant MHV-EFLM expressing the firefly luciferase. Confluent monolayers of LR7 cells in 96-well plates were inoculated at 37° C. in DMEM at a multiplicity of infection of 5 for 1 hour in the presence of varying concentrations of peptide ranging from 0.4-50 µM. After 1 hour, cells were washed with DMEM and medium was replaced by peptide-free DMEM. At 5 hours post-infection cells were lysed for 15 minutes at RT in 50 µl Lysis buffer, according to the manufacturer's protocol (Luciferase Assay System, Promega). Upon mixing of 10 µl cell lysate with 40 µl substrate, luciferase activity was measured immediately using a Wallace Betaluminometer. The 50% effective inhibitory concentration ($EC_{50}$ value) was calculated by fitting the inhibition data to an equilibrium binding equation: % luciferase activity=$100/(1+(C/EC_{50}))$. The ability of the peptide HR2 to inhibit spike mediated cell-cell fusion was determined using a plaque assay. Monolayers of LR7 cells in 6-well plates were inoculated with 50 PFU of MHV-A59 in DMEM at 37° C. After one hour, the cells were washed with DMEM and an agar overlay was added containing the HR2 peptide at 50, 10, 2, 0.4 and 0.08 µM concentrations. Plaques were counted at 48 hours post-infection, after staining and fixing with 0.9% formaldehyde/0.75% crystal violet.

Results: The potency of the HR2 peptide to inhibit virus entry was tested using a virus expressing a luciferase reporter gene as this allows extremely sensitive detection of infection. Inoculations of cells with the virus were carried out in the presence of different concentrations of HR2 peptide. After 1 hour of inoculation, cells were washed and incubated further in culture medium in the absence of peptide. At 4 hours post-infection, before syncytium formation normally takes place, cells were lysed and tested for luciferase activity (FIG. 11). In this figure the normalized luciferase activity, representing the success of infection, was plotted against the peptide concentration present during inoculation. The HR2 peptide blocked viral entry very efficiently, infection being inhibited virtually completely at the concentration of 50 µM. The effective concentration ($EC_{50}$) at which 50% of viral infection was inhibited was 0.15 µM. The ability of the HR2 peptide to inhibit cell-cell fusion mediated by the spike protein was examined by using a plaque assay. After inoculation of (parallel cultures of) cells in the absence of peptide, an overlay was applied containing different concentrations of HR2 peptide. The formation of plaques appeared to be completely abolished in the presence of HR2 peptide concentrations of up to 0.4 µM (FIG. 12). At 0.08 µM of the HR2 peptide only tiny plaques could be observed.

The specificity of the inhibition was demonstrated in all these assays by testing in parallel the effect of other peptides (FIG. 20) prepared identically and used at the same concentrations, including, for instance, the peptide corresponding to amino acids 1003-1048 of the MHV-A59 S protein (shown as "control peptide" in FIG. 11). Only the HR2 peptide was effective.

Conclusion: The HR2 peptide is a potent inhibitor both of virus entry into cells and of MHV-A59 spike mediated cell-cell fusion.

II. Feline Infectious Peritonitis Virus (FIPV), Strain 79-1146:

II.1. Generation of mFIPV, a Feline Coronavirus Growing on Murine Cells:

General aim: To set up a targeted RNA recombination system for feline coronavirus FIPV 79-1146 similar to the one described above for the genetic manipulation of the murine coronavirus MHV-A59.

Specific aim: Generate mFIPV, an FIPV derivative in which the spike protein ectodomain has been replaced genetically by that of the MHV-A59 S protein, thereby shifting the tropism of the chimeric virus to murine instead of feline cells.

I.1.a. Construction of a Synthetic RNA Transcription Vector:

Aim: Prepare a plasmid construct from which synthetic donor RNA can be transcribed for targeted RNA recombination and which consists of sequences derived from the 5' end of the FIPV genome fused to sequences derived from the 3' part of the viral genome, i.e., all sequences downstream of (and including) the 3'-terminal end of the ORF1B. Also: prepare a derivative of this plasmid in which the sequence encoding the spike ectodomain has been replaced by that encoding the corresponding domain of the MHV-A59 spike protein.

Procedure and Results: Using standard DNA cloning techniques the vector pBRDI1 was constructed which contains a cDNA copy of the 5'-most 702 bases ligated to the 3'-most 9.262 bases of the FIPV 79-1146 genome (FIG. 13A). The ligation was done in such a way that the ORF1A (pol 1A) gene fragment was fused in frame at its 3'-end to the 5'-end of the ORF 1B (pol 1B) gene fragment (FIG. 14B). Furthermore, at this point a unique SacI restriction site was introduced (FIG. 14B). The feline coronavirus sequence was placed under the control of a bacteriophage T7 polymerase promoter sequence followed by a triple G (FIG. 14A) to drive efficient in vitro RNA transcription using the T7 polymerase. At the 3'-end, the sequence was terminated by a polyA tail of 15 A's followed by a unique NotI restriction site (FIG. 14C) to facilitate run-off transcription. The T7 promoter sequence is preceded by a unique XhoI restriction site (FIG. 14A) such that the feline coronavirus cDNA could be cloned as a XhoI-NotI restriction fragment of 10.015 bp into the backbone vector pBRXN (11) resulting in pBRDI1 (FIG. 13A).

Plasmid pBRDI1 was subsequently used to prepare pBRDI2 in which the FIPV S gene was replaced by a chimeric spike gene (mS) composed of a part encoding the ectodomain of the MHV spike protein and a part encoding the transmembrane and endodomain of the FIPV spike protein. To introduce this hybrid gene into pBRDI1, first the 3' end of the feline pol1B gene was fused to the 5' end of the murine spike gene (see FIG. 14D for sequence at junctions). This fusion product was cloned into pTMFS (12) as a SacI-StuI fragment, resulting in pTMFS1 (FIG. 13B). The hybrid gene was then isolated from pTMFS1 as a SacI-AflII fragment and used to replace the FIPV spike gene from pBRDI1 resulting in pBRDI2 (FIG. 13B). The sequences of pBRDI1 and pBRDI2 are shown in addendum 1 and 2, respectively.

II.1.b. Generation of mFIPV by RNA Recombination:

Aim: Generate mFIPV, an FIPV derivative targeted to murine cells.

Procedure and Results: Capped, run-off donor RNA transcripts were synthesized from NotI-linearized pBRDI2 using a T7 RNA polymerase kit (Ambion) according to the instructions of the manufacturer. The transcripts were introduced into feline FCWF cells (80 cm² culture flask) that had been infected before with FIPV 79-1146 (m.o.i. of 1), by electroporation (Gene pulser electroporation apparatus, Biorad, 2 consecutive pulses; 0.3 kV/960 microF). The electroporated cells were cocultured in a 25 cm² flask with murine LR7 cells (50% confluency) to allow recombination of the synthetic and genomic RNA (FIG. 15). After 24 hours of incubation at 37° C., massive syncytia could be observed of both murine LR7 cells and feline FCWF cells. Candidate mFIPV recombinants were selected by taking off the culture supernatant and passaging the virus by three consecutive end-point dilutions on LR7 cells. The resulting virus was unable to infect and cause cytopathic effect on FCWF cells.

Conclusion: A virus with the intended murine cell tropism was obtained.

II.1.c. mFIPV Protein Analysis:

Aim: Confirm the identity of mFIPV at the level of viral protein synthesis.

Procedure and Results: Murine LR7 cells were infected with mFIPV and the proteins were labeled with $^{35}$S-labeled amino acids for 2 hours starting at 5 hours post-infection As controls, we infected LR7 and FCWF cells with MHV and FIPV, respectively, and labeled them similarly from 5-7 hours post-infection. After the labeling, cell lysates were prepared and immunoprecipitations were carried out in the presence of detergent as described (12). The following antibodies were used (for references, see 12): G73 ($\alpha$FIPV), an ascitis fluid obtained from an FIPV-infected cat (provided by H. Vennema); K134 ($\alpha$MHV), a rabbit serum raised against purified MHV-A59; WA3.10 ($\alpha S_m$), a Mab against an epitope present in the MHV-A59 S ectodomain; 23F4.5 ($\alpha S_f$), a Mab against an epitope in the FIPV S ectodomain. The immunoprecipitated proteins were taken up in electrophoresis sample buffer and heated for 2 minutes at 95° C. except for one protein sample (lane 4 in FIG. 16) which was kept at room temperature to prevent aggregation of the MHV M protein. The proteins were analyzed by electrophoresis in SDS-12.5% polyacrylamide gel. The electrophoretic patterns are shown in FIG. 16. As expected, the anti-FIPV antibodies precipitated the FIPV proteins S, M and N from the lysate of FIPV-infected cells (lane 10), but none of the MHV proteins from lysate of MHV-infected cells (lane 1). The 23F4.5 Mab precipitated the feline S of FIPV (lane 11) but not the murine S of MHV (lane 2), as expected. Also, the anti-MHV serum precipitated the MHV proteins S, N and M (lane 3 and 4) but not the FIPV proteins (lane 12), and the WA3.10 Mab precipitated the MHV S protein (lane 5) but not the FIPV S protein (lane 13). When looking at the proteins precipitated from the mFIPV-infected cell lysates, it is clear that the anti-FIPV serum G73 precipitated the M and N proteins, but not the S protein (lane 6). S protein was also not precipitated by the 23F4.5 Mab (lane 7). The mFIPV S protein was, however, precipitated by the anti-MHV serum (lane 8) as well as by the Mab WA3.10 (lane 9).

Conclusion: Cells infected by mFIPV express the predicted viral proteins, particularly the hybrid S protein with the MHV-derived ectodomain.

II.1.d. mFIPV Growth Characteristics:

Aim: Compare titers obtained for mFIPV with those for FIPV and MHV-A59.

Procedure and Results: Infection and titration experiments revealed that the recombinant virus mFIPV was no longer able to infect feline FCWF cells but did grow efficiently in murine LR7 cells showing similar growth characteristics as MHV-A59. This is demonstrated, for instance, by a comparison of their one-step growth curves in these cells shown in FIG. 17. In this experiment, cells were infected with mFIPV and MHV-A59 (m.o.i. of 5 each) after which samples from the culture fluid were taken at various time points and titrated on LR7 cells by end-point dilution. Also, mFIPV induced extensive syncytia and cytopathic effects upon infection of these cells. Stocks of the recombinant mFIPV grown in LR7 cells reached titers of the same order of magnitude as FIPV did in FCWF cells ($5.10^7$ PFU/ml). This was, however, an order of magnitude lower than was observed for MHV-A59 in LR7 cells.

Conclusion: The replacement of the spike protein ectodomain has resulted in a recombinant mFIPV that replicates well in its "new" host cells and has apparently not lost much of its biological fitness.

II.2. Generation of Live Attenuated FIPV Vaccine by Gene Deletions:

General aim: Delete gene sequences from the FIPV genome that are nonessential for viral replication in vitro to obtain deletion viruses that are attenuated in feline animals and are therefore viral (vector) vaccine candidates.

II.2.a. Construction of Synthetic RNA Transcription Vectors:

Aim: Construct the plasmids for the synthesis of donor RNA transcripts lacking the genes 3ABC and/or 7AB for targeted recombination with mFIPV RNA (FIG. 18, top part).

Procedure and Results: Deletions of genes 3ABC and 7AB were introduced into the plasmid pBRDI1 using SOE-PCR. For the primers used, see Table 2 and FIG. 18, left side.

To delete the 3ABC cluster, combinations of primers 1 and 4 and of 2 and 3 were used to generate fragments of 375 bp (A) and 1012 bp (B), respectively (FIG. 18, left side). Fragments A and B were fused using the overlap between both fragments through primers 3 and 4, and amplified using primers 1 and 2 resulting in a 1366 bp fragment (C). Fragment C was digested with AflII and SnaBI and cloned into AflII and SnaBI-digested pBRDI1, resulting in pBRDI1Δ3ABC (FIG. 18).

To delete the 7AB genes, combinations of primers 5 and 8 and of primers 6 and 7 were used to generate fragments of 1215 bp (D) and of 324 bp (E), respectively (FIG. 18). Fragments D and E were fused using the overlap between both fragments through primers 7 and 8, and amplified using primers 5 and 6 resulting in a 1524 bp fragment (F). Fragment F was digested with MluI and NotI and cloned into MluI and NotI-digested pBRDI1, resulting in pBRDI1Δ7AB (FIG. 18). The correctness of the sequences of fragments C and F was confirmed by DNA sequencing.

To construct pBRDI1Δ3ABC+Δ7AB, the 1524 bp MluI/NotI fragment of pBRDI1Δ7AB was introduced into MluI/NotI-digested pBRDI1Δ3ABC (FIG. 18).

Conclusion: The pBRDI1-derived donor RNA constructs lacking the gene clusters 3ABC and/or 7AB were obtained.

II.2.b. Generations of Recombinant FIPVs Lacking Genes:

Aim: Generate the recombinant FIPVs that lack the sequences for the 3ABC genes, for the 7AB genes, and for both these gene clusters.

Procedure and Results: Capped, run-off donor transcripts were synthesized from NotI-linearized pBRDI1, pBRDI1Δ3ABC, pBRDI1Δ7AB and pBRDI1Δ3ABC+Δ7AB, respectively, using a T7 RNA polymerase kit (Ambion) as specified by the manufacturer. The donor transcripts were introduced into murine LR7 cells (80 cm² flask), that had been infected before with mFIPV (m.o.i. of 0.4), by electroporation (Gene pulser electroporation apparatus, Biorad, 2 consecutive pulses; 0.85 kV/50 microF). The electroporated cells were cocultured in a 25 cm² culture flask with feline FCWF cells (50% confluency). After 24 hours incubation at 37° C. massive syncytia could be detected in both the murine LR7 cells and the feline FCWF cells. Candidate deletion viruses released into the mixed cell culture supernatant were purified by two rounds of plaque purification on FCWF cells.

Conclusion: Viruses that had acquired the ability to grow in feline FCWF cells had been obtained from the recombination experiment with mFIPV.

II.2.c. Genetic Analysis of Recombinant FIPVs Lacking Genes:

Aim: Confirm the genetic make-up of the putative deletion viruses.

Procedure and Results: To evaluate whether the intended deletions indeed occurred in the various FIPV deletion mutants, RT-PCR on the genomic viral RNA's was performed focusing on the 3ABC and the 7AB region. The primers used and DNA sizes expected are indicated in Table 2 and FIG. 18 (right side). The results of the RT-PCR analyses are shown in FIG. 19. FIG. 19A reveals that the recombinant wild-type virus (r-wtFIPV) and FIPVΔ7AB are each carrying the 3ABC region whereas this region is lacking in the viruses FIPVΔ3ABC and FIPVΔ3ABC+Δ7AB, as judged by the sizes of the amplified fragments. FIG. 19B demonstrates that r-wtFIPV and FIPVΔ3ABC are still carrying the 7AB region whereas the viruses FIPVΔ7AB and FIPVΔ3ABC+Δ7AB are lacking this region. The 397 bp and 646 bp fragments, indicative of a 3ABC and 7AB deletion, respectively, were cloned and sequenced which confirmed the expected DNA sequences.

Conclusion: The deletion viruses had precisely the intended genomic deletions.

II.2.d. Growth Characteristics of FIPVs Lacking Genes

Aim: Check cell tropism of the deletion viruses and evaluate their in vitro growth.

Results: All 4 recombinant viruses were inoculated onto mouse LR7 cells but failed to produce any cytopathic effects. They did, however, grow efficiently in feline FCWF cells, as expected. The viruses r-wtFIPV, FIPVΔ3ABC and FIPVΔ7AB reached titers that were similar to those obtained with the parent FIPV strain 79-1146 on these cells. The titers were all in the order of $5.10^7$ PFU/ml (FIG. 40). However, the double mutant FIPVΔ3ABC+Δ7AB grew less efficient; titers obtained with this virus were generally 1 to 2 log units lower (FIG. 40).

Conclusion: The sequences comprising the gene clusters 3ABC and 7AB are not essential for the viability of FIPV. Apparently, neither the nucleotide sequences nor the proteins encoded by the genes are essential for the replication of the virus.

II.2.e. Virulence of Recombinant Viruses in Cats:

Aim: Establishing whether the genetic deletions affect virulence.

Procedure and Results: The recombinant deletion viruses were characterized in their natural host, the cat. To this purpose, 24 SPF cats (5 months old) were placed into 5 groups and inoculated oranasally (100 pfu) with FIPV strain 79-1146 (n=4), r-wtFIPV (n=5), FIPVΔ3ABC (n=5), FIPVΔ7AB (n=5) and FIPVΔ3ABC+Δ7AB (n=), respectively, and followed for (at least) 3 months. Clinical disease signs were scored as shown in Table 5. Inoculation of the cats with the deletion variants did not induce clinical signs of disease. Rather, all cats remained totally healthy throughout the experiment (Table 6 and FIG. 35). In contrast, infection with the wild type controls FIPV 79-1146 and r-wtFIPV induced a rapid onset of clinical disease characterized by depression, anorexia, jaundice, weight loss and leukopenia (Table 6). Three out of four and five out of five cats inoculated with FIPV 79-1146 and r-wtFIPV, respectively, had to be euthanized due to advanced symptoms of FIP between day 14 and day 42 after infection (FIG. 35).

Conclusions: 1) FIPV 79-1146 and its wild type recombinant equivalent r-wtFIPV are equally virulent; and 2) Viruses with deletions of the sequences specifying the genes 3abc or 7ab or of the combination of some or all these genes exhibit a significantly attenuated phenotype in cats.

II.2.f. Immune Response Induced by Recombinant Viruses:

Aim: Determining the FIPV-neutralizing activity in cat sera.

Procedure and Results: FIPV-specific antibody responses of the cats inoculated with the deletion viruses were characterized. To this purpose, blood samples were obtained at days 0, 21 and 90 post-infection, and heat-inactivated sera were prepared and incubated with FIPV 79-1146 (10.000 PFU) after which the FIPV-neutralizing activity was determined using FCWF cells in a 96-well microplate assay. Titers were expressed as the reciprocal of the lowest dilution that no longer inhibited viral cytopathic effects. As expected, at day 0 none of the cat sera showed a significant FIPV-neutralizing activity. At day 21, all cats had sero-converted and showed high titers of neutralizing antibodies. The titers observed in cats inoculated with FIPV 79-1146, r-wtFIPV, FIPVΔ3ABC and FIPVΔ7AB were comparable whereas the titers observed in FIPVΔ3ABC+Δ7AB infected cats were approximately 50 fold lower (FIG. 36). Overall, the titers remained high for at least 90 days (end of experiment).

Conclusion: Despite the absence of clinical disease signs, high titers of neutralizing antibodies are observed in cats that had been inoculated with FIPV deletion variants. This strongly suggests that the deletion viruses are viable and replicate in the cat leading to a strong immune response in the form of an antibody response.

II.2.g. FIPV Deletion Viruses Serve as Attenuated, Live Vaccines:

Aim: To study whether previous inoculation with the attenuated deletion variants protects the cats against a FIPV 79-1146 challenge.

Procedure and Results: The cats previously inoculated with the attenuated deletion variants were challenged oranasally with FIPV 79-1146 (100 pfu) at day 90. As a control group, 4 untreated cats of similar age were challenged identically. The control group showed a rapid onset of clinical disease characterized by depression, anorexia, jaundice, weight loss and leukopenia (day 7). A similar rapid onset of symptoms was observed with 3 out 5 cats previously inoculated with FIPVΔ3ABC+Δ7AB, whereas all cats previously infected with FIPVΔ3ABC or FIPVΔ7AB remained generally healthy and without typical FIP symptoms throughout the experiment (Table 7), although 2 out 5 cats previously inoculated with FIPVΔ3ABC showed temporary weight loss.

Due to advanced symptoms of FIP, one cat out of the control group had to be euthanized at day 32, whereas the other cats in the control group recovered from their initial FIP symptoms. A lethality score of 25% is lower than observed in the previous experiments. This is supposedly due to the advanced age of the cats which is known to lead to reduced susceptibility for FIPV. The three FIPVΔ3ABC+Δ7AB vaccinated cats with initial symptoms remained ill and were euthanized between days 11 and 56 (FIG. 37). Apparently, the combined deletion of the two gene clusters 3ABC and 7AB which we found to reduce the fitness of FIPVΔ3ABC+ Δ7AB—as judged by its decreased in vitro growth—also affects the replication rate of the virus in the cats, as testified by the lower levels of neutralizing antibodies induced. Thus, the virus is over-attenuated and only capable of partially protecting against a FIPV challenge. Full protection would require a higher or repeated dose.

Conclusion: Prior vaccination with FIPVΔ3ABC or FIPVΔ7AB protects cats against disease caused by a FIPV challenge.

II.3. Insertion and Expression of Foreign Genes:

Aim: Establish whether foreign genes can be inserted at different positions in the viral genome, either as an additional gene or replacing deleted nonessential genes; and establish whether these genes are expressed and whether they are stably maintained during in vitro passage of the virus.

II.3.a. Construction of Recombinant Viruses Carrying Reporter Genes:

Aim: Generate FIPV 79-1146 viruses with foreign gene insertions.

Procedure: A virus was constructed containing a foreign reporter gene in its genome at the position of the 3abc genes. The reporter gene, renilla luciferase (RL), was placed under the transcriptional control of the IGS proceeding gene 3a. To delete the 3abc cluster and introduce the RL gene into the plasmid pBRDI1, combinations of primers 1244 (5'-GCCAT-TCTCATTGATAAC-3) (SEQ ID NO:27) and 1514 (5'-CT-GAGTCTAGAGTA GCTAGCTAATGACTAATAAGTTTAG-3') (SEQ ID NO:28) and of 1245 (5'-GCTTCTGTTGAGTAATCACC-3) (SEQ ID NO:29) and 1513 (5'-GCTAGCTACTCTAGACTCAGGCGGTTCTAAAC-3) (SEQ ID NO:30) were used to generate fragments of 336 bp (A) and 1068 bp (B) via PCR, respectively. In primer 1513 and 1514, the underlined and bold sequences represent a NheI and XbaI restriction site, respectively. Fragments A and B were fused using the overlap between both fragments through primers 1514 and 1513 and amplified using primers 1244 and 1245, using SOE-PCR, resulting in a 1384 bp fragment (C). Fragment C was cloned into the pGEM-T Easy vector (Promega), resulting in pGEM-C. The RL gene derived from pRL-null (Promega) was introduced as a NheI/XbaI fragment into NheI and XbaI digested pGEM-C, resulting in pGEM-C+luc. Fragment C+luc was introduced as a AflII/SnaBI fragment into AflII and SnaBI-digested pBRDI1, resulting in pBRDI1Δ3ABC+luc.

After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis.

Conclusion: The foreign reporter gene renilla luciferase can be placed into the genome of the type I coronavirus FIPV. The intended recombinant viruses are viable.

II.3.b. One-Step Growth of Viruses:

Aim: Compare the growth characteristics of the viruses with wild-type virus.

Procedure and Results: After two rounds of plaque purification, virus stocks of 2 independently obtained recombinants under II.3.a were prepared, titrated and used for high m.o.i (m.o.i. of 8) infection of FCWF cells after which the viral infectivities in the culture media were monitored. The results are represented by the growth curves shown in FIG. 38. Both independently obtained recombinants grew to a 1 to 2 log lower titer as compared to that of recombinant wild-type virus.

Conclusion: The recombinant viruses with inserted expression cassette grew normally in vitro but their yields were affected.

II.3.c. Expression of Renilla Luciferase:

Aim: Establish whether the inserted expression cassette was functional.

Procedure and Results: Confluent monolayer cultures of FCWF cells were infected at an m.o.i of 8 and the production of luciferase activity in the cells was monitored over time. RL expression in cells was measured by using the Dual-Luciferase Reporter Assay System (Promega) according to the manufacturer's instructions. RL was measured in relative light units (RLU) using a luminometer (Lumac Biocounter M2500 or Turner Designs Model TD-20/20).

The results are shown graphically in FIG. 39. In contrast to the recombinant wild-type virus, the two recombinant luciferase gene containing viruses expressed high levels of luciferase activity, indicating that the renilla luciferase gene is functional. Expression started as early as 2 hours post-infection. The highest expression level was reached at 9 hours post-infection.

Conclusion: Foreign genes can be expressed by coronaviruses by using the genetic space created by deletion of nonessential genes.

II.4 Generation of Multivalent FIPV-Based Vaccines:

Aim: Development of multivalent vaccines based on a live attenuated FIPV strain as a vector.

Approach: Genes (or gene fragments) from other feline and canine pathogens encoding antigens known to induce protective immunity against these pathogens were selected. Expression cassettes of these genes were introduced into the FIPV genome in combination with attenuating deletions of nonessential genes. The expression cassettes contain the FIPV TRS in front of (parts of) the gene to be expressed.

II.4.a. Construction of a Multivalent Feline Leukemia Virus (FeLV) Vaccine Based on FIPV Vector:

Aim: Development of FeLV vaccine based on a live attenuated FIPV strain as a vector.

Procedure: (Parts of) the protection related FeLV genes gag and env were placed into expression cassettes and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of the FeLV gag and env genes was confirmed by immunoprecipitation analysis.

Conclusion: (Parts of) the protection related FeLV genes gag and env can be introduced into and expressed by a live attenuated FIPV strain. These recombinants can therefore function as a multivalent vaccine against a Feline leukemia virus and FIPV infection.

II.4.b. Construction of a Multivalent Feline Immunodeficiency Virus (FIV) Vaccine Based on an FJPV Vector:

Aim: Development of FIV vaccine based on a live attenuated FIPV strain as a vector.

Procedure: (Parts of) the protection related FIV genes gag and env were placed into expression cassettes and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of the FIV gag and env genes was confirmed by immunoprecipitation analysis.

Conclusion: (Parts of) the protection related FIV genes gag and env can be introduced into and expressed by a live attenuated FIPV strain. These recombinant viruses can therefore function as a multivalent vaccine against a Feline immunodeficiency virus and FIPV infection.

II.4.c. Construction of a Multivalent Feline Calicivirus (FCV) Vaccine Based on an FIPV Vector:

Aim: Development of FCV vaccine based on a live attenuated FIPV strain as a vector.

Procedure: (Parts of) the protection related FCV capsid gene was placed into an expression cassette and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of the FCV capsid gene was confirmed by immunoprecipitation analysis.

Conclusion: (Parts of) the protection related FCV capsid gene can be introduced into and expressed by a live attenuated FIPV strain. These recombinant viruses can therefore function as a multivalent vaccine against a Feline calicivirus and FIPV infection.

II.4.d. Construction of a Multivalent Feline Panleucopenia Virus (FPV) Vaccine Based on an FIPV Vector:

Aim: Development of FPV vaccine based on a live attenuated FIPV strain as a vector.

Procedure: (Parts of) the protection related R3 gene, encoding the VP1 and VIP2 capsid proteins was placed into an expression cassette and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of (parts of) the R3 gene was confirmed by immunoprecipitation analysis.

Conclusion: (Parts of) the protection related R3 gene can be introduced into and expressed by a live attenuated FIPV strain. These recombinant viruses can therefore function as a multivalent vaccine against a Feline panleucopenia virus and FIPV infection.

II.4.e. Construction of a Multivalent Feline Herpes Virus (FHV) Vaccine Based on an FIPV Vector:

Aim: Development of FHV vaccine based on a live attenuated FIPV strain as a vector.

Procedure: (Parts of) the protection related gB, gC, gD, gE, gH, gI, gK, gL, gM, gM, ICP0, ICP1 and ICP4 feline herpes virus genes were placed into an expression cassette and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of the inserted FHP genes was confirmed by immunoprecipitation analysis.

Conclusion: (Parts of) the protection related gB, gC, gD, gE, gH, gI, gK, gL, gM, ICP0, ICP1 and ICP4 feline herpes virus genes can be introduced and expressed in a live attenuated FIPV strain. These recombinant viruses can therefore function as a multivalent vaccine against Feline herpes virus and FIPV.

II.4.f. Construction of a Multivalent FIPV Serotype I and II Vaccine Based on an FIPV Serotype II Vector:

Aim: Development of a vaccine protecting both against serotype I and against II feline coronaviruses, based on a live attenuated FIPV serotype II strain as a vector.

Procedure: (Parts of) the protection related spike gene of a serotype I feline coronavirus, of which the region encoding the signal sequence was deleted, was placed into an expression cassette and subsequently introduced into pBRDI1Δ3ABC and pBRDI1Δ7AB, respectively. For example: in one case, a spike gene construct was used from which the region encoding the signal sequence had been deleted; in another case a truncated spike gene was used, from which the region encoding the transmembrane domain+endodomain had been deleted. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of the inserted serotype I spike gene construct was confirmed by immunoprecipitation analysis.

Conclusion: (Parts of) the protection related spike gene of feline coronavirus serotype I can be introduced and expressed in a live attenuated FIPV serotype II strain and can therefore function as a multivalent vaccine against both serotype I and II feline coronaviruses.

II.5. Generation of Recombinant Viruses with Rearranged Gene Order:

Aim: Development of a FIPV vaccine in which deletion of nonessential genes is combined with a rearranged gene order by moving the N gene upstream of the S gene in the FIPV genome.

Procedure and Results: Capped, run-off donor transcripts were synthesized from NotI-linearized pBRDI1Δ3ABC, pBRDI1Δ7AB and pBRDI1Δ3ABC+Δ7AB vectors in which the N gene, together with its TRS, was inserted at a position upstream of the S. The donor transcripts were introduced into murine LR7 cells (80 cm$^2$ flask), that had been infected before with mFIPV (m.o.i. of 0.4), by electroporation (Gene pulser electroporation apparatus, Biorad, 2 consecutive pulses; 0.85 kV/50 microF). The electroporated cells were co-cultured in a 25 cm$^2$ culture flask with feline FCWF cells (50% confluency). After 24 hours incubation at 37° C. massive syncytia could be detected in the cell cultures. Deletion mutant viruses with rearranged genomes released into the mixed cell culture supernatant were purified by two rounds of plaque purification on FCWF cells.

Conclusion: Deletion mutant FIPVs with rearranged gene order could be generated. These viruses can function as live attenuated FIPV vaccines. By virtue of their rearranged gene order these viruses represent safer vaccines because of their reduced ability to generate viable progeny by recombination with viruses circulating in the field.

II.6 Generation of FIPV Based Vaccines Against Canine Pathogens:

General aim: Development of vaccines based on a live attenuated FIPV serotype II strain as a vector against canine pathogens.

Approach: Since type II feline coronaviruses express canine coronavirus-like spike proteins (2a), such feline coronavirus vectors can be used as vaccines in canines.

Therefore, the live attenuated FIPV vaccine that we developed can also be used for vaccination of canines against canine coronavirus (CCV). Furthermore, multivalent vaccines can be generated by introducing expression cassettes of protection related genes of other canine pathogens into the FIPV genome in combination with attenuating deletions of nonessential genes and with genome rearrangements. The expression cassettes contain the FIPV TRS in front of (parts of) the gene to be expressed.

II.6.a. Generation of FIPV Based Vaccine Against Canine Distemper:

Aim: Development of canine distemper vaccine based on a live attenuated FIPV strain as a vector.

Procedure: (Parts of) the protection related H and F genes were placed into an expression cassette and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of (parts of) the H and F genes was confirmed by immunoprecipitation analysis.

Conclusion: (Parts of) the protection related H and F genes of canine distemper virus can be introduced into and expressed by a live attenuated FIPV strain. These recombinant viruses can therefore function as a vaccine against canine distemper virus and CCV infection.

II.6.b. Generation of FIPV Based Vaccine Against Canine Parvo Disease:

Aim: Development of canine parvovirus vaccine based on a live attenuated FIPV strain as a vector.

Procedure: (Parts of) the protection related R3 gene, encoding the VP1 and VIP2 capsid proteins were placed into an expression cassette and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of (parts of) the R3 gene was confirmed by immunoprecipitation analysis.

Conclusion: (Parts of) the protection related R3 gene of canine parvovirus can be introduced into and expressed by a live attenuated FIPV strain. These recombinant viruses can therefore function as a vaccine against canine parvovirus disease and CCV infection.

II.6.c. Generation of FIPV Based Vaccine Against Infectious Canine Hepatitis:

Aim: Development of canine adenovirus serotype 1 vaccine based on a live attenuated FIPV strain as a vector.

Procedure: (Parts of) the protection related structural protein genes of canine adenovirus serotype 1 were placed into an expression cassette and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of (parts of) the protection related structural protein genes of canine adenovirus serotype 1 was confirmed by immunoprecipitation analysis.

Conclusion: (Parts of) the protection related structural protein genes of canine adenovirus serotype 1 can be introduced into and expressed by a live attenuated FIPV strain. These recombinant viruses can therefore function as a vaccine against infectious canine hepatitis and CCV infection.

II.6.d. Generation of FIPV Based Vaccine Against Hemorrhagic Disease of Pups:

Aim: Development of canine herpes virus 1 vaccine based on a live attenuated FIPV strain as a vector.

Procedure: (Parts of) the protection related gB, gC, gD, gE, gH, gI, gK, gL, gM, gM, ICP0, ICP1 and ICP4 canine herpes virus genes were placed into an expression cassette and subsequently introduced into pBRDI1Δ3ABC and pBRDI1Δ7AB, respectively. After confirmation of all constructs by restriction and sequence analysis, recombinant viruses were generated by RNA-RNA recombination between transcription vector run-off transcripts and the mFIPV genome as described above. The resulting viruses were genetically confirmed by RT-PCR analysis. Expression of the inserted genes was confirmed by immunoprecipitation analysis.

Conclusion: (Parts of) the protection related gB, gC, gD, gE, gH, gT, gK, gL, gM, ICP0, ICP1 and ICP4 canine herpes virus genes can be introduced and expressed in a live attenuated FIPV strain. These recombinant viruses can therefore function as a multivalent vaccine against canine herpes virus 1 and CCV.

III. Transmissible Gastro-Enteritis Virus (TGEV):

III.1. Generation of a Live Attenuated Vaccine Against TGEV:

Aim: Development of a live attenuated vaccine against TGEV.

Approach: To this aim recombinant TGEV deletion mutant viruses were generated that lack the nonessential genes 3ab and/or 7.

Procedure: Recombinant viruses were generated as described by Almazan et al. (2000). From pBAC-TGEV$^{FL}$, an infectious TGEV cDNA clone placed behind a CMV promoter in pBeloBAC11, the 3ab and 7 genes were deleted via standard cloning techniques, leaving the surrounding open reading frames and transcription regulatory sequences intact. Epithelial swine testis (ST) cells were transfected with this pBAC-TGEV$^{FL}$ derivative which lacks the 3ab and 7 genes (PBAC-TGEV$^{FL}$). Recombinant TGEV viruses were plaque purified and characterized by RT-PCR for the absence of the 3ab and/or 7 genes. Large amounts of the recombinant TGEV deletion viruses were generated by infecting ST cells.

Conclusion: Recombinant TGEV was generated that lacked the genes 3ab and 7. These viruses can function as a live attenuated vaccine against TGEV.

III.2 Generation of Multivalent TGEV-Based Vaccines:

Aim: Development of multivalent vaccines based on a live attenuated TGEV as a vector.

Approach: Expression cassettes of protection related genes of porcine pathogens were introduced into the TGEV genome in combination with attenuating deletions of nonessential genes and genome rearrangements. The expression cassettes contain the TGEV TRS in front of (parts of) the gene to be expressed.

III.2.a. Construction of a Multivalent Porcine Parvovirus (PPV) Vaccine Based on a TGEV Vector:

Aim: Development of a vaccine based on a live attenuated TGEV strain as a vector. Procedure: (Parts of) the protection related R3 gene, encoding the VP1 and VP2 capsid proteins, was placed into an expression cassette and subsequently introduced into a pBAC-TGEV$^{FL}$ derivative which lacks genes 3ab and 7. After confirmation of all constructs by restriction and sequence analysis, recombinant viruses were generated by transfecting ST cells with this pBAC-TGEV$^{FL}$ deletion derivative which contains (parts of) the protection related R3 gene. The resulting viruses were genetically confirmed by RT-PCR analysis. Expression of the inserted R3 gene was confirmed by immunoprecipitation analysis.

Conclusion: (Parts of) the protection related R3 gene can be introduced into and expressed by a live attenuated TGEV strain. These recombinant viruses can therefore function as a multivalent vaccine against a Porcine Parvovirus and TGEV infection.

III.2.b. Construction of a Multivalent Swine Influenza Virus Vaccine Based on a TGEV Vector:

Aim: Development of a swine influenza virus vaccine based on a live attenuated TGEV strain as a vector.

Procedure: (Parts of) the protection related hemagglutinin (HA) and neuraminidase (NA) genes were placed into an expression cassette and subsequently introduced into a pBAC-TGEV$^{FL}$ derivative which lacks the genes 3ab and 7. After confirmation of all constructs by restriction and sequence analysis, recombinant viruses were generated by transfecting ST cells with this pBAC-TGEV$^{FL}$ deletion derivative which contains (parts of) the protection related hemagglutinin (HA) and neuraminidase (NA) genes. The resulting viruses were genetically confirmed by RT-PCR analysis. Expression of the inserted hemagglutinin (HA) and neuraminidase (NA) genes was confirmed by immunoprecipitation analysis.

Conclusion: (Parts of) the protection related hemagglutinin (HA) and neuraminidase (NA) genes can be introduced into and expressed by a live attenuated TGEV strain. These recombinant viruses can therefore function as a multivalent vaccine against a swine influenza virus and TGEV infection.

III.2.c. Construction of a Multivalent African Swine Fever Virus Vaccine Based on a TGEV Vector:

Aim: Development of an African swine fever virus vaccine based on a live attenuated TGEV strain as a vector.

Procedure: (Parts of) the protection related structural protein encoding genes were placed into an expression cassette and subsequently introduced into a pBAC-TGEV$^{FL}$ derivative which lacks the genes 3ab and 7. After confirmation of all constructs by restriction and sequence analysis, recombinant viruses were generated by transfecting ST cells with this pBAC-TGEV$^{FL}$ deletion derivative which contains (parts of) the protection related structural-protein encoding genes. The resulting viruses were genetically confirmed by RT-PCR analysis. Expression of the structural-protein encoding genes was confirmed by immunoprecipitation analysis.

Conclusion: (Parts of) the protection related structural protein encoding genes can be introduced into and expressed by a live attenuated TGEV strain. These recombinant viruses can therefore function as a multivalent vaccine against an African swine fever virus and TGEV infection.

III.2.d. Construction of a Multivalent Porcine Circovirus Type 2 Vaccine Based on a TGEV Vector:

Aim: Development of a Porcine circovirus type 2 vaccine based on a live attenuated TGEV strain as a vector.

Procedure: (Parts of) the protection related C1, C2, V1 and V2 genes of the Porcine circovirus type 2 were placed into an expression cassette and subsequently introduced into a pBAC-TGEV$^{FL}$ derivative which lacks the genes 3ab and 7. After confirmation of all constructs by restriction and sequence analysis, recombinant viruses were generated by transfecting ST cells with this pBAC-TGEV$^{FL}$ deletion derivative which contains (parts of) the protection related C1, C2, V1 and V2 genes of the Porcine circovirus type 2. The resulting viruses were genetically confirmed by RT-PCR analysis. Expression of the C1, C2, V1 and V2 genes of the Porcine circovirus type 2 was confirmed by immunoprecipitation analysis.

Conclusion: (Parts of) the protection related C1, C2, V1 and V2 genes of the Porcine circovirus type 2 can be introduced into and expressed by a live attenuated TGEV strain. These recombinant viruses can therefore function as a multivalent vaccine against a Porcine circovirus type 2, and TGEV infection.

III.2.e. Construction of a Multivalent Porcine Respiratory and Reproductive Syndrome Virus Vaccine Based on a TGEV Vector:

Aim: Development of a Porcine respiratory and reproductive syndrome virus vaccine based on a live attenuated TGEV strain as a vector.

Procedure: (Parts of) the protection related ORF2 to ORF7 of the Porcine respiratory and reproductive syndrome virus were placed into an expression cassette and subsequently introduced into a pBAC-TGEV$^{FL}$ derivative which lacks the genes 3ab and 7. After confirmation of all constructs by restriction and sequence analysis, recombinant viruses were generated by transfecting ST cells with this pBAC-TGEV$^{FL}$ deletion derivative which contains (parts of) the protection related ORF2 to ORF7 of the Porcine respiratory and reproductive syndrome virus. The resulting viruses were genetically confirmed by RT-PCR analysis. Expression of ORF2 to ORF7 of the Porcine respiratory and reproductive syndrome virus was confirmed by immunoprecipitation analysis.

Conclusion: (Parts of) the protection related ORF2 to ORF7 of the Porcine respiratory and reproductive syndrome virus can be introduced into and expressed by a live attenuated TGEV strain. These recombinant viruses can therefore function as a multivalent vaccine against a Porcine respiratory and reproductive syndrome virus and TGEV infection.

III.2.f. Construction of a Multivalent Foot-and-Mouth Disease Virus Vaccine Based on a TGEV Vector:

Aim: Development of a foot-and-mouth disease virus vaccine based on a live attenuated TGEV strain as a vector.

Procedure: (Parts of) the protection related sequences encoding VP1 to VP4 of the foot-and-mouth disease virus were placed into an expression cassette and subsequently introduced into a pBAC-TGEV$^{FL}$ derivative which lacks the genes 3ab and 7. After confirmation of all constructs by restriction and sequence analysis, recombinant viruses were generated by transfecting ST cells with this pBAC-TGEV$^{FL}$ deletion derivative which contains (parts of) the protection related sequences encoding VP1 to VP4 of the foot-and-mouth disease virus. The resulting viruses were genetically confirmed by RT-PCR analysis. Expression of the sequences encoding VP1 to VP4 of the foot-and-mouth disease virus was confirmed by immunoprecipitation analysis.

Conclusion: (Parts of) the protection related sequences encoding VP1 to VP4 of the foot-and-mouth disease virus can be introduced into and expressed by a live attenuated TGEV strain. These recombinant viruses can therefore function as a multivalent vaccine against a foot-and-mouth disease virus and TGEV infection.

III.3. Generation of Recombinant Viruses with Rearranged Gene Order:

Aim: Development of a TGEV vaccine in which deletion of nonessential genes is combined with a rearranged gene order by moving the N gene upstream of the S gene in the TGEV genome.

Procedure and Results: Recombinant viruses were generated as described by Almazan et al. (2000). From pBAC- TGEV$^{FL}$, an infectious TGEV cDNA clone placed behind a CMV promoter in pBeloBAC11, the 3ab and 7 genes were deleted via standard cloning techniques, leaving the surrounding open reading frames and transcription regulatory sequences intact. In addition the N gene was cloned to a position in the genome upstream of the S gene. Epithelial swine testis (ST) cells were transfected with this pBAC-TGEV$^{FL}$ derivative which lacks the 3ab and 7 genes and has a rearranged genome. Recombinant TGEV viruses were plaque purified and characterized by RT-PCR for the absence of the 3ab and/or 7 genes. Large amounts of the TGEV deletion recombinants were generated by infecting ST cells.

Conclusion: Recombinant TGEV was generated that lacked the genes 3ab and 7, and which has a rearranged gene order. These viruses function as a live attenuated vaccine against TGEV, as well as against other porcine pathogens when genes encoding relevant antigens are appropriately incorporated.

IV. Avian Infectious Bronchitis Virus (IBV):

IV.1. Generation of a Live Attenuated Vaccine Against IBV:

Aim: Development of a live attenuated vaccine against IBV.

Approach: Recombinant IBV deletion mutant viruses were generated that lack the nonessential genes 3a/b and/or 5a/b. In order to acquire vaccine viruses that protect against multiple IBV serotypes, spike gene constructs derived from such different viruses were incorporated.

Procedure: Recombinant viruses were generated as described by Casais et al. (2001). Infectious IBV cDNA clones were assembled in the vaccinia virus genome by using sequential in vitro ligation of cDNA fragments derived from pFRAG1, pFRAG2, and pFRAG3 derived plasmids, followed by direct cloning into the genome of vaccinia virus vNotI/tk as described (1a). Genes 3a/b and 5a/b were removed from pFRAG3, by PCR mutagenesis leaving the surrounding open reading frames and transcription regulatory sequences intact, resulting in pFRAG3Δ. The S gene in pFRAG3Δ could be replaced by S genes derived from different IBV serotypes by using RT-PCR. Recombinant vaccinia viruses were generated by recombination between the fowl pox virus HP1.441 and the vNotI/tk-IBV in vitro ligation mixture. Recombinant viruses were plaque purified and characterized by PCR and Southern blot analysis. Finally, infectious IBV lacking genes 3a/b and/or 5a/b was generated as follows: Chick kidney (CK) cells were infected with recombinant fowl pox virus expressing T7 RNA polymerase. Subsequently, cells were transfected with DNA isolated from the recombinant vaccinia virus containing the IBV cDNA clone lacking genes 3a/b and 5a/b. At 3 days post-infection, the culture medium was collected and used to infect CK cells to generate large amounts of recombinant IBV. The recombinant viruses were genetically confirmed by RT-PCR analysis.

Conclusion: Recombinant IBV was generated that lacked the genes 3a/b and/or 5a/b. These viruses can function as a live attenuated vaccine against IBV. By replacing the S gene, recombinant IBVs could be obtained that function as live attenuated vaccines against different IBV serotypes.

IV.2. Generation of Multivalent IBV-Based Vaccines:

Aim: Development of multivalent vaccine based on a live attenuated IBV strain as a vector.

Approach: Expression cassettes of protection related genes of chicken pathogens were introduced into the IBV genome in combination with attenuating deletion of nonessential genes. The expression cassettes contain the IBV TRS (CTTAA-CAA) (SEQ ID NO:31) in front of (parts of) the gene to be expressed.

IV.2.aI. Construction of a Multivalent Vaccine Based on an IBV Vector that Protects Against More than One IBV Serotype:

Aim: Development of an IBV vaccine based on a live attenuated IBV strain that lacks nonessential genes and protects against more than one serotype.

Procedure: (Parts of) the protection related IBV S gene from a different IBV serotype were placed into expression cassettes, and subsequently introduced into pFRAG3Δ. The largest construct contained a complete extra copy of the S gene except for the sequence encoding the signal peptide; another construct had a carboxy-terminally truncated S gene lacking the code for the transmembrane domain and endodomain. After confirmation of all the constructs by restriction and sequence analysis, recombinant viruses were generated as described above. The recombinant viruses were genetically confirmed by RT-PCR analysis. The proper expression of the heterologous S gene constructs was verified by immunoprecipitation analysis with type-specific antisera using radiolabeled recombinant virus infected cell lysates.

Conclusion: (Parts of) the protection related IBV S gene from a different IBV serotype can be introduced in and expressed from a live attenuated IBV strain. These recombinant viruses can therefore function as multivalent vaccines to protect against infection by more than one IBV serotype.

IV.2.aII. Construction of a Multivalent Vaccine Based on an IBV Vector that Protects Against Newcastle Disease:

Aim: Development of a Newcastle Disease Virus (avian paramyxovirus type I; APMV-1) Vaccine Based on a Live Attenuated IBV Strain that Lacks Nonessential Genes.

Procedure: (Parts of) the protection related APMV-1 genes HN and F were placed in expression cassettes, and subsequently introduced into pFRAG3Δ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related APMV-1 genes HN and F can be introduced in and expressed from a live attenuated IBV strain. The recombinant viruses can therefore function as a multivalent vaccine to protect against APMV-1 and IBV infections.

IV.2.b. Construction of a Multivalent Vaccine Based on an IBV Vector that Protects Against Avian Influenza:

Aim: Development of an Avian Influenza virus vaccine based on a live attenuated IBV strain that lacks nonessential genes.

Procedure: (Parts of) the protection related Avian Influenza genes H and N were placed into expression cassettes, and subsequently introduced into pFRAG3Δ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related Avian Influenza genes H and N can be introduced in and expressed from a live attenuated IBV strain. These recombinant viruses can therefore function as a multivalent vaccine to protect against Avian Influenza and IBV infections.

IV.2.c. Construction of a Multivalent Vaccine Based on an IBV Vector that Protects Against Chicken Anemia Virus (CAV) Disease:

Aim: Development of a CAV vaccine based on a live attenuated IBV strain that lacks nonessential genes.

Procedure: (Parts of) the protection related CAV genes V1, V2, and V3 were placed into expression cassettes, and subsequently introduced into pFRAG3Δ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related CAV genes V1, V2, and V3 can be introduced in and expressed from a live attenuated IBV strain. These recombinant viruses can therefore function as a multivalent vaccine to protect against CAV and IBV infections.

IV.2.d. Construction of a Multivalent Vaccine Based on an IBV Vector that Protects Against Avian Reovirus Disease:

Aim: Development of an avian reovirus vaccine based on a live attenuated IBV strain that lacks nonessential genes.

Procedure: (Parts of) the protection related avian reovirus genes Φ1, Φ2, and 83 were placed into expression cassettes, and subsequently introduced into pFRAG3Δ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related avian reovirus genes Φ1, Φ2, and 83 can be introduced in and expressed from a live attenuated IBV strain. These recombinant viruses can therefore function as a multivalent vaccine to protect against avian reovirus and IBV infections.

IV.2.e. Construction of a Multivalent Vaccine Based on an IBV Vector that Protects Against Infectious Bursal Disease:

Aim: Development of an Infectious Bursal Disease Virus (IBDV) vaccine based on a live attenuated IBV strain that lacks nonessential genes.

Procedure: (Parts of) the protection related IBDV gene VP2 were placed into expression cassettes, and subsequently introduced into pFRAG3Δ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related IBDV gene VP2 can be introduced in and expressed from a live attenuated IBV strain. These recombinant viruses can therefore function as a multivalent vaccine to protect against avian IBDV and IBV infections.

IV.2.f. Construction of a Multivalent Vaccine Based on an IBV Vector that Protects Against Marek's Disease:

Aim: Development of a Gallid herpes virus 2 (Marek's disease virus) vaccine based on a live attenuated IBV strain that lacks nonessential genes.

Procedure: (Parts of) the protection related Gallid herpes virus 2 gene gB were placed into expression cassettes, and subsequently introduced into pFRAG3Δ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related Gallid herpes virus 2 gene gB can be introduced in and expressed from a live attenuated IBV strain. These recombinant viruses can therefore function as a multivalent vaccine to protect against Gallid herpes virus 2 and IBV infections.

IV.2.g. Construction of a Multivalent Vaccine Based on an IBV Vector that Protects Against Infectious Laryngotracheitis:

Aim: Development of a Gallid herpes virus 1 (Infectious laryngotracheitis virus) vaccine based on a live attenuated IBV strain that lacks nonessential genes.

Procedure: (Parts of) the protection related Gallid herpes virus 1 genes gB, gC, gD, gE, gH, gI, gK, gL, and gM were placed into expression cassettes, and subsequently introduced into pFRAG3Δ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related Gallid herpes virus 1 genes can be introduced in and expressed from a live attenuated IBV strain. These recombinant viruses can therefore function as a multivalent vaccine to protect against Gallid herpes virus 1 and IBV infections.

IV.3. Generation of Recombinant Viruses with Rearranged Gene Order:

Aim: Development of an IBV vaccine in which deletion of nonessential genes is combined with a rearranged gene order by moving the N gene upstream of the S gene in the IBV genome.

Procedure: Recombinant viruses were generated as described by Casais et al. (2001). Infectious IBV cDNA clones were assembled in the vaccinia virus genome by using sequential in vitro ligation of cDNA fragments derived from pFRAG1, pFRAG2, and pFRAG3 derived plasmids, followed by direct cloning into the genome of vaccinia virus vNotI/tk as described (1a). Genes 3a/b and 5a/b were removed from pFRAG3, by PCR mutagenesis leaving the surrounding open reading frames and transcription regulatory sequences intact. In addition, the N gene together with its TRS was moved to a position upstream of the S gene resulting in pFRAG3Δrearranged. Recombinant vaccinia viruses were generated by recombination between the fowlpox virus HP1.441 and the vNotI/tk-IBV in vitro ligation mixture. Recombinant viruses were plaque purified and characterized by PCR and Southern blot analysis. Finally, infectious IBV lacking genes 3a/b and 5a/b and with a rearranged gene order was generated as follows: Chick kidney (CK) cells were infected with recombinant fowl pox virus expressing T7 RNA polymerase. Subsequently, cells were transfected with DNA isolated from the recombinant vaccinia virus containing the IBV cDNA clone lacking genes 3a/b and 5a/b in combination with the rearranged gene order. At 3 days post-infection, the culture medium was collected and used to infect CK cells to generate large amounts of recombinant IBV. The recombinant viruses were genetically confirmed by RT-PCR analysis.

Conclusion: Recombinant IBV was generated that lacked the genes 3a/b and 5a/b in combination with a rearranged gene order. These viruses function as a live attenuated vaccine against IBV. When combined with S gene constructs from other IBV serotypes and/or gene constructs from other avian pathogens, additional multivalent vaccines can be generated.

V. Human Coronavirus (HCoV) Strain 229E (HCoV-229E):

V.1. Generation of a Live Vaccine Based on Attenuated HCoV-229E:

Aim: Development of a live attenuated vaccine against HCoV-229E.

Approach: Recombinant HCoV deletion mutant viruses were generated that lack the nonessential genes 4a/b.

Procedure: Recombinant viruses were generated essentially as described by Thiel et al. (2001). Infectious HCoV cDNA clones were assembled in the vaccinia virus genome. Vaccinia virus vDHCoV-vec-1 contains a 22.5 kbp cDNA fragment encoding the 5' end of the HCoV genome. This fragment was removed from the vaccinia genome by digestion with Bsp 120I, digested with MluI and ligated to a cDNA fragment of pMEΔ that was obtained by digestion with MluI/EagI. pMEΔ contains a cDNA fragment that encodes the 3' end of the HCoV genome, but lacks gene 4a/b, without disturbing the other genes or transcription regulatory sequences. pMEΔ was derived from pME by using conventional PCR mutagenesis methods. The ligation products were ligated to vNotI/tk vaccinia virus DNA. Recombinant vaccinia viruses were generated as described above. Recombinant viruses were plaque purified and characterized by PCR and Southern blot analysis. Finally, infectious HCoV lacking genes 4a/b was generated as follows: Chick kidney (CK) cells were infected with recombinant fowl pox virus expressing T7 RNA polymerase. Subsequently, cells were transfected with DNA isolated from the recombinant vaccinia virus containing the HCoV cDNA clone lacking genes 4a/b. At 3 days post-infection, the culture medium was collected and used to infect human lung fibroblast cells (MRC-5) to generate large amounts of recombinant HCoV. The recombinant viruses were genetically confirmed by RT-PCR analysis.

Conclusion: Recombinant HCoV was generated that lacked the genes 4a/b. These viruses can function as a live attenuated vaccine against HCoV-229E.

V.2. Generation of a Live Attenuated Vaccine Against HCoV Strain OC43:

Aim: Development of a live attenuated vaccine against HCoV-OC43.

Approach: Recombinant HCoV deletion mutant viruses were generated that lack the nonessential genes 4a/b, and contain a hybrid S protein gene, which encodes the ectodomain of HCoV-OC43.

Procedure: Recombinant viruses were generated essentially as described by Thiel et al. (2001). Infectious HCoV cDNA clones were assembled in the vaccinia virus genome. Vaccinia virus vHCoV-vec-1 contains a 22.5 kbp cDNA fragment encoding the 5' end of the HCoV genome. This fragment was removed from the vaccinia genome by digestion with Bsp 120I, digested with MluI and ligated to a cDNA fragment of pMEΔ-SOC43 that was obtained by digestion with MluI/EagI. pMEΔ-SOC43 contains a cDNA fragment that encodes the 3'end of the HCoV genome, lacks gene 4a/b, and contains a hybrid S protein gene, without disturbing the other genes or transcription regulatory sequences. The hybrid S protein gene contains the region of the S gene of HCoV-OC43 that encodes the S protein ectodomain, while the remainder of the gene is derived from the HCoV-229E gene. pMEΔ-SOC43 was derived from pMEΔ by using conventional (RT-)PCR mutagenesis methods. The ligation products were ligated to vNotI/tk vaccinia virus DNA. Recombinant vaccinia viruses were generated as described above. Recombinant viruses were plaque purified and characterized by PCR and Southern blot analysis. Finally, infectious HCoV lacking genes 4a/b was generated as follows: Chick kidney (CK) cells were infected with recombinant fowl pox virus expressing T7 RNA polymerase. Subsequently, cells were transfected with DNA isolated from the recombinant vaccinia virus containing the HCoV cDNA clone lacking genes 4a/b. At 3 days post-infection the culture medium was collected and used to infect human lung fibroblast cells (MRC-5) to generate large amounts of recombinant HCoV. The recombinant viruses were genetically confirmed by RT-PCR analysis.

Conclusion: Recombinant HCoV was generated that lacked the genes 4a/b. These viruses contain the ectodomain of the S protein of HCoV-OC43 and therefore function as a live attenuated vaccine against HCoV-OC43.

V.3. Generation of Multivalent HCoV-Based Vaccines:

Aim: Development of multivalent vaccine based on a live attenuated HCoV strain as a vector.

Approach: Expression cassettes of protection related genes of human pathogens were introduced into the HCoV genome in combination with attenuating deletion of nonessential genes. The expression cassettes contain the HCoV TRS (TCTCAACT) (SEQ ID NO:32) in front of (parts of) the gene to be expressed.

V.3.a. Construction of a Multivalent Vaccine Based on an HCoV Vector that Protects Against Respiratory Syncytial Virus (RSV):

Aim: Development of an RSV vaccine based on a live attenuated HCoV strain that lacks nonessential genes.

Procedure: (Parts of) the protection related RSV genes HN and F were placed into expression cassettes, and subsequently introduced into pMEΔ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related RSV genes HN and F can be introduced in and expressed from a live attenuated HCoV strain. These recombinant viruses can therefore function as a multivalent vaccine to protect against RSV and HCoV infections.

V.3.b. Construction of a Multivalent Vaccine Based on an HCoV Vector that Protects Against Rotavirus:

Aim: Development of a rotavirus vaccine based on a live attenuated HCoV strain that lacks nonessential genes.

Procedure: (Parts of) the protection related rotavirus genes VP4, VP6 and VP7 were placed into expression cassettes, and subsequently introduced into pMEΔ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related rotavirus genes VP4, VP6 and VP7 can be introduced in and expressed from a live attenuated HCoV strain. These recombinant viruses can therefore function as a multivalent vaccine to protect against rotavirus and HCoV infections.

V.3.c. Construction of a Multivalent Vaccine Based on an HCoV Vector that Protects Against Norwalk-Like Viruses:

Aim: Development of a Norwalk-like virus vaccine based on a live attenuated HCoV strain that lacks nonessential genes.

Procedure: (Parts of) the protection related Norwalk-like virus capsid gene was placed into expression cassettes, and subsequently introduced into pMEΔ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related Norwalk-like virus capsid gene can be introduced in and expressed from a live attenuated HCoV strain. This recombinant virus can therefore function as a multivalent vaccine to protect against Norwalk-like virus and HCoV infections.

V.3.d. Construction of a Multivalent Vaccine Based on an HcoV Vector that Protects Against Influenza Virus Aim: Development of an influenza virus vaccine based on a live attenuated HCoV strain that lacks nonessential genes.

Procedure: (Parts of) the protection related influenza virus genes H and N were placed into expression cassettes, and subsequently introduced into pMEΔ. After confirmation of all the constructs by restriction and sequence analysis, recombinant viruses were generated as described above. The recombinant viruses were genetically confirmed by RT-PCR analysis. Expression of the foreign gene was confirmed by immunoprecipitation analysis.

Conclusion: (Parts of) the protection related influenza virus genes H and N can be introduced in and expressed from a live attenuated HCoV strain. These recombinant viruses can therefore function as a multivalent vaccine to protect against influenza virus and HCoV infections.

V.4. Generation of Recombinant Viruses with Rearranged Gene Order:

Aim: Development of an HCoV vaccine in which deletion of nonessential genes is combined with a rearranged gene order by moving the N gene upstream of the S gene in the HCoV genome.

Procedure: Recombinant viruses were generated essentially as described by Thiel et al. (2001). Infectious HCoV cDNA clones were assembled in the vaccinia virus genome. Vaccinia virus vHCoV-vec-1 contains a 22.5 kbp cDNA fragment encoding the 5' end of the HCoV genome. This fragment was removed from the vaccinia virus genome by digestion with Bsp 120I, digested with MluI and ligated to a cDNA fragment of rearranged pMEΔ that was obtained by digestion with MluI/EagI. Rearranged pMEΔ contains a cDNA fragment that encodes the 3' end of the HCoV genome, but lacks gene 4a/b, without disturbing the other genes or transcription regulatory sequences, and in which the N gene, together with its TRS, was positioned upstream of the S gene. Rearranged pMEΔ was derived from pME by using conventional PCR mutagenesis methods. The ligation products were ligated to vNotI/tk vaccinia virus DNA. Recombinant vaccinia viruses were generated as described above. Recombinant viruses were plaque purified and characterized by PCR and Southern blot analysis. Finally, infectious HCoV lacking genes 4a/b was generated as follows: Chick kidney (CK) cells were infected with recombinant fowlpox virus expressing T7 RNA polymerase. Subsequently, cells were transfected with DNA isolated from the recombinant vaccinia virus containing the HCoV cDNA clone lacking genes 4a/b in combination with the rearranged gene order. At 3 days post-infection, the culture medium was collected and used to infect human lung fibroblast cells (MRC-5) to generate large amounts of recombinant HCoV. The recombinant viruses were genetically confirmed by RT-PCR analysis.

Conclusion: Recombinant HCoV was generated that lacked the genes 4a/b in combination with a rearranged gene order. These viruses can function as a live attenuated vaccine against HCoV-229E. When combined with S gene constructs from HcoV-OC43 and/or gene constructs from other human pathogens, additional multivalent vaccines can be generated.

REFERENCES

1. Bredenbeek, P. J., C. J. Pachuk, A. F. Noten, J. Charite, W. Luytjes, S. R. Weiss, and W. J. Spaan. 1990. The primary structure and expression of the second open reading frame of the polymerase gene of the coronavirus MHV-A59; a highly conserved polymerase is expressed by an efficient ribosomal frameshifting mechanism. Nucleic Acids Res. 18:1825-32.

1a. Casais, R., V. Thiel, S. G. Siddell, D. Cavanagh, and P. Britton. 2001. Reverse genetics system for the avian coronavirus infectious bronchitis virus. J. Virol. 75:12359-12369.

1c. Almazan, F., J. M. Gonzalez, Z. Penzes, A. Izeta, E. Calvo, J. Plana-Duran, and L. Enjuanes. 2000. Engineering the largest RNA virus genome as an infectious bacterial artificial chromosome. Proc. Natl. Acad. Sci. USA 97:5516-5521.

1d. Fischer, F., C. F. Stegen, C. A. Koetzner, and P. S. Masters. 1997. Analysis of a recombinant Mouse Hepatitis Virus Expressing a foreign gene reveals a novel aspect of coronavirus transcription. J. Virol. 71:5148-5160.

2. Fischer, F., D. Peng, S. T. Hingley, S. R. Weiss, and P. S. Masters. 1997. The internal open reading frame within the nucleocapsid gene of mouse hepatitis virus encodes a structural protein that is not essential for viral replication. J. Virol. 71:996-1003.

2a. Herrewegh, A. A., I. Smeenk, M. C. Horzinek, P. J. M. Rottier, and R. J. de Groot. 1998. Feline coronavirus type II strains 79-1683 and 79-1146 originate from a double recombination between feline coronavirus type I and canine coronavirus. J Virol. 72:4508-4514.

3. Hsue, B., T. Hartshorne, and P. Masters. 2000. Characterization of an essential RNA secondary structure in the 3' untranslated region of the murine coronavirus genome. J. Virol. 74:6911-6921.

4. Hsue, B., and P. S. Masters. 1999. Insertion of a new transcriptional unit into the genome of mouse hepatitis virus. J. Virol. 73:6128-6135.

5. Jacobs, L., W. Spaan, M. Horzinek, and B. van der Zeijst. 1981. Synthesis of subgenomic mRNA's of mouse hepatitis virus is initiated independently: evidence from UV transcription mapping. J. Virol. 39:401-406.

6. Jendrach, M., V. Thiel, and S. Siddell. 1999. Characterization of an internal ribosome entry site within mRNA 5 of murine hepatitis virus. Arch. Virol. 144:921-933.

7. Kuo, L., G. Godeke, M. Raamsman, P. Masters, and P. Rottier. 2000. Retargeting of coronavirus by substitution of the spike glycoprotein ectodomain: crossing the host cell species barrier. J. Virol. 74:1393-1406.

8. Leibowitz, J., K. Wilhelmsen, and C. Bond. 1981. The virus-specific intracellular RNA species of two murine coronaviruses: MHV-a59 and MHV-JHM. Virology. 114:39-51.

9. Masters, P. S. 1999. Reverse genetics of the largest RNA viruses. 53:245-264, Adv. Virus Res. 53:245-264.

10. Masters, P. S., C. A. Koetzner, C. A. Kerr, and Y. Heo. 1994. Optimization of targeted RNA recombination and mapping of a novel nucleocapsid gene mutation in the coronavirus mouse hepatitis virus. J Virol. 68:328-37.

10a. Thiel, V., J. Herold, B. Schelle, and S. Siddell. 2001. Infectious RNA transcribed in vivo from a cDNA copy of the human coronavirus genome cloned in vaccinia virus. J. Gen. Virol. 82, 1273-1281

11. de Vries, A. A. F, A. L. Glaser, M. J. B. Raamsman, C. A. M. de Haan, S. Sarnataro, G.-J. Godeke, and P. J. M. Rottier. 2000. Genetic manipulation of equine arteritis virus using full-length cDNA clones: separation of overlapping genes and expression of a foreign epitope. Virology 270:84-97.
12. Godeke, G.-J., C. A. M. de Haan, J. W. A. Rossen, I. L. Vennema, and P. J. M. Rottier. 2000. Assembly of spikes into coronavirus particles is mediated by the carboxy-terminal domain of the spike (S) protein. J. Virol. 74:1566-1571.
13. Vennema, H., G.-J. Godeke, J. W. A. Rossen, W. F. Voorhout, M. C. Horzinek, D.-J. E. Opstelten, and P. J. M. Rottier. 1996. Nucleocapsid-independent assembly of coronavirus-like particles by coexpression of viral envelope proteins. EMBO J. 15:2020-2028.

What is claimed is:

1. An isolated or recombinant virus-like particle comprising nucleic acid and capable of replication in a suitable host, said isolated or recombinant virus-like particle derived from a coronavirus wherein the coronavirus' genes for structural proteins do not occur in the order 5'-S-E-M-N-3' and wherein the order of the coronavirus' genes for structural proteins has been altered by gene rearrangement, wherein the gene rearrangement comprises deleting at least one gene for a structural proteins from it's original position relative to the remaining genes for structural proteins and inserting said deleted at least one gene for a structural protein in a different genomic location relative to the remaining genes for structural proteins.

2. The isolated or recombinant virus-like particle of claim 1 from which at least a fragment from a nucleic acid encoding a viral gene product other than a polymerase or a structural protein N, M, E, or S, is deleted.

3. The isolated or recombinant virus-like particle of claim 1, wherein said isolated or recombinant virus-like particle has been provided with at least one biologically active protein or fragment thereof associated with the surface of said isolated or recombinant virus-like particle other than the natural ectodomain of any one protein of the coronavirus from which the isolated or recombinant virus-like particle has been derived.

4. The isolated or recombinant virus-like particle of claim 2, wherein said isolated or recombinant virus-like particle has been provided with at least one biologically active protein or fragment thereof associated with the surface of said isolated or recombinant virus-like particle other than the natural ectodomain of any one protein of the coronavirus from which the isolated or recombinant virus-like particle has been derived.

5. The isolated or recombinant virus-like particle of claim 1, wherein said isolated or recombinant virus-like particle has been provided with a at least one functional targeting means associated with the surface of said isolated or recombinant virus-like particle other than the natural spike protein of the coronavirus from which the isolated or recombinant virus-like particle has been derived.

6. The isolated or recombinant virus-like particle of claim 1, wherein said isolated or recombinant virus-like particle has been provided with a coronavirus genome comprising a foreign gene or part thereof.

7. The isolated or recombinant virus-like particle of claim 1, which is attenuated.

8. The isolated or recombinant virus-like particle of claim 1, which is a gene delivery vehicle.

9. The isolated or recombinant virus-like particle of claim 1, which is an antigen or epitope delivery vehicle.

10. A immunogenic composition comprising:
    the isolated or recombinant virus-like particle of claim 1, and
    a pharmaceutically acceptable carrier.

11. A composition for diagnostic use comprising:
    the isolated or recombinant virus-like particle of claim 1 presented in a manner capable of diagnostic determination.

12. An isolated or recombinant virus-like particle comprising nucleic acid and capable of replication in a suitable host, said isolated or recombinant virus-like particle derived from a coronavirus wherein the coronavirus' genes for structural proteins occur in an order selected from the group consisting of 5'-S-M-E-N-3', 5'-E-S-M-N-3', 5'-E-M-S-N-3', and 5'-M-S-E-N-3'.

13. An isolated or recombinant virus-like particle comprising nucleic acid and capable of replication in a suitable host, said isolated or recombinant virus-like particle derived from a coronavirus where the coronavirus' genes do not occur in the order 5'-S-E-M-N-3', and wherein only one copy of the S, E, M, and N genes is present in the recombination virus-like particle.

* * * * *

UNITED STATES PATENT AND TRADEMARK OFFICE
CERTIFICATE OF CORRECTION

PATENT NO.        : 7,556,957 B2
APPLICATION NO.   : 10/714534
DATED             : July 7, 2009
INVENTOR(S)       : Petrus Josephus Marie Rottier, Cornelis Alexander Maria De Haan and Bert Jan Haijema Page 1 of 1

It is certified that error appears in the above-identified patent and that said Letters Patent is hereby corrected as shown below:

In the specification:

| | | |
|---|---|---|
| COLUMN 5, | LINE 16, | change "immunoglobulinimmunoglobulins" to --immunoglobulins-- |
| COLUMN 5, | LINE 30, | change "immunoglobulinimmunoglobulin" to --immunoglobulin-- |
| COLUMN 5, | LINE 52, | change "nonessentialnonessential" to --nonessential-- |
| COLUMN 5, | LINE 61, | change "nonessentialnonessential" to --nonessential-- |
| COLUMN 5, | LINE 65, | change "notexpressed)," to --not expressed),-- |
| COLUMN 8, | LINE 8, | change "chimericchimeric" to --chimeric-- |
| COLUMN 8, | LINES 13,14 | change "chimericchimeric" to --chimeric-- |
| COLUMN 8, | LINE 22, | change "chimericchimeric" to --chimeric-- |
| COLUMN 9, | LINE 20, | change "chimericchimeric" to --chimeric-- |
| COLUMN 15, | LINE 19, | change "Primer 2" to --Primer 5-- |

Signed and Sealed this
Nineteenth Day of November, 2013

Teresa Stanek Rea
*Deputy Director of the United States Patent and Trademark Office*

SEQUENCE LISTING

<160> NUMBER OF SEQ ID NOS: 80

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: primer 1089

<400> SEQUENCE: 1
acctgcagga ctaatctaaa ctttattctt tttagggcca cgc        43

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: primer 1092

<400> SEQUENCE: 2
ccttaaggaa ttgaactgc        19

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: primer 1128

<400> SEQUENCE: 3
acggtccgac tgcgcgcttg aacacgttg        29

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: primer 1130

<400> SEQUENCE: 4
catgcaagct ttatttgaca tttactaggc t        31

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: primer 1129

<400> SEQUENCE: 5
gtcaaataaa gcttgcatga ggcataatct aaac        34

<210> SEQ ID NO 6
<211> LENGTH: 19
<212> TYPE: DNA

```
<213> ORGANISM: Artificial Sequence
<220> FEATURE:
<223> OTHER INFORMATION: Description of Artificial Sequence: primer 1127

<400> SEQUENCE: 6
ccagtaagca ataatgtgg                                                    19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer 1261

<400> SEQUENCE: 7
gctgcttact cctatcatac                                                   20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer 990

<400> SEQUENCE: 8
cctgatttat ctctcgattt c                                                 21

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: primer 1173

<400> SEQUENCE: 9
gacttagtcc tctccttga                                                    19

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: primer 1260

<400> SEQUENCE: 10
cttcaacggt ctcagtgc                                                     18

<210> SEQ ID NO 11
<211> LENGTH: 9
<212> TYPE: RNA
<213> ORGANISM: mouse hepatitis virus
<220> FEATURE:
<221> NAME/KEY: misc_feature
<222> LOCATION: (1)..(9)
<223> OTHER INFORMATION: /note="Consensus transcription regulatory
      signal"

<400> SEQUENCE: 11 aaucuaaac                                                                9

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: primer 1C
```

```
<400> SEQUENCE: 12
gtgtatagat atgaaaggta ccgtg                                              25

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer 1097

<400> SEQUENCE: 13
cgaaccagat cggctagcag                                                    20

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: primer 1095

<400> SEQUENCE: 14
agattagata tcttaggttc tcaacaatgc gg                                      32

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: primer 1096

<400> SEQUENCE: 15
gaacctaaga tatctaatct aaactttaag gatg                                    34

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: primer 1286

<400> SEQUENCE: 16
ggatactaat ctaaacttta g                                                  21

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: primer 1287

<400> SEQUENCE: 17
ctagctaaag tttagattag atatcctgca                                         30

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: primer 1412

<400> SEQUENCE: 18
ctgcggacca gttatcatc                                                     19

<210> SEQ ID NO 19
<211> LENGTH: 34
```

```
<212> TYPE: DNA
<213> ORGANISM: Artificial Sequence
<220> FEATURE:
<223> OTHER INFORMATION: Description of Artificial Sequence: primer 1091

<400> SEQUENCE: 19
gttacaaacc tgaatctcat cttaattctg gtcg                                    34

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: primer 1413

<400> SEQUENCE: 20
catccgtttc ctttgttctg g                                                  21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: primer 1173

<400> SEQUENCE: 21
gacttagtcc tctccttgat tg                                                 22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: primer 1475

<400> SEQUENCE: 22
gcctaatgca gttgctctcc                                                    20

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: primer 935

<400> SEQUENCE: 23
gttttagcac agggtgtggc tcatg                                              25

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: primer 1474

<400> SEQUENCE: 24
ccatcttcca gcggatag                                                      18

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: forward
      primer

<400> SEQUENCE: 25
```

```
gcggatccat cgaaggtcgt gatttatctc tcgatttc                              38

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: reverse
      primer

<400> SEQUENCE: 26
cgaattcatt ccttgaggtt gatgtag                                          27

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: primer 1244

<400> SEQUENCE: 27
gccattctca ttgataac                                                    18

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: primer 1514

<400> SEQUENCE: 28
ctgagtctag agtagctagc taatgactaa taagtttag                             39

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: primer 1245

<400> SEQUENCE: 29
gcttctgttg agtaatcacc                                                  20

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: primer 1513

<400> SEQUENCE: 30
gctagctact ctagactcag gcggttctaa ac                                    32

<210> SEQ ID NO 31
<211> LENGTH: 8
<212> TYPE: DNA
<213> ORGANISM: Coronavirus sp.
<220> FEATURE:
<223> OTHER INFORMATION: /Note="Infectious Bronchitis Coronavirus TRS"

<400> SEQUENCE: 31 cttaacaa                                                                8

<210> SEQ ID NO 32
<211> LENGTH: 8
```

```
<212> TYPE: DNA
<213> ORGANISM: Human Coronavirus sp.
<220> FEATURE:
<223> OTHER INFORMATION: /Note="Human Coronavirus TRS"

<400> SEQUENCE: 32 tctcaact                                                              8

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: sequence of
      new junction created in recombinant MHV-virus

<400> SEQUENCE: 33
gaggattgac tat

<210> SEQ ID NO 38
<211> LENGTH: 36
<212> TYPE: DNA
<213> ORGANISM: Artificial Sequence
<220> FEATURE:
<223> OTHER INFORMATION: Description of Artificial Sequence: pBRDI
      sequence at the pol 1A/pol1B junction

<400> SEQUENCE: 38
gttattgaag gtgagctctg gactgtgttt tgtaca                              36

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: protein
      sequence derived from pBRDI sequence at the
      pol1A/1B junction

<400> SEQUENCE: 39

Val Ile Glu Gly Glu Leu Trp Thr Val Phe Cys Thr
 1               5                  10

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence:  pBRDI
      sequence at the 3' end of the cDNA construct

<400> SEQUENCE: 40
tagtgataca aaaaaaaaaa aaagcggccg c                                   31

<210> SEQ ID NO 41
<211> LENGTH: 54
<212> TYPE: DNA
<213> ORGANISM: Artificial Sequence
<220> FEATURE:
<223> OTHER INFORMATION: Description of Artificial Sequence: nucleotide
      sequence at the FIPV pol1B-MHV S transition in
      pTMFS1 and pBRDI2

<400> SEQUENCE: 41
gttaatgtgc catgctgttc gtgtttattc tatttttgcc ctcttgttta gggt 54

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: protein sequence derived from nucleotide sequence at the FIPV pol1B-MHV S transition in pTMFS1 and pBRDI2

<400> SEQUENCE: 42

Pro Cys Cys Ser Cys Leu Phe Tyr Phe Cys Pro Leu Val
1 5 10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: protein sequence derived from nucleotide sequence at the FIPV pol1B-MHV S transition in pTMFS1 and pBRDI2

-continued

<400> SEQUENCE: 43

```
Met Leu Phe Val Phe Ile Leu Phe Leu Pro Ser
  1               5                  10
```

<210> SEQ ID NO 44
<211> LENGTH: 25
<212> TYPE: PRT
<213> ORGANISM: mouse hepatitis virus

<400> SEQUENCE: 44

```
Ser Ser Tyr Gly Met Ser Glu Ser Ala Asp Ala Asn Gly Ser Ala Glu
1               5                   10                  15

Asn Asn Ser Arg Leu Thr Glu Lys Asn
            20                  25
```

<210> SEQ ID NO 45
<211> LENGTH: 25
<212> TYPE: PRT
<213> ORGANISM: Human coronavirus

<400> SEQUENCE: 45

```
Tyr Asn Tyr Gly Met Ser Gln Asn Tyr Ala Asp Ala Asn Val Ala Ala
1               5                   10                  15

Glu Asn Gln Ser Arg Leu Ser Glu Asn
            20                  25
```

<210> SEQ ID NO 46
<211> LENGTH: 42
<212> TYPE: PRT
<213> ORGANISM: Human coronavirus

<400> SEQUENCE: 46

```
Ser Ala Tyr Gln Thr Gln Glu Ala Lys Thr Asn Val Thr Gly Val Asn
1               5                   10                  15

Asp Ala Ile Thr Gln Thr Ser Gln Ala Leu Gln Val Ala Asn Gln Asn
            20                  25                  30

His Thr Ser Arg Gln Ala Asp Thr Gln Gln
        35                  40
```

<210> SEQ ID NO 47
<211> LENGTH: 43
<212> TYPE: PRT
<213> ORGANISM: Feline infectious peritonitis virus

<400> SEQUENCE: 47

```
Ala Ala Tyr Gln Thr Asn Lys Gln Asn Asn Thr Gln Gly Lys Val Asn
1               5                   10                  15

Asp Ala Ile His Gln Thr Ser Gln Gly Leu Ala Val Ala Lys Ala Thr
            20                  25                  30

Gln Ser His Thr Val Gln Gln Ser Asn Glu Ser
        35                  40
```

<210> SEQ ID NO 48
<211> LENGTH: 36
<212> TYPE: PRT
<213> ORGANISM: Infectious bronchitis virus

<400> SEQUENCE: 48

```
Ala Thr Gln His Gln Ser Leu Lys Glu Lys Ala Lys His Arg Ser Leu
1               5                   10                  15
```

```
Gln Gln Ser Lys Ser Ala Ile Thr Glu Thr Ala Ser Asn Lys Val Gln
            20                  25                  30

Gln Phe Gln Asn
        35

<210> SEQ ID NO 49
<211> LENGTH: 102
<212> TYPE: PRT
<213> ORGANISM: Artificial Sequence
<220> FEATURE:
<223> OTHER INFORMATION: Description of Artificial Sequence:
      peptide HR1

<400> SEQUENCE: 49

Gly Pro Ile Glu Gly Arg Gln Tyr Arg Ile Asn Gly Leu Gly Val Thr
1               5                   10                  15

Met Asn Val Leu Ser Glu Asn Gln Lys Met Ile Ala Ser Ala Phe Asn
            20                  25                  30

Asn Ala Leu Gly Ala Ile Gln Asp Gly Phe Asp Ala Thr Asn Ser Ala
        35                  40                  45

Leu Gly Lys Ile Gln Ser Val Val Asn Ala Asn Ala Glu Ala Leu Asn
    50                  55                  60

Asn Leu Leu Asn Gln Leu Ser Asn Arg Phe Gly Ala Ile Ser Ala Ser
65                  70                  75                  80

Leu Gln Glu Ile Leu Thr Arg Leu Glu Ala Val Glu Ala Lys Ala Gln
                85                  90                  95

Ile Asp Arg Leu Ile Asn
            100

<210> SEQ ID NO 50
<211> LENGTH: 82
<212> TYPE: PRT
<213> ORGANISM: Artificial Sequence
<220> FEATURE:
<223> OTHER INFORMATION: Description of Artificial Sequence:
      peptide HR1a

<400> SEQUENCE: 50

Gly Pro Asn Gln Lys Met Ile Ala Ser Ala Phe Asn Asn Ala Leu Gly
1               5                   10                  15

Ala Ile Gln Asp Gly Phe Asp Ala Thr Asn Ser Ala Leu Gly Lys Ile
            20                  25                  30

Gln Ser Val Val Asn Ala Asn Ala Glu Ala Leu Asn Asn Leu Leu Asn
        35                  40                  45

Gln Leu Ser Asn Arg Phe Gly Ala Ile Ser Ala Ser Leu Gln Glu Ile
    50                  55                  60

Leu Thr Arg Leu Glu Ala Val Glu Ala Lys Ala Gln Ile Asp Arg Leu
65                  70                  75                  80

Ile Asn

<210> SEQ ID NO 51
<211> LENGTH: 49
<212> TYPE: PRT
<213> ORGANISM: Artificial Sequence
<220> FEATURE:
<223> OTHER INFORMATION: Description of Artificial Sequence:
      peptide HR1b

<400> SEQUENCE: 51

Gly Pro Asn Gln Lys Met Ile Ala Ser Ala Phe Asn Asn Ala Leu Gly
1               5                   10                  15
```

-continued

```
Ala Ile Gln Asp Gly Phe Asp Ala Thr Asn Ser Ala Leu Gly Lys Ile
            20                  25                  30

Gln Ser Val Val Asn Ala Asn Ala Glu Ala Leu Asn Asn Leu Leu Asn Gln
        35                  40                  45

<210> SEQ ID NO 52
<211> LENGTH: 52
<212> TYPE: PRT
<213> ORGANISM: Artificial Sequence
<220> FEATURE:
<223> OTHER INFORMATION: Description of Artificial Sequence:
      peptide HR1c

<400> SEQUENCE: 52

Gly Pro Ile Glu Gly Arg Asn Ala Asn Ala Glu Ala Leu Asn Asn Leu
1               5                   10                  15

Leu Asn Gln Leu Ser Asn Arg Phe Gly Ala Ile Ser Ala Ser Leu Gln
            20                  25                  30

Glu Ile Leu Thr Arg Leu Glu Ala Val Glu Ala Lys Ala Gln Ile Asp
        35                  40                  45

Arg Leu Ile Asn
    50

<210> SEQ ID NO 53
<211> LENGTH: 17
<212> TYPE: PRT
<213> ORGANISM: mouse hepatitis virus

<400> SEQUENCE: 53

Phe Glu Lys Leu Tyr Asn Asp Ala Lys Lys Glu Tyr Glu Gly Thr Tyr
1               5                   10                  15

Met

<210> SEQ ID NO 54
<211> LENGTH: 17
<212> TYPE: PRT
<213> ORGANISM: Human coronavirus

<400> SEQUENCE: 54

Tyr Ile Phe Gln Val Asn Glu Ala Lys Val Gln Tyr Asp Gly Thr Tyr
1               5                   10                  15

Tyr

<210> SEQ ID NO 55
<211> LENGTH: 27
<212> TYPE: PRT
<213> ORGANISM: Human coronavirus

<400> SEQUENCE: 55

Val Gln Gln Ser Ser Thr Asn Lys Ser Ala Glu Leu Asn Tyr Thr Val
1               5                   10                  15

Gln Lys Leu Gln Thr Asp Asn Ser Trp Asn Arg
            20                  25

<210> SEQ ID NO 56
<211> LENGTH: 29
<212> TYPE: PRT
<213> ORGANISM: Feline infectious peritonitis virus

<400> SEQUENCE: 56

Phe Ile Ala Tyr Gly Asp Asp Phe Arg Ser Glu Lys Leu His Asn Thr
```

-continued

```
                1               5                  10                 15
Thr Val Glu Leu Ala Ile Asp Asn Asn Glu Trp Asn Arg
            20                  25

<210> SEQ ID NO 57
<211> LENGTH: 19
<212> TYPE: PRT
<213> ORGANISM: Infectious bronchitis virus

<400> SEQUENCE: 57

Phe Asp Lys Phe Asn Thr Pro Asp Ser Asp Gly Gln Gly Asp Glu Lys
1               5                   10                  15

Ser Ile Lys

<210> SEQ ID NO 58
<211> LENGTH: 45
<212> TYPE: PRT
<213> ORGANISM: Artificial Sequence
<220> FEATURE:
<223> OTHER INFORMATION: Description of Artificial Sequence: peptide HR2

<400> SEQUENCE: 58

Gly Pro Ile Glu Gly Arg Asp Leu Ser Leu Asp Phe Glu Lys Leu Asn
 1               5                  10                  15

Val Thr Leu Leu Asp Leu Thr Tyr Glu Met Asn Arg Ile Gln Asp Ala
            20                  25                  30

Ile Lys Lys Leu Asn Glu Ser Tyr Ile Asn Leu Lys Glu
            35                  40                  45

<210> SEQ ID NO 59
<211> LENGTH: 53
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 59
gaggattgac tatcacagcc cctgcaggaa agacagaaaa tctaaacaat tta              53

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 60
gaggattgac tatcacagcc ccatctaatc aaacattat g                            41

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 61
agaacctaag atggaaagac agaaaatcta aacaattta                              39

<210> SEQ ID NO 62
<211> LENGTH: 26
```

```
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 62
gatatctaat ctaaacttta aggatg                                          26

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 63
gtcaaataaa gcttgcatga ggcataatct aaacatg                              37

<210> SEQ ID NO 64
<211> LENGTH: 38
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 64
gtcaaataag cggaaagaca gaaaatctaa acaattta                             38

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 65
agaacctaag atagcttgca tgaggcataa tctaaacatg                           40

<210> SEQ ID NO 66
<211> LENGTH: 28
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 66
gaggattgac tatcacagcc cccgcgca                                        28

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: sequence of
      junction generated in recombinant MHV-virus

<400> SEQUENCE: 67
gtcaaataaa gctatctaat ccaaacatta tg                                   32

<210> SEQ ID NO 68
<211> LENGTH: 18
<212> TYPE: DNA
```

```
<213> ORGANISM: Artificial Sequence
<220> FEATURE:
<223> OTHER INFORMATION: Description of Artificial Sequence: primer 1
      for SOE-PCR

<400> SEQUENCE: 68
gccattctca ttgataac                                              18

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: primer 2
      for SOE-PCR

<400> SEQUENCE: 69
gcttctgttg agtaatcacc                                            20

<210> SEQ ID NO 70
<211> LENGTH: 34
<212> TYPE: DNA
<213> ORGANISM: Artificial Sequence
<220> FEATURE:
<223> OTHER INFORMATION: Description of Artificial Sequence: primer 3
      for SOE-PCR

<400> SEQUENCE: 70
gtcattacag gtcttgtatg acgttcccta gggc                            34

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: primer 4
      for SOE-PCR

<400> SEQUENCE: 71
catacaagac ctgtaatgac                                            20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: primer 5
      for SOE-PCR

<400> SEQUENCE: 72
ggtgattact caacagaagc                                            20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: primer 6
      for SOE-PCR

<400> SEQUENCE: 73
gcggccgctt tttttttttt                                            20

<210> SEQ ID NO 74
<211> LENGTH: 33
<212> TYPE: DNA
<213> ORGANISM: Artificial Sequence
```

```
<220> FEATURE:
<223> OTHER INFORMATION: Description of Artificial Sequence: primer 7
      for SOE-PCR

<400> SEQUENCE: 74
gaggttacga attaaactga gttataaggc aac                                     33

<210> SEQ ID NO 75
<211> LENGTH: 16
<212> TYPE: DNA
<213> ORGANISM: Artificial Sequence
<220> FEATURE:
<223> OTHER INFORMATION: Description of Artificial Sequence: primer 8
      for SOE-PCR

<400> SEQUENCE: 75
tttaattcgt aacctc                                                        16

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: primer 9
      for SOE-PCR

<400> SEQUENCE: 76
caggagccag aagaagacgc taa                                                23

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: primer 10
      for SOE-PCR

<400> SEQUENCE: 77
ctcaatctag aggaagacac c                                                  21

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: primer 11
      for SOE-PCR

<400> SEQUENCE: 78
gaccagtttt agacatcg                                                      18

<210> SEQ ID NO 79
<211> LENGTH: 14196
<212> TYPE: DNA
<213> ORGANISM: Artificial Sequence
<220> FEATURE:
<223> OTHER INFORMATION: Description of Artificial Sequence: sequence of
      plasmid pBRDI1

<400> SEQUENCE: 79
ctcgagtcga aattaatacg actcactata gggtttttaa agtaaagtga gtgtagcgtg        60
gctataactc ttcttttact ttaactagcc ttgtgctaga tttgtcttcg gacaccaact       120
cgaactaaac gaaatatttg tctctctatg aaaccataga agacaagcgt tgattatttc       180
accagtttgg caatcactcc taggaacggg gttgagagaa cggcgcacca gggttccgtc       240
```

```
cctgtttggt aagtcgtcta gtattagctg cggcggttcc gcccgtcgta gttgggtaga    300
ccgggttccg tcctgtgatc tccctcgccg gccgccagga gaatgagttc caaacaattt    360
aagatcctcg ttaatgagga ctaccaagtc aacgttccta gccttccttt ccgtgacgca    420
ctgcaggaaa ttaagtactg ctaccgtaac ggttttgatg gctatgtctt cgtgcctgaa    480
taccgtcgtg acctagttga ttgcaatcgt aaggatcact acgtcattgg tgttttgggt    540
aacggaataa gtgatcttaa acctgttctc cttaccgaac cttccgtcat gttgcagggt    600
ttcattgtta gagccaactg caatggcgtt cttgaggact ttgaccttaa attcgcccgt    660
actggaaacg gcgccatata tgtggaccaa tacatgtgtg gtgctgatgg aaagccagtt    720
attgaaggtg agctctggac tgtgttttgt acaagtgtta atacgtcatc atcagaaggt    780
tttctgattg gtattaacta cttaggacca tactgtgaca aagcaatagt agatggaaat    840
ataatgcatg ccaattatat attttggaga aactctacaa ttatggctct atcacataac    900
tcagtcctag acactccaaa atttaagtgc cgttgtaaca atgcacttat tgttaattta    960
aaagaaaaag aattgaatga aatggtcgtt ggattactaa ggaagggtaa gttactcatt    1020
agaaataatg gcaagctact aaactttggt aatcatttag ttaatgtgcc atgattgtgc    1080
tcgtaacttg cctcttgttg ttatgttcat accacacagt tttgagtaca caaataatg    1140 aatgcataca agttaacgta acacaattgg ctggcaatga aaaccttatc agagattttc    1200
tgtttagtaa ctttaaagaa gaaggaagtg tagttgttgg tggttattac cctacagagg    1260
tgtggtacaa ctgctctaga acagtcgaa ctactgcctt tcagtatttt aataatatac    1320 atgccttta ttttgttatg gaagccatgg aaaatagcac tggtaatgca cgtggtaaac    1380
cattattatt tcatgtgcat ggtgagcctg ttagtgttat tatatcggct tatagggatg    1440
atgtgcaaca aaggccccctt ttaaaacatg gttagtgtg cataactaaa aatcgccata    1500
ttaactatga acaattcacc tccaaccagt ggaattccac atgtacgggt gctgacagaa    1560
aaattccttt ctctgtcata cccacggaca atggaacaaa aatctatggt cttgagtgga    1620
atgatgactt tgttacagct tatattagtg gtcgttctta tcacttgaac atcaatacta    1680 attggttta caatgtcaca ctttttgtatt cacgctcaag cactgctacc tgggaataca    1740
gtgctgcata tgcttaccaa ggtgtttcta acttcactta ttacaagtta aataacacca    1800
atggtctaaa aacctatgaa ttatgtgaag attatgaaca ttgcactggc tatgctacca    1860
atgtatttgc tccgacatca ggtggttaca tacctgatgg atttagttt aacaattggt    1920 tcttgcttac aaatagttcc acttttgtta gtggcaggtt tgtaacaaat caaccattat    1980
tgattaattg cttgtggcca gtgcccagtt ttggtgtagc agcacaagaa ttttgttttg    2040
aaggtgcaca gtttagccaa tgtaatggtg tgtctttaaa taacacagtg gatgttatta    2100 gattcaaccct taatttcact gcagatgtac aatctggtat gggtgctaca gtatttttcac    2160 tgaatacaac aggtggtgtc attcttgaaa tttcatgtta tagtgacaca gtgagtgagt    2220
ctagttctta cagttatggt gaaatcccgt tcggcataac tgacggacca cgatactgtt    2280
atgtacttta caatggcaca gctcttaaat atttaggaac attaccaccc agtgtaaagg    2340
aaattgctat tagtaagtgg ggccattttt atattaatgg ttacaatttc tttagcacat    2400
ttcctattgg ttgtatatct tttaatttaa ccactggtgt tagtggagct ttttggacaa    2460
ttgcttacac atcgtatact gaagcattag tacaagttga aaacacagct attaaaatg    2520 tgacgtattg taacagtcac attaataaca ttaaatgttc tcaacttact gctaatttga    2580
ataatggatt ttatcctgtt gcttcaagtg aagtaggttt cgttaataag agtgttgtgt    2640
```

```
tattacctag cttttcaca tacaccgctg tcaatataac cattgatctt ggtatgaagc    2700
ttagtggtta tggtcaaccc atagcctcga cactaagtaa catcacacta ccaatgcagg    2760
ataacaatac tgatgtgtac tgtattcgtt ctaaccaatt ctcagtttat gttcattcca    2820
cttgcaaaag ttctttatgg gacaatattt ttaatcaaga ctgcacggat gttttagagg    2880
ctacagctgt tataaaaact ggtacttgtc ctttctcatt tgataaattg aacaattact    2940
tgacttttaa caagttctgt ttgtcgttga gtcctgttgg tgctaattgc aagtttgatg    3000
ttgctgcacg tacaagaacc aatgagcagg ttgttagaag tctatatgta atatatgaag    3060
aaggagacaa catagtgggt gtaccgtctg ataatagcgg tctgcacgat tgtctgtgc     3120 tacacctaga ctcctgtaca gattacaata tatatggtag aactggtgtt ggtattatta    3180
gacgaactaa cagtacgcta cttagtggct tatattacac atcactatca ggtgatttgt    3240
taggctttaa aaatgttagt gatggtgtca tttattctgt gacgccatgt gatgtaagcg    3300
cacaagcggc tgttattgat ggtgccatag ttggagctat gacttccatt aacagtgaac    3360
tgttaggtct aacacattgg acaacgacac ctaattttta ttactactct atatataatt    3420
acacaagtga gaggactcgt ggcactgcaa ttgacagtaa cgatgttgat tgtgaacctg    3480
tcataaccta ttctaatata ggtgtttgta aaaatggtgc tttggttttt attaacgtca    3540
cacattctga cggagacgtg caaccaatta gcactggtaa tgtcacgata cctacaaatt    3600
ttactatatc tgtgcaagtt gaatacatgc aggtttacac tacaccagta tcaatagatt    3660
gtgcaagata cgtttgtaat ggtaaccta gatgtaacaa attgttaaca caatatgtgt    3720
ctgcatgtca aactattgaa caagcacttg caatgggtgc cagacttgaa acatggagg    3780 ttgattccat gttgtttgtc tcggaaaatg cccttaaatt ggcatctgtt gaggcgttca    3840
atagtacaga aaatttagat cctatttaca agaatggcc tagcataggt ggttcttggc    3900
taggaggtct aaaagatata ctaccgtccc ataatagcaa acgtaagtat ggttctgcta    3960
tagaagattt gctttttgat aaagttgtaa catctggttt aggtacagtt gatgaagatt    4020
ataaacgttg tactggtggt tacgacatag cagacttggt gtgtgctcaa tattacaatg    4080
gcatcatggt tctaccaggt gtagctaatg ctgacaagat gactatgtac acagcatcac    4140
ttgcaggtgg tataacatta ggtgcacttg gtggtgcgc cgtggctata ccttttgcag    4200
tagcagtaca ggctagactt aattatgttg ctctacaaac tgatgtattg aataaaaacc    4260
aacagatcct ggctaatgct ttcaatcaag ctattggtaa cattacacag gcttttggta    4320
aggttaatga tgctatacat caaacatcac aaggtcttgc cactgttgct aaagcgttgg    4380
caaaagtgca agatgttgtc aacacacaag gcaagctttt aagtcacctt acagtacaat    4440
tgcaaaataa ttttcaagcc attagtagtt ctattagtga tatttataac aggcttgacg    4500
aactgagtgc tgatgcacaa gttgataggc tgattacagg tagacttaca gcacttaatg    4560
catttgtgtc tcagactcta accagacaag cagaggttag ggctagtaga caacttgcca    4620
aagacaaggt taatgaatgt gttaggtctc agtctcagag attcggattc tgtggtaatg    4680
gtacacattt gttttcacta gcaaatgcag caccaaatgg catgattttc tttcatacag    4740
tactattacc aacagcttat gaaactgtaa cagcttggtc aggtatttgt gcttcagatg    4800
gcgatcgcac tttcggactt gtcgttaaag atgtgcagtt gacgttgttt cgtaatctag    4860
atgcaaagtt ctatttgacc cccagaacta tgtatcagcc tagagttgca actagttctg    4920 atttttgttca aattgaaggg tgtgatgtgt tgtttgtcaa cgcgactgta attgatttgc    4980
```

```
ctagtattat acctgactat attgacatta atcaaactgt tcaagacata ttagaaaatt    5040
acagaccaaa ctggactgta cctgaattta cacttgatat tttcaacgca acctatttaa    5100
atctgactgg tgaaattgat gacttagagt ttaggtcaga aaagctacat aacactacag    5160
tagaacttgc cattctcatt gataacatta ataatacatt agtcaatctt gaatggctca    5220
atagaattga aacttatgta aaatggcctt ggtatgtgtg gctactgata ggtttagtag    5280
tagtattttg cataccatta ctgctatttt gctgttttag cacaggttgt tgtggatgca    5340
taggttgttt aggaagttgt tgtcactcta tatgtagtag aagacaattt gaaaattatg    5400
aaccaattga aaaagtgcat gtccactaaa tttaaagtta aggatgttga ataaattcct    5460
taagaactaa acttattagt cattacaggt cttgtatgga cattgtcaaa tctattgaca    5520
tattcgtaga cgctgtactt gacgaacttg accgtgcata ctttgctgta actcttaaag    5580
tagaatttaa gactggtaaa ctacttgtgt gtataggttt tggtgacaca cttcttgagg    5640
ctaaggacaa agcgtatgct aagcttggtc tctcctttat tgaagaagtc aatagtcata    5700
cagttgttta gtattactgt ttacaagttt aaagccaaat tttggtataa actacctttt    5760
gaaactagac tttgtatcat taaacacaca agacccaaag cattaagtgt tacaaaacaa    5820
gtaaagagag attatagaaa aattgccatt ctaaattcca tgcgaaaatg attggtggac    5880
tttttcttaa cactcttagt tttgtaattg ttagtaacca tgttattgtt aataacacag    5940
caaatgtgca tactacacaa catgaaaatg ttatagtaca acagcattag gttgttagtg    6000
ctagaacaca aaattattac ccagagttca gcatcgctgt actctttgta tcatttttgg    6060
ctttgtaccg tagtacaaac tttaagacgt gtgtcggcat cttaatgttt aagattgtat    6120
caatgacact tgtagggcct atgcttatag catatggtta ctacattgat ggcattgtta    6180
caataactgt cttagcttta agatttttct acttagcata cttttggtat gttaatagta    6240
ggtccgaatt tatttatac aatacaacga cactcatgtt tgtacatggc agagctgcac    6300
cgtttatgag aagttctcac agctctattt atgtcacatt gtatggtggc ataaattata    6360
tgtttgtgaa tgacctcacg ttgcattttg tagaccctat gcttgtaaga atagcaatac    6420
gtggcttagc tcatgctgat ctaactgttt ttagagcagt tgaacttctc aatggtgatt    6480
ttatatatgt attttcacag gagcccgtag ccggtgttta caatgcagcc tcttctcagg    6540
cggttctaaa cgaaattgac ttaaaagaag aagaagaaga ccataactat gacgttccct    6600
agggcattta ctatcataga tgaccatggc atggttgtta gcgtcttctt ctggctcctg    6660
ttgataatta tattgatatt gttttcaata gcattgctaa atgttattaa attgtgcatg    6720
gtatgttgca atttgggtaa gactattata gtactacctg cacgccatgc atatgatgcc    6780
tataagacct ttatgcaaac caaggcatat aatcccgacg aagcattttt ggtttgaact    6840
aaacaaaatg aagtacattt tgctaatact cgcgtgcata attgcatgcg tttatggtga    6900
acgctactgt gccatgcaag acagtggctt gcagtgtatt aatggcacaa attcaagatg    6960
tcaaacctgc tttgaacgtg gtgatcttat ttggcatctt gctaactgga acttcagctg    7020
gtctgtaata ttgattgttt ttataacagt gttacaatat ggcagaccac aatttagctg    7080
gctcgtttat ggcattaaaa tgctgatcat gtggctatta tggcctattg ttctagcgct    7140
tacgattttt aatgcatact ctgagtacca agtttccaga tatgtaatgt tcggctttag    7200
tgttgcaggt gcagttgtaa cgtttgcact ttggatgatg tattttgtga gatctgttca    7260
gctatataga agaaccaaat catggtggtc ttttaatcct gagactaatg caattctttg    7320
tgttaatgca ttgggtagaa gttatgtgct tcccttagat ggtactccta caggtgttac    7380
```

```
ccttactcta ctttcaggaa atctatatgc tgaaggtttc aaaatggctg gtggtttaac     7440
catcgagcat ttgcctaaat acgtcatgat tgctacacct agtagaacca tcgtttatac     7500
attagttgga aaacaattaa aagcaactac tgccacagga tgggcttact acgtaaaatc     7560
taaagctggt gattactcaa cagaagcacg tactgacaat ttgagtgaac atgaaaaatt     7620
attacatatg gtgtaactaa actttcaaat ggccacacag gacaacgcg tcaactgggg      7680 agatgaacct tccaaaagac gtggtcgttc taactctcgt ggtcggaaga ataatgatat     7740
acctttgtca ttctacaacc ccattaccct cgaacaagga tctaaatttt ggaatttatg     7800
tccgagagac cttgttccca aggaatagg taataaggat caacaaattg gttattggaa      7860
tagacagatt cgttatcgta ttgtaaaagg ccagcgtaag gaactcgctg agaggtggtt     7920
cttttacttc ttaggtacag gacctcatgc tgatgctaaa ttcaaagaca agattgatgg     7980
agtcttctgg gttgcaaggg atggtgccat gaacaagccc acaacgcttg gcactcgtgg     8040
aaccaataac gaatccaaac cactgagatt tgatggtaag ataccgccac agtttcagct     8100
tgaagtgaac cgttctagga acaattcaag gtctggttct cagtctagat ctgtttcaag     8160
aaacagatct caatctagag gaagacacca ttccaataac cagaataata atgttgagga     8220
tacaattgta gccgtgcttg aaaaattagg tgttactgac aaacaaaggt cacgttctaa     8280
acctagagaa cgtagtgatt ccaaacctag ggacacaaca cctaagaatg ccaacaaaca     8340 caccctggaag aaaactgcag gcaagggaga tgtgacaact ttctatggtg ctagaagtag     8400
ttcagctaac tttggtgata gtgatctcgt tgccaatggt aacgctgcca atgctaccc      8460 tcagatagct gaatgtgttc catcagtgtc tagcataatc tttggcagtc aatggtctgc     8520
tgaagaagct ggtgatcaag tgaaagtcac gctcactcac acctactacc tgccaaagga     8580
tgatgccaaa actagtcaat tcctagaaca gattgacgct acaagcgac cttctgaagt      8640 ggctaaggat cagaggcaaa gaagatcccg ttctaagtct gctgataaga agcctgagga     8700
gttgtctgta actcttgtgg aggcatacac agatgtgttt gatgacacac aggttgagat     8760
gattgatgag gttacgaact aaacgcatgc tcgttttcgt ccatgctgta cttgtaacag     8820 cttaatctt actactaatt ggtagaatcc aattactaga aaggttgtta ctcagtcatc      8880
tgcttaatct tacaacagtc agtaatgttt taggtgtgcc tgacagtagt ctgcgtgtaa     8940
attgtttgca gcttttgaaa ccagactgcc ttgattttaa tatcttacat aaagttttag     9000
cagaaaccag gttactagta gtagtactgc gagtgatctt tctagttctt ctagggtttt     9060
cctgctatac attgttgggt gcattatttt aacatcatga ttgttgtaat ccttgtgtgt     9120
atctttttgg ctaatggaat taaagctact gctgtgcaaa atgaccttca tgaacatccc     9180
gttcttacct gggatttatt acagcatttc ataggacata ccctctacat tacaacacac     9240
caggtcttag cactaccgct tggatctcgt gttgagtgtg agggtatcga aggtttcaat     9300
tgcacatggc ctggctttca agatcctgca catgatcata ttgatttcta ctttgatctt     9360
tctaatcctt tctattcatt tgtagataat ttttatattg taagtgaggg aaatcaaaga     9420
atcaatctca gattggttgg tgctgtgcca aaacaaaaga gattaaatgt tggttgtcat     9480
acatcatttg ctgttgatct tccatttggg attcagatat accatgacag ggattttcaa     9540
caccctgttg atggcagaca tctagattgt actcacagag tgtactttgt gaagtactgt     9600
ccacataacc tgcatggtta ttgctttaat gagaggctga agtttatga cttgaagcaa      9660 ttcagaagca agaaggtctt cgacaaaatc aaccaacatc ataaaactga gttataaggc     9720
```

```
aacccgatgt ctaaaactgg tctttccgag gaattacggg tcatcgcgct gcctactctt   9780
gtacagaatg gtaagcacgt gtaataggag gtacaagcaa ccctattgca tattaggaag   9840
tttagatttg atttggcaat gctagattta gtaatttaga gaagtttaaa gatccgctat   9900
gacgagccaa caatggaaga gctaacgtct ggatctagtg attgtttaaa atgtaaaatt   9960
gtttgaaaat tttccttttg atagtgatac aaaaaaaaaa aaaaaaagcg gccgcaaaat  10020
tcttgaagac gaaagggcct cgtgatacgc ctatttttat aggttaatgt catgataata  10080
atggtttctt agacgtcagg tggcactttt cggggaaatg tgcgcggaac ccctatttgt  10140
ttatttttct aaatacattc aaatatgtat ccgctcatga caataaacc ctgataaatg   10200
cttcaataat attgaaaaag gaagagtatg agtattcaac atttccgtgt cgcccttatt  10260
ccctttttg cggcattttg ccttcctgtt tttgctcacc cagaaacgct ggtgaaagta   10320
aaagatgctg aagatcagtt gggtgcacga gtgggttaca tcgaactgga tctcaacagc  10380
ggtaagatcc ttgagagttt tcgccccgaa gaacgttttc caatgatgag cactttaaa   10440
gttctgctat gtggcgcggt attatcccgt gttgacgccg ggcaagagca actcggtcgc  10500
cgcatacact attctcagaa tgacttggtt gagtactcac cagtcacaga aaagcatctt  10560
acggatggca tgacagtaag agaattatgc agtgctgcca taaccatgag tgataacact  10620
gcggccaact tacttctgac aacgatcgga ggaccgaagg agctaaccgc ttttttgcac  10680
aacatggggg atcatgtaac tcgccttgat cgttgggaac cggagctgaa tgaagccata  10740
ccaaacgacg agcgtgacac cacgatgcct gcagcaatgg caacaacgtt gcgcaaacta  10800
ttaactggcg aactacttac tctagcttcc cggcaacaat taatagactg gatggaggcg  10860
gataaagttg caggaccact tctgcgctcg gcccttccgg ctggctggtt tattgctgat  10920
aaatctggag ccggtgagcg tgggtctcgc ggtatcattg cagcactggg gccagatggt  10980
aagccctccc gtatcgtagt tatctacacg acggggagtc aggcaactat ggatgaacga  11040
aatagacaga tcgctgagat aggtgcctca ctgattaagc attggtaact gtcagaccaa  11100
gtttactcat atatacttta gattgattta aaacttcatt tttaatttaa aaggatctag  11160
gtgaagatcc ttttttgataa tctcatgacc aaaatccctt aacgtgagtt ttcgttccac  11220
tgagcgtcag accccgtaga aaagatcaaa ggatcttctt gagatccttt ttttctgcgc  11280
gtaatctgct gcttgcaaac aaaaaaacca ccgctaccag cggtggtttg tttgccggat  11340
caagagctac caactctttt tccgaaggta actggcttca gcagagcgca gataccaaat  11400
actgtccttc tagtgtagcc gtagttaggc caccacttca agaactctgt agcaccgcct  11460
acatacctcg ctctgctaat cctgttacca gtggctgctg ccagtggcga taagtcgtgt  11520
cttaccgggt tggactcaag acgatagtta ccggataagg cgcagcggtc gggctgaacg  11580
gggggttcgt gcacacagcc cagcttggag cgaacgacct acaccgaact gagataccta  11640
cagcgtgagc tatgagaaag cgccacgctt cccgaaggga gaaaggcgga caggtatccg  11700
gtaagcggca gggtcggaac aggagagcgc acgagggagc ttccaggggg aaacgcctgg  11760
tatctttata gtcctgtcgg gtttcgccac ctctgacttg agcgtcgatt tttgtgatgc  11820
tcgtcagggg gcggagcct atggaaaaac gccagcaacg cggccttttt acggttcctg   11880
gccttttgct ggccttttgc tcacatgttc tttcctgcgt tatccctga ttctgtggat   11940
aaccgtatta ccgcctttga gtgagctgat accgctcgcc gcagccgaac gaccgagcgc  12000
agcgagtcag tgagcgagga agcggaagag cgcctgatgc ggtattttct ccttacgcat  12060
ctgtgcggta tttcacaccg catatggtgc actctcagta caatctgctc tgatgccgca  12120
```

```
tagttaagcc agtatacact ccgctatcgc tacgtgactg ggtcatggct gcgccccgac    12180
acccgccaac acccgctgac gcgccctgac gggcttgtct gctcccggca tccgcttaca    12240
gacaagctgt gaccgtctcc gggagctgca tgtgtcagag gttttcaccg tcatcaccga    12300
aacgcgcgag gcagctgcgg taaagctcat cagcgtggtc gtgaagcgat tcacagatgt    12360
ctgcctgttc atccgcgtcc agctcgttga gtttctccag aagcgttaat gtctggcttc    12420
tgataaagcg ggccatgtta agggcggttt tttcctgttt ggtcactgat gcctccgtgt    12480 aaggggatt tctgttcatg ggggtaatga taccgatgaa acgagagagg atgctcacga    12540
tacgggttac tgatgatgaa catgcccggt tactggaacg ttgtgagggt aaacaactgg    12600
cggtatggat gcggcgggac cagagaaaaa tcactcaggg tcaatgccag cgcttcgtta    12660
atacagatgt aggtgttcca cagggtagcc agcagcatcc tgcgatgcag atccggaaca    12720
taatggtgca gggcgctgac ttccgcgttt ccagacttta cgaaacacgg aaaccgaaga    12780
ccattcatgt tgttgctcag gtcgcagacg ttttgcagca gcagtcgctt cacgttcgct    12840
cgcgtatcgg tgattcattc tgctaaccag taaggcaacc ccgccagcct agccgggtcc    12900
tcaacgacag gagcacgatc atgcgcaccc gtggccagga cccaacgctg cccgagatgc    12960
gccgcgtgcg gctgctggag atggcggacg cgatggatat gttctgccaa gggttggttt    13020
gcgcattcac agttctccgc aagaattgat tggctccaat tcttggagtg gtgaatccgt    13080
tagcgaggtg ccgccggctt ccattcaggt cgaggtggcc cggctccatg caccgcgacg    13140
caacgcgggg aggcagacaa ggtatagggc ggcgcctaca atccatgcca acccgttcca    13200
tgtgctcgcc gaggcggcat aaatcgccgt gacgatcagc ggtccagtga tcgaagttag    13260
gctggtaaga gccgcgagcg atccttgaag ctgtccctga tggtcgtcat ctacctgcct    13320
ggacagcatg gcctgcaacg cgggcatccc gatgccgccg gaagcgagaa gaatcataat    13380
ggggaaggcc atccagcctc gcgtcgcgaa cgccagcaag acgtagccca gcgcgtcggc    13440
cgccatgccg gcgataatgg cctgcttctc gccgaaacgt ttggtggcgg gaccagtgac    13500
gaaggcttga gcgagggcgt gcaagattcc gaataccgca agcgacaggc cgatcatcgt    13560
cgcgctccag cgaaagcggt cctcgccgaa aatgacccag agcgctgccg gcacctgtcc    13620
tacgagttgc atgataaaga agacagtcat aagtgcggcg acgatagtca tgccccgcgc    13680
ccaccggaag gagctgactg ggttgaaggc tctcaagggc atcggtcgac gctctccctt    13740
atgcgactcc tgcattagga agcagcccag tagtaggttg aggccgttga gcaccgccgc    13800
cgcaaggaat ggtgcatgca aggagatggc gcccaacagt cccccggcca cggggcctgc    13860
caccataccc acgccgaaac aagcgctcat gagcccgaag tggcgagccc gatcttcccc    13920
atcggtgatg tcggcgatat aggcgccagc aaccgcacct gtggcgccgg tgatgccggc    13980
cacgatgcgt ccggcgtaga ggatccacag gacgggtgtg gtcgccatga tcgcgtagtc    14040
gatagtggct ccaagtagcg aagcgagcag gactgggcgg cggccaaagc ggtcggacag    14100
tgctccgaga acgggtgcgc atagaaattg catcaacgca tatagcgcta gcagcacgcc    14160
atagtgactg gcgatgctgt cggaatggac gatccg                              14196
```

<210> SEQ ID NO 80
<211> LENGTH: 13817
<212> TYPE: DNA
<213> ORGANISM: Artificial Sequence
<220> FEATURE:
<223> OTHER INFORMATION: Description of Artificial Sequence: sequence of plasmid pBRDI2

<400> SEQUENCE: 80

```
ctcgagtcga aattaatacg actcactata gggttttaa agtaaagtga gtgtagcgtg        60
gctataactc ttcttttact ttaactagcc ttgtgctaga tttgtcttcg gacaccaact      120
cgaactaaac gaaatatttg tctctctatg aaaccataga agacaagcgt tgattatttc      180
accagtttgg caatcactcc taggaacggg gttgagagaa cggcgcacca gggttccgtc      240
cctgtttggt aagtcgtcta gtattagctg cggcggttcc gcccgtcgta gttgggtaga      300
ccgggttccg tcctgtgatc tccctcgccg gccgccagga gaatgagttc caaacaattt      360
aagatcctcg ttaatgagga ctaccaagtc aacgttccta gccttccttt ccgtgacgca      420
ctgcaggaaa ttaagtactg ctaccgtaac ggttttgatg ctatgtcttc gtgcctgaa       480
taccgtcgtg acctagttga ttgcaatcgt aaggatcact acgtcattgg tgttttgggt      540
aacggaataa gtgatcttaa acctgttctc cttaccgaac cttccgtcat gttgcagggt      600
ttcattgtta gagccaactg caatggcgtt cttgaggact ttgaccttaa attcgcccgt      660
actggaaacg gcgccatata tgtggaccaa tacatgtgtg gtgctgatgg aaagccagtt      720
attgaaggtg agctctggac tgtgttttgt acaagtgtta atacgtcatc atcagaaggt      780
tttctgattg gtattaacta cttaggacca tactgtgaca agcaatagt agatggaaat       840
ataatgcatg ccaattatat attttggaga aactctacaa ttatggctct atcacataac      900
tcagtcctag acactccaaa atttaagtgc cgttgtaaca atgcacttat tgttaattta      960
aaagaaaaag aattgaatga aatggtcgtt ggattactaa ggaagggtaa gttactcatt     1020
agaaataatg gcaagctact aaactttggt aatcatttag ttaatgtgcc atgctgttcg     1080
tgtttattct attttgccc tcttgtttag ggtatattgg tgattttaga tgtatccagc      1140
ttgtgaattc aaacggtgct aatgttagtg ctccaagcat tagcactgag accgttgaag     1200
tttcacaagg cctggggaca tattatgtgt tagatcgagt ttatttaaat gccacattat     1260
tgcttactgg ttactacccg gtcgatggtt ctaagtttag aaacctcgct cttaggggaa     1320
ctaactcagt tagcttgtcg tggtttcaac caccctattt aaatcagttt aatgatggca     1380
tatttgcgaa ggtgcagaac cttaagacaa gtacgccatc aggtgcaact gcatattttc     1440
ctactatagt tataggtagt ttgttttggct atacttccta taccgttgta atagagccat     1500
ataatggtgt tataatggcc tcagtgtgcc agtataccat ttgtcagtta ccttacactg     1560
attgtaagcc taacactaat ggtaataagc ttataggggtt ttggcacacg gatgtaaaac     1620
ccccaatttg tgtgttaaag cgaaatttca cgcttaatgt taatgctgat gcattttatt     1680
ttcatttta ccaacatggt ggtacttttt atgcgtacta tgcggataaa ccctccgcta      1740
ctacgttttt gtttagtgta tatattggcg atattttaac acagtattat gtgttacctt     1800
tcatctgcaa cccaacagct ggtagcactt ttgctccgcg ctattgggtt acacctttgg     1860
ttaagcgcca atatttgttt aatttcaacc agaagggtgt cattactagt gctgttgatt     1920
gtgctagtag ttataccagt gaaataaaat gtaagaccca gagcatgtta cctagcactg     1980
gtgtctatga gttatccggt tatacggtcc aaccagttgg agttgtatac cggcgtgttg     2040
ctaacctccc agcttgtaat atagaggagt ggcttactgc taggtcagtc ccctccctc      2100
tcaactggga gcgtaagact tttcagaatt gtaatttaa tttaagcagc ctgttacgtt      2160
atgttcaggc tgagagtttg ttttgtaata atatcgatgc ttccaaagtg tatggcaggt     2220
gctttggtag tatttcagtt gataagtttg ctgtaccccg aagtaggcaa gttgatttac     2280
```

```
agcttggtaa ctctggattt ctgcagactg ctaattataa gattgataca gctgccactt   2340
cgtgtcagct gcattacacc ttgcctaaga ataatgtcac cataaacaac cataacccct   2400
cgtcttggaa taggaggtat ggctttaatg atgctggcgt ctttggcaaa aaccaacatg   2460
acgttgttta cgctcagcaa tgttttactg taagatctag ttattgcccg tgtgctcaac   2520
cggacatagt tagcccttgc actactcaga ctaagcctaa gtctgctttt gttaatgtgg   2580
gtgaccattg tgaaggctta ggtgttttag aagataattg tggcaatgct gatccacata   2640
agggttgtat ctgtgccaac aattcattta ttggatggtc acatgatacc tgccttgtta   2700
atgatcgctg ccaaattttt gctaatatat tgttaaatgg cattaatagt ggtaccacat   2760
gttccacaga tttgcagttg cctaatactg aagtggttac tggcatttgt gtcaaatatg   2820
acctctacgg tattactgga caaggtgttt ttaaagaggt taaggctgac tattataata   2880
gctggcaaac ccttctgtat gatgttaatg gtaatttgaa tggttttcgt gatcttacca   2940
ctaacaagac ttatacgata aggagctgtt atagtggccg tgtttctgct gcatttcata   3000
aagatgcacc cgaaccggct ctgctctatc gtaatataaa ttgtagctat gttttagca    3060 ataatatttc ccgtgaggag aacccactta attactttga tagttatttg ggttgtgttg   3120
ttaatgctga taaccgcacg gatgaggcgc ttcctaattg tgatctccgt atgggtgctg   3180
gcttatgcgt tgattattca aaatcacgca gggctcaccg atcagtttct actggctatc   3240
ggttaactac atttgagcca tacactccga tgttagttaa tgatagtgtc caatccgttg   3300
atggattata tgagatgcaa ataccaacca attttactat tgggcaccat gaggagttca   3360
ttcaaactag atctccaaag gtgactatag attgtgctgc atttgtctgt ggtgataaca   3420
ctgcatgcag gcagcagttg gttgagtatg gctctttctg tgttaatgtt aatgccattc   3480
ttaatgaggt taataacctc ttggataata tgcaactaca agttgctagt gcattaatgc   3540
agggtgttac tataagctcg agactgccag acggcatctc aggccctata gatgacatta   3600
attttagtcc tctacttgga tgcataggtt caacatgtgc tgaagacggc aatggaccta   3660
gtgcaatccg agggcgttct gctatagagg atttgttatt tgacaaggtc aaattatctg   3720
atgttggctt tgtcgaggct tataataatt gcaccggtgg tcaagaagtt cgtgacctcc   3780
tttgtgtaca atcttttaat ggcatcaaag tattacctcc tgtgttgtca gagagtcaga   3840
tctctggcta cacaaccggt gctactgcgg cagctatgtt cccaccgtgg tcagcagctg   3900
ccggtgtgcc atttagttta agtgttcaat atagaattaa tggtttaggt gtcactatga   3960
atgtgcttag tgagaaccaa aagatgattg ctagtgcttt taacaatgcg ctgggtgcta   4020
tccaggatgg gtttgatgca accaattctg ctttaggtaa gatccagtcc gttgttaatg   4080
caaatgctga agcactcaat aacttactaa atcagctttc taacaggttt ggtgctatta   4140
gtgcttcttt acaagaaatt ctaactcggc ttgaggctgt agaagcaaaa gcccagatag   4200
atcgtcttat taatggcagg ttaactgcac ttaatgcgta tatatccaag caacttagtg   4260
atagtacgct tattaaagtt agtgctgctc aggccataga aaaggtcaat gagtgcgtta   4320
agagccaaac cacgcgtatt aatttctgtg gcaatggtaa tcatatatta tctcttgtcc   4380
agaatgcgcc ttatggctta tattttatac acttcagcta tgtgccaata tcctttacaa   4440
ccgcaaatgt gagtcctgga cttgcatttt ctggtgatag aggattagca cctaaagctg   4500
gatattttgt tcaagatgat ggagaatgga gttcacagg  cagttcatat tactaccctg   4560
aacccattac agataaaaac agtgtcatta tgagtagttg cgcagtaaac tacacaaagg   4620
cacctgaagt tttcttgaac acttcaatac ctaatccacc cgactttaag gaggagttag   4680
```

```
ataaatggtt taagaatcag acgtctattg cgcctgattt atctctcgat ttcgagaagt    4740
taaatgttac tttgctggac ctgacgtatg agatgaacag gattcaggat gcaattaaga    4800
agttaaatga gagctacatc aacctcaagg aagttggcac atatgaaatg tatgtgaaat    4860
ggccttggta tgtgtggcta ctgataggtt tagtagtagt attttgcata ccattactgc    4920
tattttgctg ttttagcaca ggttgttgtg gatgcatagg ttgtttagga agttgttgtc    4980
actctatatg tagtagaaga caatttgaaa attatgaacc aattgaaaaa gtgcatgtcc    5040
actaaattta aagttaagga tgttaataa attccttaag aactaaactt attagtcatt    5100
acaggtcttg tatggacatt gtcaaatcta ttgacatatt cgtagacgct gtacttgacg    5160
aacttgaccg tgcatacttt gctgtaactc ttaaagtaga atttaagact ggtaaactac    5220
ttgtgtgtat aggttttggt gacacacttc ttgaggctaa ggacaaagcg tatgctaagc    5280
ttggtctctc ctttattgaa gaagtcaata gtcatacagt tgtttagtat tactgtttac    5340
aagtttaaag ccaaattttg gtataaacta ccttttgaaa ctagactttg tatcattaaa    5400
cacacaagac ccaaagcatt aagtgttaca aaacaagtaa agagagatta tagaaaaatt    5460
gccattctaa attccatgcg aaaatgattg gtggactttt tcttaacact cttagttttg    5520
taattgttag taaccatgtt attgttaata acacagcaaa tgtgcatact acacaacatg    5580
aaaatgttat agtacaacag cattaggttg ttagtgctag aacacaaaat tattacccag    5640
agttcagcat cgctgtactc tttgtatcat ttttggcttt gtaccgtagt acaaacttta    5700
agacgtgtgt cggcatctta atgtttaaga ttgtatcaat gacacttgta gggcctatgc    5760
ttatagcata tggttactac attgatggca ttgttacaat aactgtctta gctttaagat    5820
ttttctactt agcatacttt tggtatgtta atagtaggtc cgaatttatt ttatacaata    5880
caacgacact catgtttgta catggcagag ctgcaccgtt tatgagaagt tctcacagct    5940
ctatttatgt cacattgtat ggtggcataa attatatgtt tgtgaatgac ctcacgttgc    6000
attttgtaga ccctatgctt gtaagaatag caatacgtgg cttagctcat gctgatctaa    6060
ctgtttttag agcagttgaa cttctcaatg gtgattttat atatgtattt tcacaggagc    6120
ccgtagccgg tgtttacaat gcagcctctt ctcaggcggt tctaaacgaa attgacttaa    6180
aagaagaaga agaagaccat aactatgacg ttccctaggg catttactat catagatgac    6240
catggcatgg ttgttagcgt cttcttctgg ctcctgttga taattatatt gatattgttt    6300
tcaatagcat tgctaaatgt tattaaattg tgcatggtat gttgcaattt gggtaagact    6360
attatagtac tacctgcacg ccatgcatat gatgcctata agacctttat gcaaaccaag    6420
gcatataatc ccgacgaagc attttttggtt tgaactaaac aaaatgaagt acattttgct    6480
aatactcgcg tgcataattg catgcgttta tggtgaacgc tactgtgcca tgcaagacag    6540
tggcttgcag tgtattaatg gcacaaattc aagatgtcaa acctgctttg aacgtggtga    6600
tcttatttgg catcttgcta actggaactt cagctggtct gtaatattga ttgttttat    6660 aacagtgtta caatatggca gaccacaatt tagctggctc gtttatggca ttaaaatgct    6720
gatcatgtgg ctattatggc ctattgttct agcgcttacg attttttaatg catactctga    6780 gtaccaagtt tccagatatg taatgttcgg ctttagtgtt gcaggtgcag ttgtaacgtt    6840
tgcactttgg atgatgtatt ttgtgagatc tgttcagcta tatagaagaa ccaaatcatg    6900
gtggtctttt aatcctgaga ctaatgcaat tctttgtgtt aatgcattgg gtagaagtta    6960
tgtgcttccc ttagatggta ctcctacagg tgttacccct actctacttt caggaaatct    7020
```

```
atatgctgaa ggtttcaaaa tggctggtgg tttaaccatc gagcatttgc ctaaatacgt    7080
catgattgct acacctagta gaaccatcgt ttatacatta gttggaaaac aattaaaagc    7140
aactactgcc acaggatggg cttactacgt aaaatctaaa gctggtgatt actcaacaga    7200
agcacgtact gacaatttga gtgaacatga aaaattatta catatggtgt aactaaactt    7260
tcaaatggcc acacagggac aacgcgtcaa ctggggagat gaaccttcca aaagacgtgg    7320
tcgttctaac tctcgtggtc ggaagaataa tgatatacct ttgtcattct acaacccat     7380
taccctcgaa caaggatcta aattttggaa tttatgtccg agagaccttg ttcccaaagg    7440
aataggtaat aaggatcaac aaattggtta ttggaataga cagattcgtt atcgtattgt    7500
aaaaggccag cgtaaggaac tcgctgagag gtggttcttt tacttcttag gtacaggacc    7560
tcatgctgat gctaaattca agacaagatt gatggagtc ttctgggttg caagggatgg     7620
tgccatgaac aagcccacaa cgcttggcac tcgtggaacc aataacgaat ccaaaccact    7680
gagatttgat ggtaagatac cgccacagtt tcagcttgaa gtgaaccgtt ctaggaacaa    7740
ttcaaggtct ggttctcagt ctagatctgt ttcaagaaac agatctcaat ctagaggaag    7800
acaccattcc aataaccaga ataataatgt tgaggataca attgtagccg tgcttgaaaa    7860
attaggtgtt actgacaaac aaaggtcacg ttctaaacct agagaacgta gtgattccaa    7920
acctagggac acaacaccta agaatgccaa caaacacacc tggaagaaaa ctgcaggcaa    7980
gggagatgtg acaactttct atggtgctag aagtagttca gctaactttg gtgatagtga    8040
tctcgttgcc aatggtaacg ctgccaaatg ctaccctcag atagctgaat gtgttccatc    8100
agtgtctagc ataatctttg gcagtcaatg gtctgctgaa gaagctggtg atcaagtgaa    8160
agtcacgctc actcacacct actacctgcc aaaggatgat gccaaaacta gtcaattcct    8220
agaacagatt gacgcttaca agcgaccttc tgaagtggct aaggatcaga ggcaaagaag    8280
atcccgttct aagtctgctg ataagaagcc tgaggagttg tctgtaactc ttgtggaggc    8340
atacacagat gtgtttgatg acacacaggt tgagatgatt gatgaggtta cgaactaaac    8400
gcatgctcgt tttcgtccat gctgtacttg taacagcttt aatcttacta ctaattggta    8460
gaatccaatt actagaaagg ttgttactca gtcatctgct taatcttaca acagtcagta    8520
atgttttagg tgtgcctgac agtagtctgc gtgtaaattg tttgcagctt ttgaaaccag    8580
actgccttga ttttaatatc ttacataaag ttttagcaga aaccaggtta ctagtagtag    8640
tactgcgagt gatctttcta gttcttctag ggttttcctg ctatacattg ttgggtgcat    8700
tattttaaca tcatgattgt tgtaatcctt gtgtgtatct ttttggctaa tggaattaaa    8760
gctactgctg tgcaaaatga ccttcatgaa catcccgttc ttacctggga tttattacag    8820
catttcatag gacatacccct ctacattaca acacaccagg tcttagcact accgcttgga    8880
tctcgtgttg agtgtgaggg tatcgaaggt ttcaattgca catggcctgg ctttcaagat    8940
cctgcacatg atcatattga tttctacttt gatcttctca tcctttcta ttcatttgta    9000
gataatttt atattgtaag tgagggaaat caaagaatca atctcagatt ggttggtgct    9060
gtgccaaaac aaaagagatt aaatgttggt tgtcatacat catttgctgt tgatcttcca    9120
tttgggattc agatataccca tgacagggat tttcaacacc ctgttgatgg cagacatcta    9180
gattgtactc acagagtgta ctttgtgaag tactgtccac ataacctgca tggttattgc    9240
tttaatgaga ggctgaaagt ttatgacttg aagcaattca gaagcaagaa ggtcttcgac    9300
aaaatcaacc aacatcataa aactgagtta taaggcaacc cgatgtctaa aactggtctt    9360
tccgaggaat tacgggtcat cgcgctgcct actcttgtac agaatggtaa gcacgtgtaa    9420
```

```
taggaggtac aagcaaccct attgcatatt aggaagttta gatttgattt ggcaatgcta   9480
gatttagtaa tttagagaag tttaaagatc cgctatgacg agccaacaat ggaagagcta   9540
acgtctggat ctagtgattg tttaaaatgt aaaattgttt gaaaattttc cttttgatag   9600
tgatacaaaa aaaaaaaaaa aaagcggccg caaaattctt gaagacgaaa gggcctcgtg   9660
atacgcctat ttttataggt taatgtcatg ataataatgg tttcttagac gtcaggtggc   9720
acttttcggg gaaatgtgcg cggaacccct atttgtttat ttttctaaat acattcaaat   9780
atgtatccgc tcatgagaca ataaccctga taaatgcttc aataatattg aaaaaggaag   9840
agtatgagta ttcaacattt ccgtgtcgcc cttattccct tttttgcggc attttgcctt   9900
cctgtttttg ctcacccaga aacgctggtg aaagtaaaag atgctgaaga tcagttgggt   9960
gcacgagtgg gttacatcga actggatctc aacagcggta agatccttga gagttttcgc  10020
cccgaagaac gttttccaat gatgagcact tttaaagttc tgctatgtgg cgcggtatta  10080
tcccgtgttg acgccgggca agagcaactc ggtcgccgca tacactattc tcagaatgac  10140
ttggttgagt actcaccagt cacagaaaag catcttacgg atggcatgac agtaagagaa  10200
ttatgcagtg ctgccataac catgagtgat aacactgcgg ccaacttact tctgacaacg  10260
atcggaggac cgaaggagct aaccgctttt ttgcacaaca tgggggatca tgtaactcgc  10320
cttgatcgtt gggaaccgga gctgaatgaa gccataccaa acgacgagcg tgacaccacg  10380
atgcctgcag caatggcaac aacgttgcgc aaactattaa ctggcgaact acttactcta  10440
gcttcccggc aacaattaat agactggatg gaggcggata aagttgcagg accacttctg  10500
cgctcggccc ttccggctgg ctggtttatt gctgataaat ctggagccgg tgagcgtggg  10560
tctcgcggta tcattgcagc actggggcca gatggtaagc cctcccgtat cgtagttatc  10620
tacacgacgg ggagtcaggc aactatggat gaacgaaata gacagatcgc tgagataggt  10680
gcctcactga ttaagcattg gtaactgtca gaccaagttt actcatatat actttagatt  10740
gatttaaaac ttcatttta atttaaaagg atctaggtga agatccttt tgataatctc   10800
atgaccaaaa tcccttaacg tgagttttcg ttccactgag cgtcagaccc cgtagaaaag  10860
atcaaaggat cttcttgaga tcctttttt ctgcgcgtaa tctgctgctt gcaaacaaaa   10920
aaaccaccgc taccagcggt ggtttgtttg ccggatcaag agctaccaac tcttttccg   10980
aaggtaactg gcttcagcag agcgcagata ccaaatactg tccttctagt gtagccgtag  11040
ttaggccacc acttcaagaa ctctgtagca ccgcctacat acctcgctct gctaatcctg  11100
ttaccagtgg ctgctgccag tggcgataag tcgtgtctta ccgggttgga ctcaagacga  11160
tagttaccgg ataaggcgca gcggtcgggc tgaacggggg gttcgtgcac acagcccagc  11220
ttggagcgaa cgacctacac cgaactgaga tacctacagc gtgagctatg agaaagcgcc  11280
acgcttcccg aagggagaaa ggcggacagg tatccggtaa gcggcagggt cggaacagga  11340
gagcgcacga gggagcttcc agggggaaac gcctggtatc tttatagtcc tgtcgggttt  11400
cgccacctct gacttgagcg tcgatttttg tgatgctcgt caggggggcg gagcctatgg  11460
aaaaacgcca gcaacgcggc cttttacgg ttcctggcct tttgctggcc ttttgctcac   11520
atgttctttc ctgcgttatc ccctgattct gtggataacc gtattaccgc ctttgagtga  11580
gctgataccg ctcgccgcag ccgaacgacc gagcgcagcg agtcagtgag cgaggaagcg  11640
gaagagcgcc tgatgcggta ttttctcctt acgcatctgt gcggtatttc acaccgcata  11700
tggtgcactc tcagtacaat ctgctctgat gccgcatagt taagccagta tacactccgc  11760
```

```
tatcgctacg tgactgggtc atggctgcgc cccgacaccc gccaacaccc gctgacgcgc    11820
cctgacgggc ttgtctgctc ccggcatccg cttacagaca agctgtgacc gtctccggga    11880
gctgcatgtg tcagaggttt tcaccgtcat caccgaaacg cgcgaggcag ctgcggtaaa    11940
gctcatcagc gtggtcgtga agcgattcac agatgtctgc ctgttcatcc gcgtccagct    12000
cgttgagttt ctccagaagc gttaatgtct ggcttctgat aaagcgggcc atgttaaggg    12060
cggttttttc ctgtttggtc actgatgcct ccgtgtaagg gggatttctg ttcatggggg    12120
taatgatacc gatgaaacga gagaggatgc tcacgatacg ggttactgat gatgaacatg    12180
cccggttact ggaacgttgt gagggtaaac aactggcggt atggatgcgg cgggaccaga    12240
gaaaaatcac tcagggtcaa tgccagcgct tcgttaatac agatgtaggt gttccacagg    12300
gtagccagca gcatcctgcg atgcagatcc ggaacataat ggtgcagggc gctgacttcc    12360
gcgtttccag actttacgaa acacggaaac cgaagaccat tcatgttgtt gctcaggtcg    12420
cagacgtttt gcagcagcag tcgcttcacg ttcgctcgcg tatcggtgat tcattctgct    12480
aaccagtaag gcaaccccgc cagcctagcc gggtcctcaa cgacaggagc acgatcatgc    12540
gcacccgtgg ccaggaccca acgctgcccg agatgcgccg cgtgcggctg ctggagatgg    12600
cggacgcgat ggatatgttc tgccaagggt tggtttgcgc attcacagtt ctccgcaaga    12660
attgattggc tccaattctt ggagtggtga atccgttagc gaggtgccgc cggcttccat    12720
tcaggtcgag gtggcccggc tccatgcacc gcgacgcaac gcggggaggc agacaaggta    12780
tagggcggcg cctacaatcc atgccaaccc gttccatgtg ctcgccgagg cggcataaat    12840
cgccgtgacg atcagcggtc cagtgatcga agttaggctg gtaagagccg cgagcgatcc    12900
ttgaagctgt ccctgatggt cgtcatctac ctgcctggac agcatggcct gcaacgcggg    12960
catcccgatg ccgccggaag cgagaagaat cataatgggg aaggccatcc agcctcgcgt    13020
cgcgaacgcc agcaagacgt agcccagcgc gtcggccgcc atgccggcga taatggcctg    13080
cttctcgccg aaacgtttgg tggcgggacc agtgacgaag gcttgagcga gggcgtgcaa    13140
gattccgaat accgcaagcg acaggccgat catcgtcgcg ctccagcgaa agcggtcctc    13200
gccgaaaatg acccagagcg ctgccggcac ctgtcctacg agttgcatga taaagaagac    13260
agtcataagt gcggcgacga tagtcatgcc ccgcgcccac cggaaggagc tgactgggtt    13320
gaaggctctc aagggcatcg gtcgacgctc tcccttatgc gactcctgca ttaggaagca    13380
gcccagtagt aggttgaggc cgttgagcac cgccgccgca aggaatggtg catgcaagga    13440
gatggcgccc aacagtcccc cggccacggg gcctgccacc atacccacgc cgaaacaagc    13500
gctcatgagc ccgaagtggc gagcccgatc ttccccatcg gtgatgtcgg cgatataggc    13560
gccagcaacc gcacctgtgg cgccggtgat gccggccacg atgcgtccgg cgtagaggat    13620
ccacaggacg ggtgtggtcg ccatgatcgc gtagtcgata tggctccaa gtagcgaagc    13680 gagcaggact gggcggcggc caaagcggtc ggacagtgct ccgagaacgg gtgcgcatag    13740
aaattgcatc aacgcatata gcgctagcag cacgccatag tgactggcga tgctgtcgga    13800
atggacgatc cgctcga                                                  13817
```